United States Patent
Gunning et al.

(10) Patent No.: US 10,077,284 B2
(45) Date of Patent: Sep. 18, 2018

(54) UBA5 INHIBITORS

(71) Applicant: THE GOVERNING COUNCIL OF THE UNIVERSITY OF TORONTO, Toronto (CA)

(72) Inventors: Patrick Thomas Gunning, Mississauga (CA); Sara R. Da Silva, Mississauga (CA); Stacey-Lynn Paiva, Brampton (CA); Julie Lynn Lukkarila, Mississauga (CA)

(73) Assignee: The Governing Council of The University of Toronto, Toronto, Ontario (CA)

( * ) Notice: Subject to any disclaimer, the term of this patent is extended or adjusted under 35 U.S.C. 154(b) by 0 days.

(21) Appl. No.: 15/315,123

(22) PCT Filed: May 29, 2015

(86) PCT No.: PCT/CA2015/000347
§ 371 (c)(1),
(2) Date: Nov. 30, 2016

(87) PCT Pub. No.: WO2015/179955
PCT Pub. Date: Dec. 3, 2015

(65) Prior Publication Data
US 2017/0107247 A1    Apr. 20, 2017

Related U.S. Application Data

(60) Provisional application No. 62/005,443, filed on May 30, 2014.

(51) Int. Cl.
| | | |
|---|---|---|
| *A01N 43/04* | (2006.01) |
| *A61K 31/70* | (2006.01) |
| *C07H 23/00* | (2006.01) |
| *A61K 31/7072* | (2006.01) |
| *A61K 31/706* | (2006.01) |
| *A61K 31/708* | (2006.01) |
| *A61K 31/7068* | (2006.01) |
| *A61K 31/7064* | (2006.01) |
| *A61K 31/7076* | (2006.01) |

(52) U.S. Cl.
CPC ............ *C07H 23/00* (2013.01); *A61K 31/706* (2013.01); *A61K 31/708* (2013.01); *A61K 31/7064* (2013.01); *A61K 31/7068* (2013.01); *A61K 31/7072* (2013.01); *A61K 31/7076* (2013.01)

(58) Field of Classification Search
None
See application file for complete search history.

(56) References Cited

U.S. PATENT DOCUMENTS

| 5,622,945 A | 4/1997 | Sessler et al. |
| 2012/0219495 A1 | 8/2012 | Yoo et al. |

FOREIGN PATENT DOCUMENTS

| CA | 2251072 | 10/1997 |

OTHER PUBLICATIONS

Dessolin et al. J. Med. Chem. (1999), vol. 42, pp. 229-241.*
Hershko, Avram; Heller, Hannah, Elias, Sarah and Ciechanover, Aaron. Components of Ubiquitin-Protein Ligase System. J. Biol. Chem. 1983, 258, 8206-8214.
Schulman, Branda A. and Harper and J. Wade. Ubiquitin-like protein activation by E1 enzymes: the apex for downstream signalling pathways. Nat Rev Mol Cell Biol., 2009, 10(5), 319-331.
Bacik, John-Paul, Walker, John R., Ali, Mohsin and Schimmer, Aaron D. Crystal Structure of the Human Ubiquitin-activating Enzyme 5 (UBA5) Bound to ATP. J. Biol. Chem. 2010, 285, 20273-20280.
Lemaire, Katleen, Moura, Rodrigo F., Granvik, Mikaela, Igoillo-Esteve, Mariana, Hohmeier, Hans E., Hendrickx, Nico, Newgard, Christopher B., Waelkens, Etienne, Cnop, Miriam and Schuit, Frans. Ubiquitin Fold Modifer 1 (UFM1) and Its Target UFBP1 Protect Pancreatic Beta Cells from ER Stress-Induced Apoptosis. PloS ONE. 2011, 6, 4, e18517.
Gannavaram, Sreenivas; Davey, Sonya Lakhal-Naouar, Ines; Duncan, Robert and Nakhasi, Hira L. Deletion of Ubiquitin Fold Modifier Protein Ufm1 Processing Peptidase Ufsp in L. donovani Abolishes Ufm1 Processing and Alters Pathogenesis. PLOS Neglected Tropical Diseases, 2014, 8 (2), e2707.
Gannavaram, Sreenivas; Connelly, Patricia S.; Daniels, Mathew P.; Duncan, Robert; Salotra, Poonam; and Nakhasi, Hira L. Deletion of mitochondrial associated ubiquitin fold modifier protein Ufm1 in Leishmania donovani results in loss of β-oxidation of fatty acids and blocks cell division in the amastigote stage. Molecular Microbiology 2012, 86(1), 187-198.
Gannavaram, Sreenivas; Shanna, Paresh; Duncan, Robert C;. Salotra, Poonam; Nakhasi, Hira L. Mitochondrial Associated Ubiquitin Fold Modifier-1 Mediated Protein Conjugation in Leishmania donovani. PLoS ONE 2011, 6 (1), e16156.
Komatsu M, Chiba T, Tatsumi K, Iemura S, Tanida I, Okazaki N, Ueno T, Kominami E, Natsume T, Tanaka K. A novel protein-conjugating system for Ufm1, a ubiquitin-fold modifier. EMBO J. 2004, 5; 23 (9),1977-86.
World Health Organization 2014, Fact Sheet No. 375: Leishmaniasis, < http://www.who.int/mediacentre/factsheets/fs375/en/.
World Health Organization 2010, Technical Report Series No. 949, Costs of medicines in current use for thetreatment of leishmaniasis. http://www.who.int/leishmaniasis/research/978_92_4_12_949_6_Annex6.pdf?ua=1.
Kanako Tatsumi, Harumi Yamamoto-Mukai, Ritsuko Shimizu, Satoshi Waguri, Yu-Shin Sou, Ayako Sakamoto, Choji Taya, Hiroshi Shitara, Takahiko Hara, Chin Ha Chung, Keiji Tanaka, Masayuki Yamamoto & Masaaki Komatsu. The Ufm1-activating enzyme Uba5 is indispensable for erythroid differentiation in mice. Nat. Comm. 2011, DOI: 10.1038/ncomms1182
L. Kedzierski (a1), Y. Zhu (a1) and E. Handman Leishmania vaccines: progress and problems. Parasitology 2006, 133 Suppl 2: S87-112.

(Continued)

*Primary Examiner* — Patrick T Lewis
(74) *Attorney, Agent, or Firm* — Bereskin & Parr LLP/S.E.N.C.R.L., s.r.l.; Michael Fenwick

(57) ABSTRACT

The present disclosure relates to compounds of the Formula (I), which are UBA5 inhibitors.

19 Claims, 28 Drawing Sheets

(56) References Cited

OTHER PUBLICATIONS

Mizushimaa, Tsunehiro; Tatsumib, Kanako; Ozakia, Yoko; Kawakamia, Tatsukuni; Suzukia, Atsuo; Ogasaharac, Kyoko; Komatsu, Masaaki; Kominamid, Eiki and Tanaka, Keiji Crystal structure of Ufc1, the Ufm1-conjugating anzyme. Biochem Biophys Res Commun. 2007, 362(4), 1079-84.

* cited by examiner

Figure 10

| Target Gene Symbol | %Ctrl @ 10000nM |
|---|---|
| ABL1(E255K)-phosphorylated | 92 |
| ABL1(T315I)-phosphorylated | 100 |
| ABL1-nonphosphorylated | 97 |
| ABL1-phosphorylated | 100 |
| ACVR1B | 86 |
| ADCK3 | 100 |
| AKT1 | 59 |
| AKT2 | 94 |
| ALK | 96 |
| AURKA | 97 |
| AURKB | 45 |
| AXL | 84 |
| BMPR2 | 95 |
| BRAF | 100 |
| BRAF(V600E) | 100 |
| BTK | 100 |
| CDK11 | 100 |
| CDK2 | 95 |
| CDK3 | 91 |
| CDK7 | 86 |
| CDK9 | 82 |
| CHEK1 | 92 |
| CSF1R | 93 |
| CSNK1D | 93 |
| CSNK1G2 | 100 |
| DCAMKL1 | 76 |
| DYRK1B | 86 |
| EGFR | 98 |
| EGFR(L858R) | 100 |
| EPHA2 | 100 |
| ERBB2 | 100 |
| ERBB4 | 100 |
| ERK1 | 100 |
| FAK | 83 |
| FGFR2 | 100 |
| FGFR3 | 100 |
| FLT3 | 95 |
| GSK3B | 100 |
| IGF1R | 100 |
| IKK-alpha | 97 |
| IKK-beta | 100 |
| INSR | 88 |
| JAK2(JH1domain-catalytic) | 100 |
| JAK3(JH1domain-catalytic) | 58 |
| JNK1 | 80 |
| JNK2 | 87 |
| JNK3 | 92 |
| KIT | 87 |

| Target Gene Symbol | %Ctrl @ 10000nM |
|---|---|
| KIT(D816V) | 97 |
| KIT(V559D,T670I) | 84 |
| LKB1 | 94 |
| MAP3K4 | 55 |
| MAPKAPK2 | 85 |
| MARK3 | 72 |
| MEK1 | 100 |
| MEK2 | 100 |
| MET | 100 |
| MKNK1 | 100 |
| MKNK2 | 97 |
| MLK1 | 99 |
| p38-alpha | 100 |
| p38-beta | 89 |
| PAK1 | 74 |
| PAK2 | 100 |
| PAK4 | 100 |
| PCTK1 | 100 |
| PDGFRA | 100 |
| PDGFRB | 74 |
| PDPK1 | 86 |
| PIK3C2B | 89 |
| PIK3CA | 95 |
| PIK3CG | 87 |
| PIM1 | 97 |
| PIM2 | 63 |
| PIM3 | 100 |
| PKAC-alpha | 69 |
| PLK1 | 100 |
| PLK3 | 100 |
| PLK4 | 93 |
| PRKCE | 64 |
| RAF1 | 93 |
| RET | 95 |
| RIOK2 | 66 |
| ROCK2 | 79 |
| RSK2(Kin.Dom.1-N-terminal) | 100 |
| SNARK | 97 |
| SRC | 96 |
| SRPK3 | 90 |
| TGFBR1 | 95 |
| TIE2 | 76 |
| TRKA | 97 |
| TSSK1B | 83 |
| TYK2(JH1domain-catalytic) | 100 |
| ULK2 | 100 |
| VEGFR2 | 97 |
| YANK3 | 92 |
| ZAP70 | 100 |

A = MRC9
B = A549
C = Sk – Luci 6

| Parameter | Value – no 5C-Z | Value – 5C-Z (5 µM) |
|---|---|---|
| $K_M$ | 16.5 ± 2.53 µM | 24.9 ± 9.63 µM |
| $V_{MAX}$ | 1.90 ± 0.096 pmol min$^{-1}$ | 0.988 ± 0.137 pmol min$^{-1}$ |
| $k_{cat}$ | 0.218 ± 0.010 min$^{-1}$ | 0.113 ± 0.016 min$^{-1}$ |

UBA5 INHIBITORS

CROSS REFERENCE TO RELATED APPLICATIONS

This is a national stage application of PCT/CA2015/000347, filed May 29, 2015, which claims priority from U.S. Provisional patent application Ser. No. 62/005,443 filed May 30, 2014, all of which are incorporated herein by reference in their entirety.

FIELD

The present disclosure relates to compounds of the Formula (I) which are UBA5 inhibitors.

INTRODUCTION

The UBA5 enzyme belongs to the E1 family of activating enzymes, which are responsible for initiating the labeling of intracellular proteins with small protein modifiers. These ubiquitin (Ub) and Ub-like (Ubl) modifiers destine target proteins for a variety of fates within the cell, including degradation by the 26S proteasome, depending on the nature and number of Ubl molecules attached.[1,2] In order to maintain fidelity and specificity of protein labeling, each Ubl modifier is activated by one specific E1 that catalyzes the adenylation of the C-terminal glycine carboxylate of the Ubl, followed by covalent attachment to an active site cysteine through a thioester bond to the E1.[1] The E1 catalyzes a second round of Ubl adenylation prior to binding to a specific subset of >30 conjugating E2 enzymes, which relieves the E1 of the first Ubl molecule through a trans-thiolation reaction that occurs between the thioester in the E1-Ubl conjugate and the active site cysteine residue of the E2.[1,2] The conjugating enzyme shuttles the Ubl to one of around 600 E3 ligase enzymes.[2] The E3 mediates the final step of protein labeling by binding to both the Ubl-E2 complex and the protein substrate, facilitating the transfer of the Ubl from the E2 to an exposed lysine residue on the target protein in the formation of an isopeptide linkage.[2]

The E1 enzymes are classified as canonical or non-canonical, depending on their tertiary structure.[2,3] The non-canonical UBA5 enzyme regulates the covalent modification of proteins with Ub-fold modifier 1 (UFM1), an 85 amino acid (~9.1 kDa) protein that exhibits strong structural homology with the Ub tertiary structure.[3,4] Physiologically, the UFM1 system has been implicated in erythroid development, where UBA5 knockout mice died in utero as a result of severe anaemia brought upon by defective megakaryocyte and erythrocyte differentiation.[5] Proteins of the UFM1 conjugation pathway are also upregulated in secretory cells that undergo endoplasmic reticulum (ER) stress, such as those found in the pancreatic islets of Langerhans, pancreatic acini, and seminal vesicles.[6] It has been found that conjugation of UFM1 to its downstream substrates, UFM1-binding protein 1 containing a Pcl domain (UFBP1) and CDK5RAP3, produces an anti-apoptotic effect in pancreatic islet cells upon the induction of ER stress.[6] The UFM1 system thus appears to play a protective role in maintaining cell survival in times of stress.

Considering the higher protein turnover and resultant ER stress that also occurs in cancer cells, the UBA5 enzyme is a target in disrupting cancer progression, by inhibiting the UFM1 conjugation pathway by sensitizing cancer cells to principal drugs responsible for inducing ER stress.[2,6] Furthermore, UFM1 conjugation is unique from other Ubl systems as it involves only one E1 (UBA5), one E2 (UFC1), and one E3 ligase (UFL1), compared to related pathways that rely on multiple E2s and up to hundreds of E3s.[3,4,7] Inhibition of UFM1 conjugation by targeting UBA5 upstream in the pathway could therefore be achieved without affecting off-target proteins.

Leishmaniasis is a flesh-eating disease that is widely spread through tropical and temporal climates, caused by infection of human hosts with protists of the genus *Leishmania*.[1] Infections are spread by the bite of the sand fly, and it is estimated that over 12 million people are afflicted with some form of Leishmaniasis, with 1-2 million new cases being reported worldwide annually.[8,9] Current treatments for Leishmaniasis include the use of anti-Malarial, anti-fungal, and strong anti-bacterial drugs, none of which specifically target the *Leishmania* parasites.[10]

The activating enzyme UBA5 is primarily responsible for organizing the attachment of a small label called UFM1 to target proteins in the cell. Recently, it was discovered that UFM1 labeling was also crucial to the survival of *Leishmania* parasites by a mitochondria-mediated mechanism, indicating inhibition of UBA5 will prevent UFM1 attachment to proteins leading to parasite-specific death.[13]

SUMMARY

The present disclosure relates to compounds of the Formula (I) which are, in one embodiment, UBA5 inhibitors.

In one embodiment, the compounds of the Formula (I) have the following structure

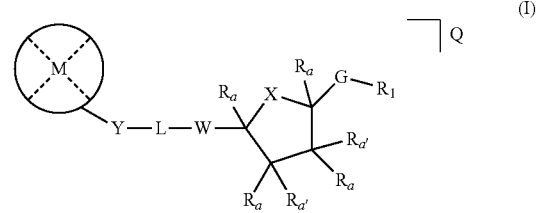

wherein

is a polyazamacrocycle chelating group, optionally having 2-6 coordination positions;

M is a chelatable metal ion;

Y is (i) —C(=O)—, or (ii) —C$_2$—;

L is (i) (C$_1$-C$_{20}$)-alkylene, wherein (i.a) at least one of the carbon atoms is optionally replaced with a heteroatom selected from O, NR' and S, wherein R' is H, (C$_1$-C$_6$)-alkyl or —C(=O)—(C$_1$-C$_6$)-alkyl;

(i.b) two or three adjacent carbon atoms are joined together to form (C$_3$-C$_{10}$)-cycloalkyl group or —(C$_6$-C$_{10}$)-aryl group; and/or (i.c) the (C$_1$-C$_{20}$)-alkylene group is optionally substituted with at least one halo;

(ii) $(C_2$-$C_{20})$-alkenylene, wherein
   (ii.a) at least one of the carbon atoms is optionally replaced with a heteroatom selected from O, NR' and S, wherein R' is H, $(C_1$-$C_6)$-alkyl or —C(=O)—$(C_1$-$C_6)$-alkyl;
   (ii.b) two or three adjacent carbon atoms are optionally joined together to form a $(C_3$-$C_{10})$-cycloalkyl group or —$(C_6$-$C_{10})$-aryl group; and/or
   (ii.c) the $(C_2$-$C_{20})$-alkenylene group is optionally substituted with at least one halo;
or
(iii) a polyethylene glycol (PEG) moiety;
W is
(i) —NH—C(=O)—;
(ii) —NR'—, wherein R' is H, $(C_1$-$C_6)$-alkyl or —C(=O)—$(C_1$-$C_6)$-alkyl
X is
(i) —O—;
(ii) NR', wherein R' is H, $(C_1$-$C_6)$-alkyl or —C(=O)—$(C_1$-$C_6)$-alkyl;
(iii) —S—; or —S(=O)$_2$—; or
(iv) —C(R")$_2$, wherein each R" is independently or simultaneously H, halo or $(C_1$-$C_6)$-alkyl;
$R_a$ and $R_{a'}$ are each independently or simultaneously
(i) H;
(ii) OH;
(iii) halo; or
(iv) $(C_1$-$C_3)$-alkyl; and
G is
(i) O;
(ii) S;
(iii) NR$_2$;
$R_1$ and $R_2$ are each independently or simultaneously
(i) H;
(ii) $(C_1$-$C_6)$-alkyl;
(iii) $(C_3$-$C_{10})$-cycloalkyl;
(iv) $(C_3$-$C_{10})$-heterocycloalkyl;
(v) —(CH$_2$)$_n$—$(C_6$-$C_{10})$-aryl;
(vi) —(CH$_2$)$_n$—$(C_5$-$C_{10})$-heteroaryl;
or
$R_1$ and $R_2$ are joined together to form a
(vii) guanine or a guanine derivative;
(viii) cytosine or a cytosine derivative;
(ix) thymine or a thymine derivative;
(x) adenine or an adenine derivative;
and Q is a suitable counteranion(s),
or a solvate, prodrug and/or stereoisomer thereof.

The present disclosure also includes pharmaceutical compositions comprising compounds of the Formula (I) and pharmaceutically acceptable excipients, carriers and/or additives.

In one embodiment, the compounds of the Formula (I) are inhibitors of the UBA5 enzyme. In another embodiment, the compounds of the Formula (I) are useful for treating or preventing conditions of a condition or disease mediated by the UBA5 enzyme. In another embodiment, the condition or disease is cancer, for example, leukemia, lung cancer or melanoma.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DRAWINGS

The disclosure will now be described in greater detail with reference to the following drawings in which.

Figure 4:
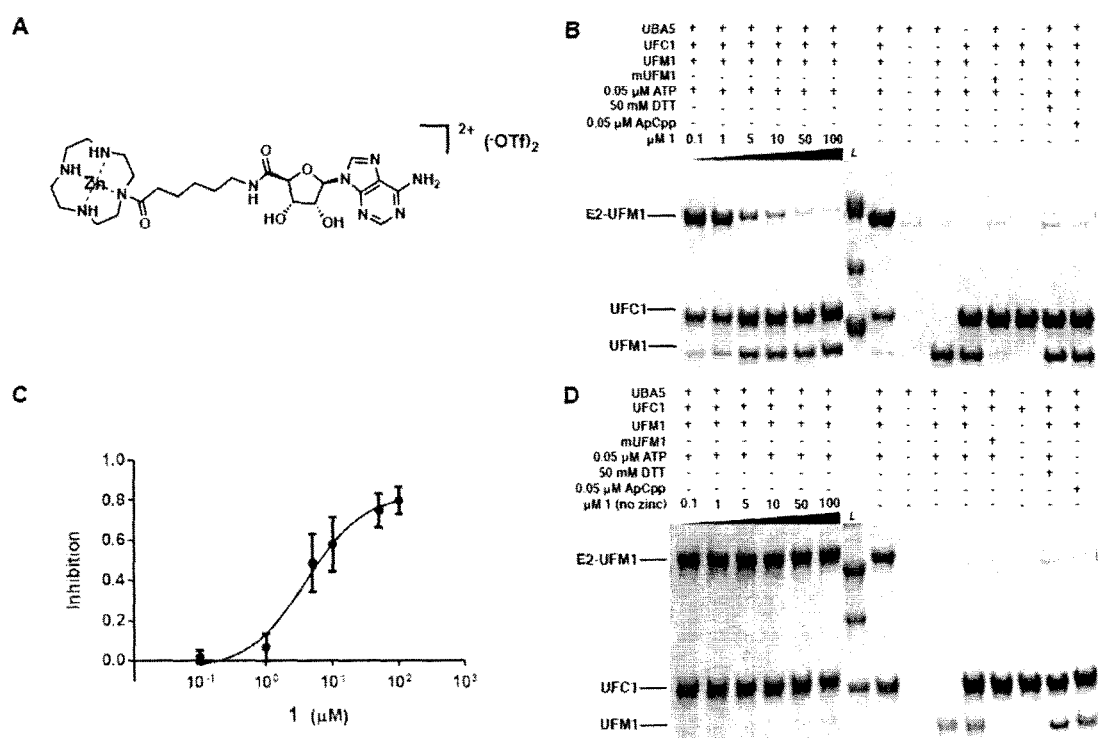
Figure 5:
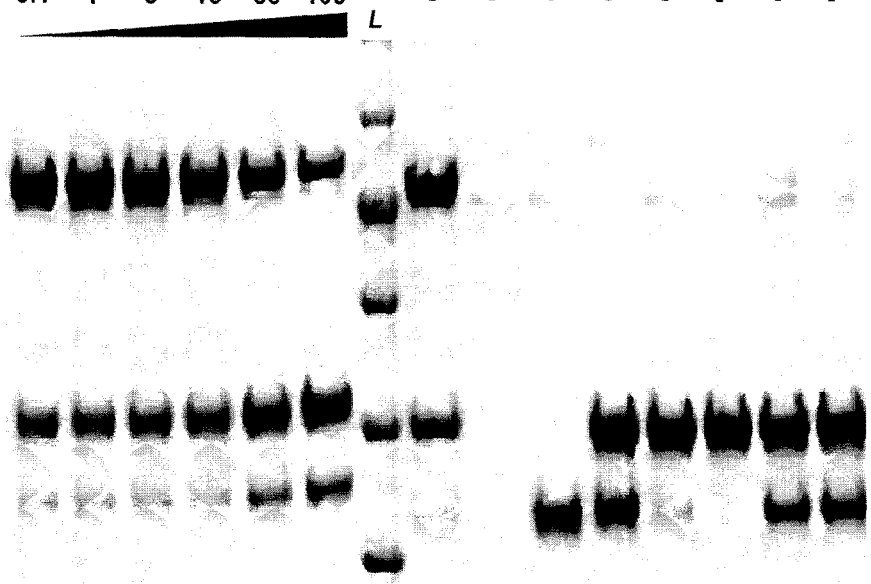
Figure 6:
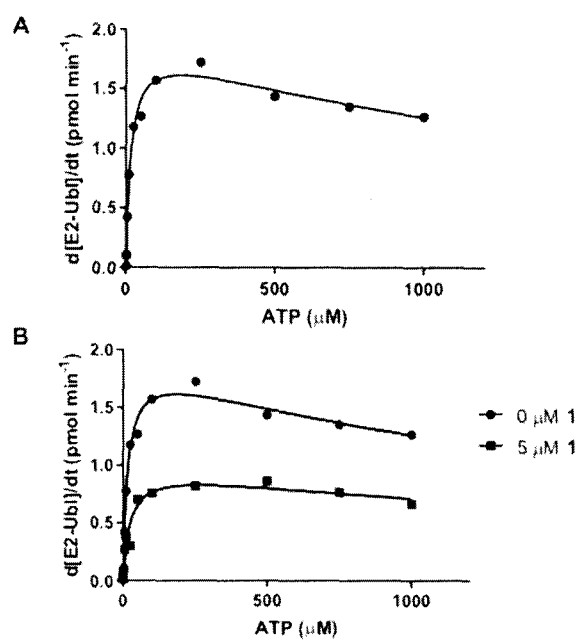
Figure 7:
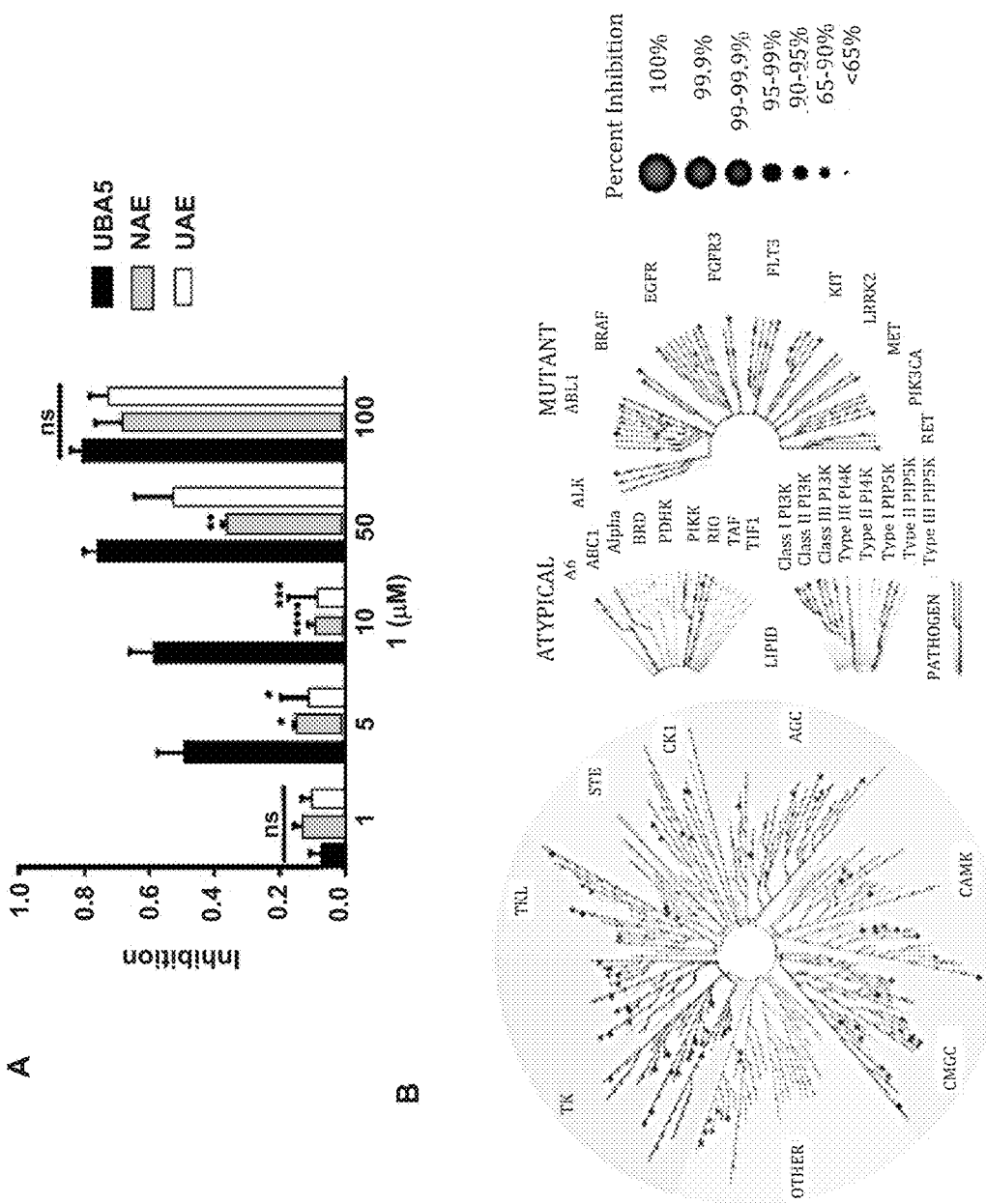
Figure 8:
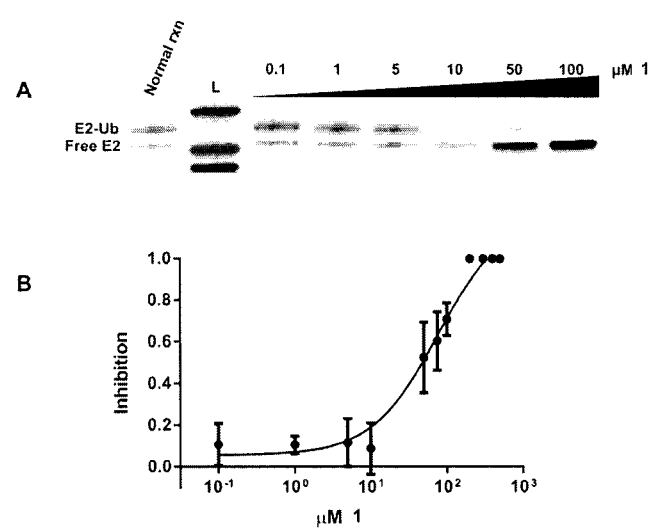
Figure 9:
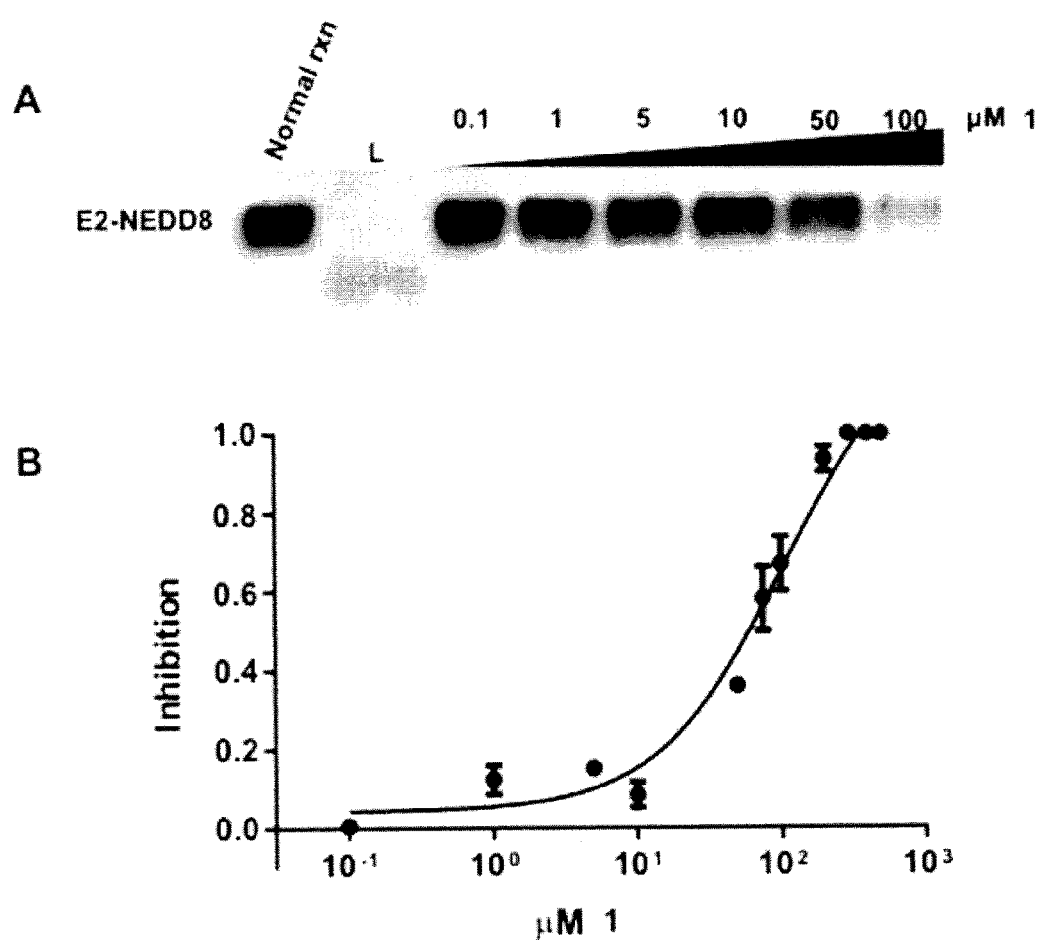
Figure 11:
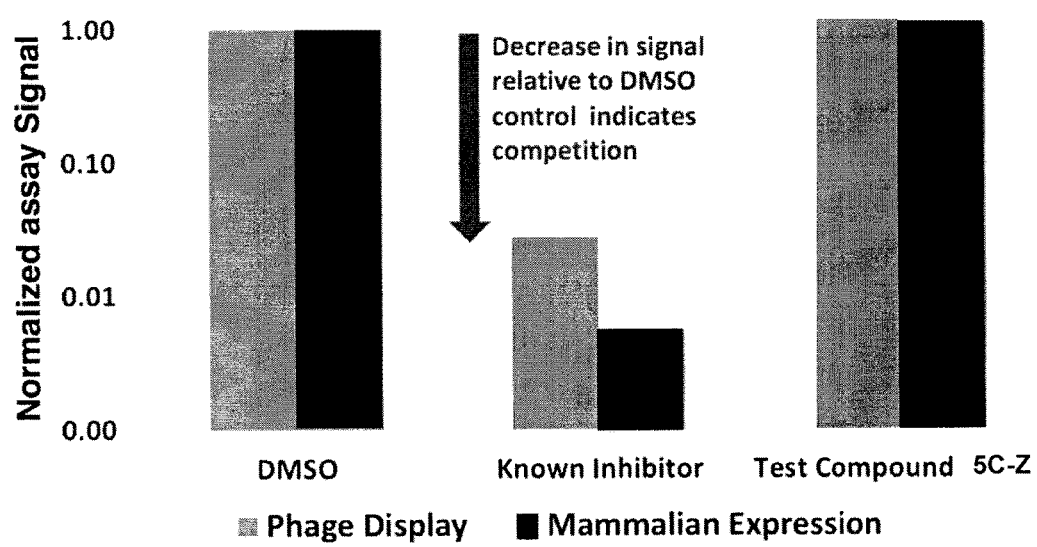
Figure 12:
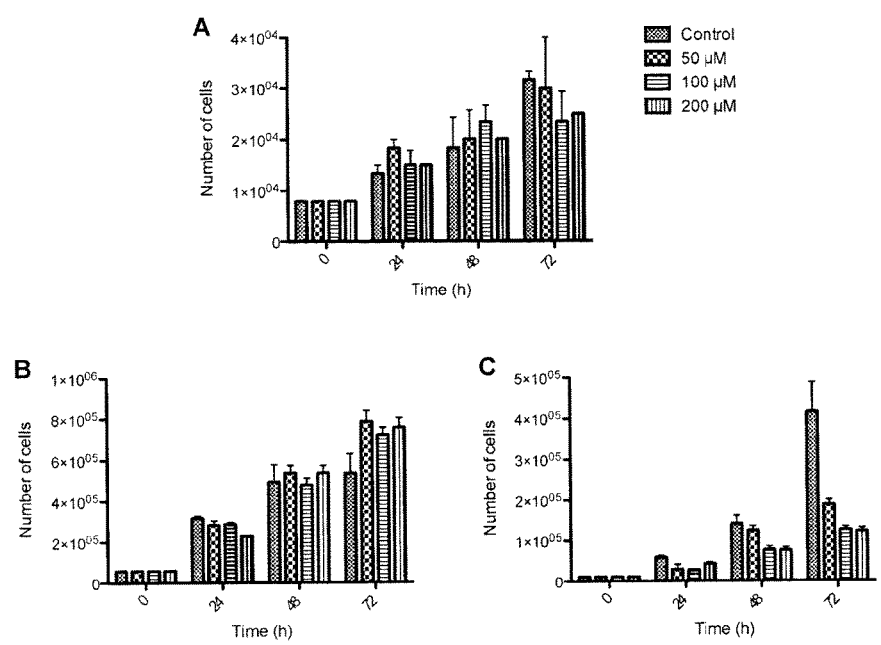
Figure 13:
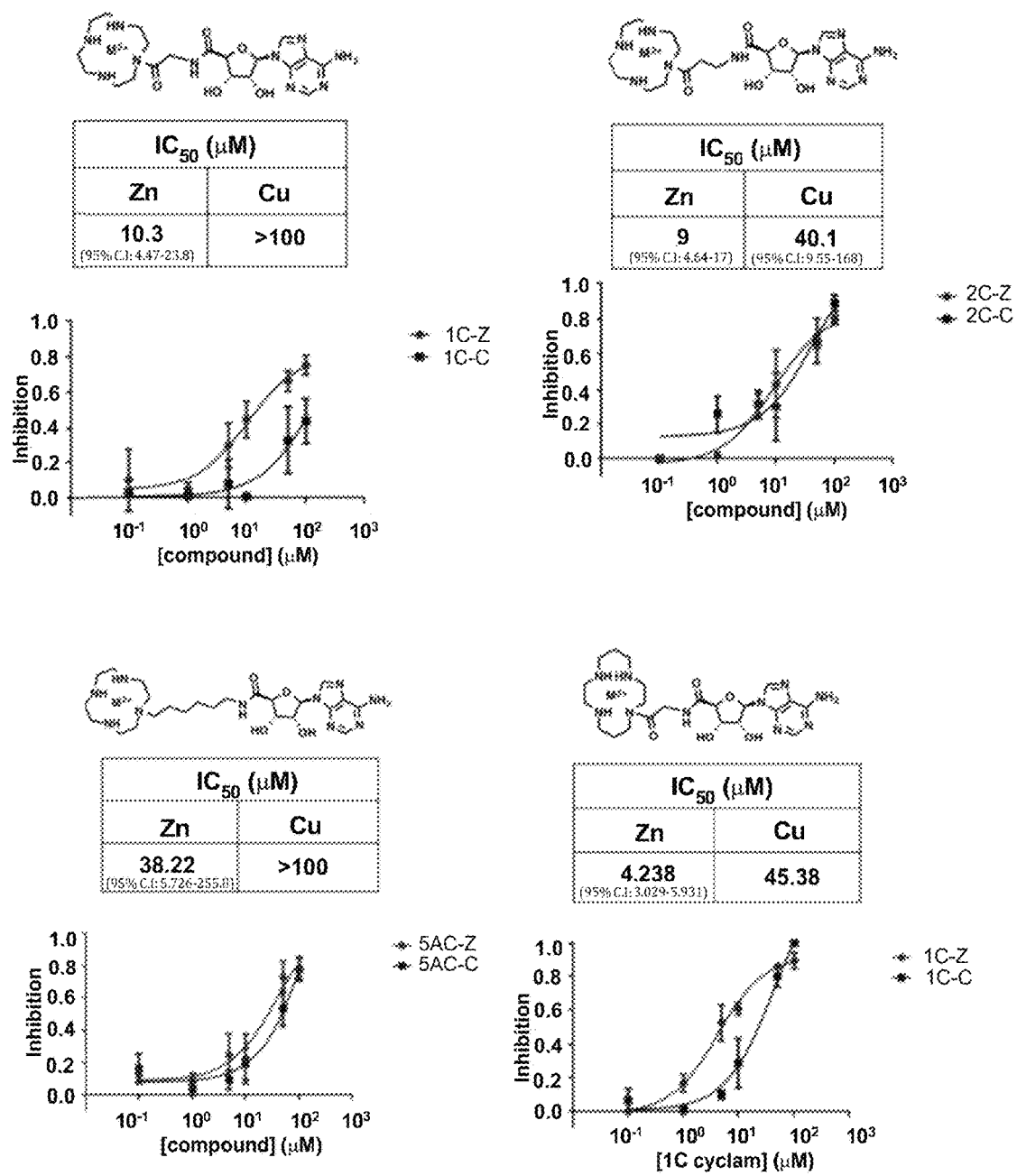
Figure 13:
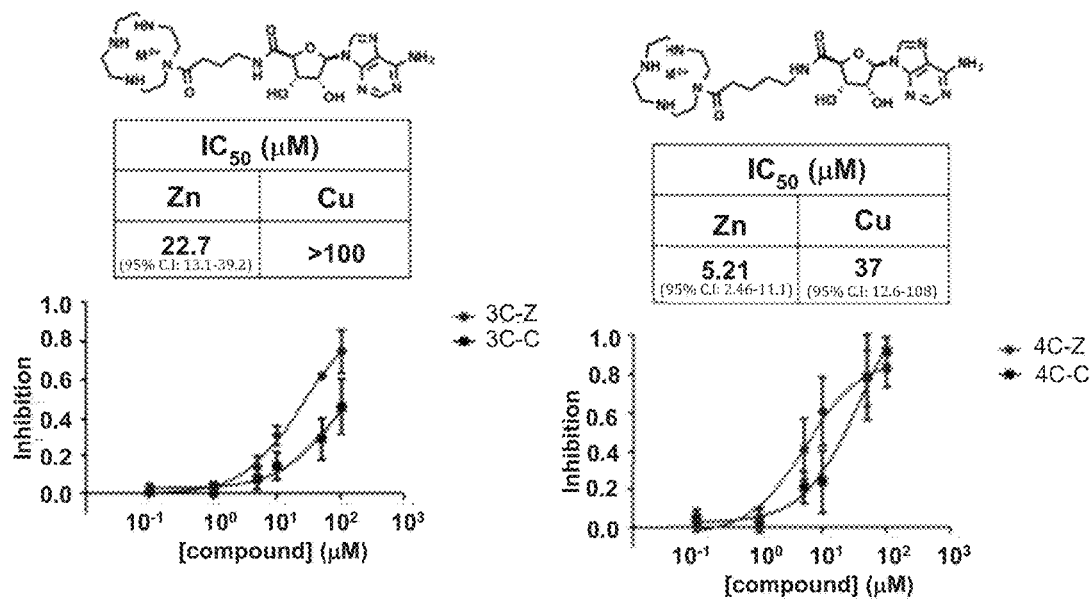

FIG. 4 shows the inhibition of UBA5 by a compound of the disclosure:
(A)—structure; (B) and (D)—Dose-dependent inhibition of UBA5 by the compound (without chelatable metal ion in (D)), as measured through the disappearance of the E2-UFM1 conjugate band and an increase in the intensity of the free UFC1 and UFM1 bands in a transthiolation assay; (C) Non-linear regression of the relative inhibition of UBA5;

FIG. 5 demonstrates the inhibitory activity against UBA5 of portions of the compounds of the disclosure;

FIG. 6 shows the kinetic analysis of UBA5 activity reveals substrate inhibition by ATP and non-competitive inhibition by a compound of the disclosure;

FIG. 7 shows the selectivity profile of a compound of the disclosure for UBA5 over other ATP-dependent enzymes;

FIG. 8 demonstrates the dose-dependent inhibition of the ubiquitin activating enzyme (UAE) by a compound of the disclosure;

FIG. 9 demonstrates the dose-dependent inhibition of the NEDD8 activating enzyme (NAE) by a compound of the disclosure;

FIG. 10 is a list of the complete kinase inhibition profile in the presence of a compound of the disclosure at 10 μM;

FIG. 11 illustrates that the presence of a zinc(II)cyclen moiety from a compound of the disclosure does not interfere with the kinome screen signal;

FIG. 12 shows the selective anti-proliferative activity was observed for Sk-Luci6 cancer cells (high UBA5 protein levels) compared with A549 carcinoma cells and MRC9 lung fibroblasts, which both express lower levels of UBA5 protein (ANOVA, n=3, p<0.001), when treated with increasing concentrations (uM) of a compound of the disclosure;

FIG. 13 shows the inhibition of UBA5 using compounds of the disclosure

Figure 14:
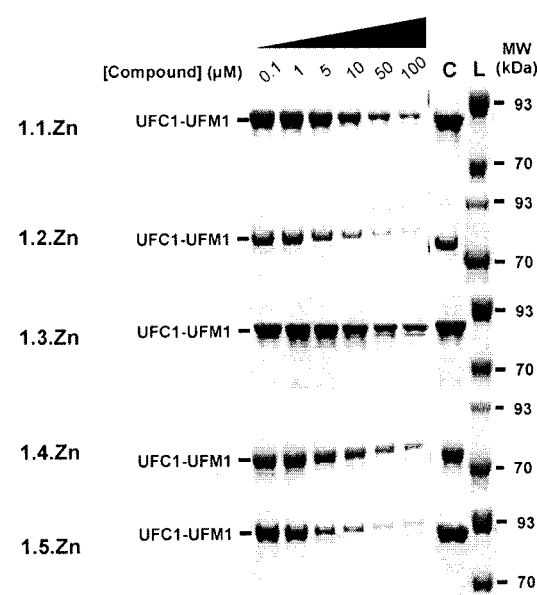
Figure 15:
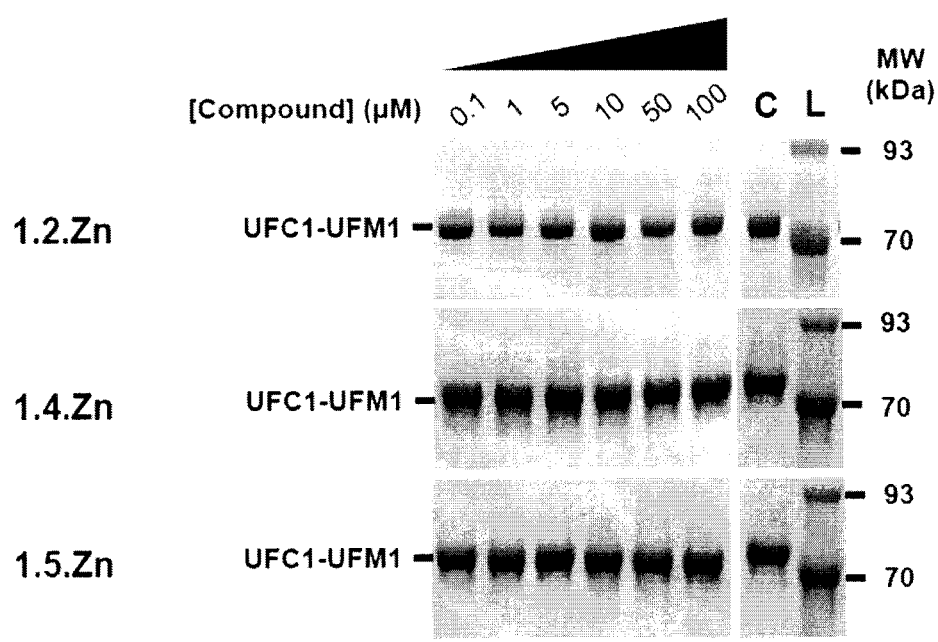
Figure 16:
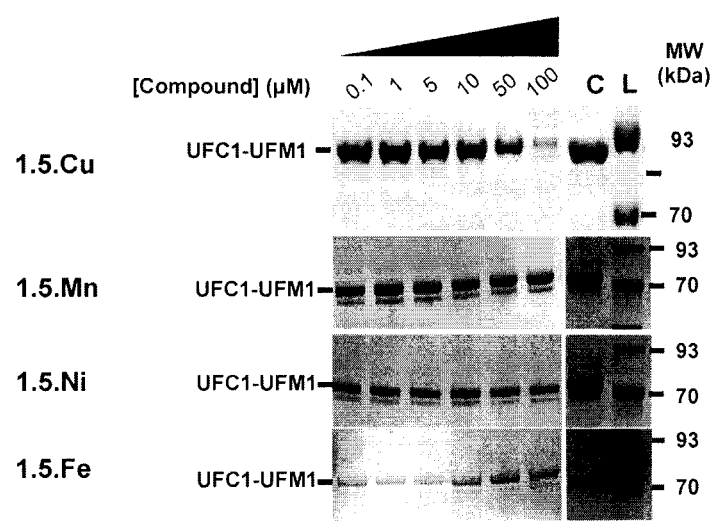
Figure 17:
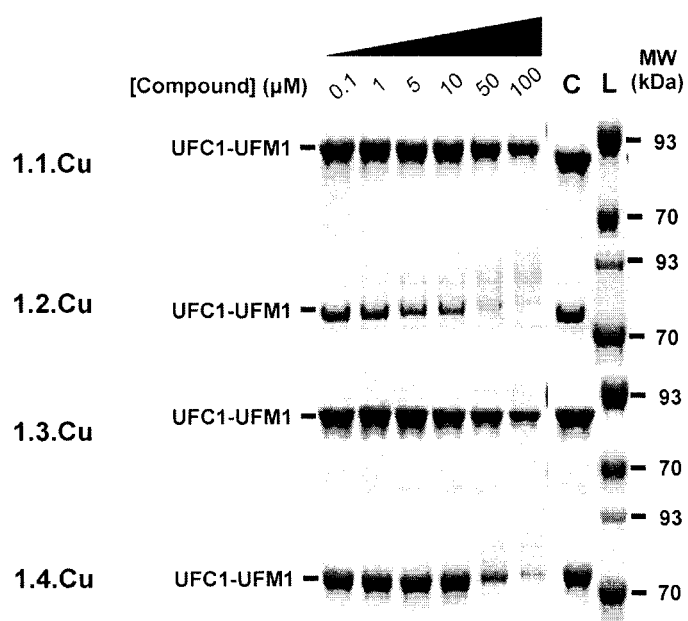
Figure 18:
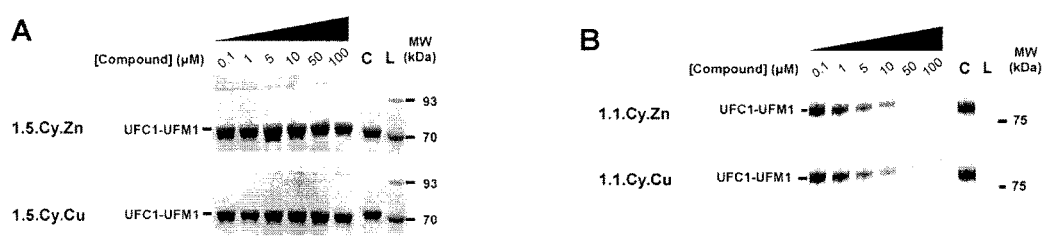
Figure 19:
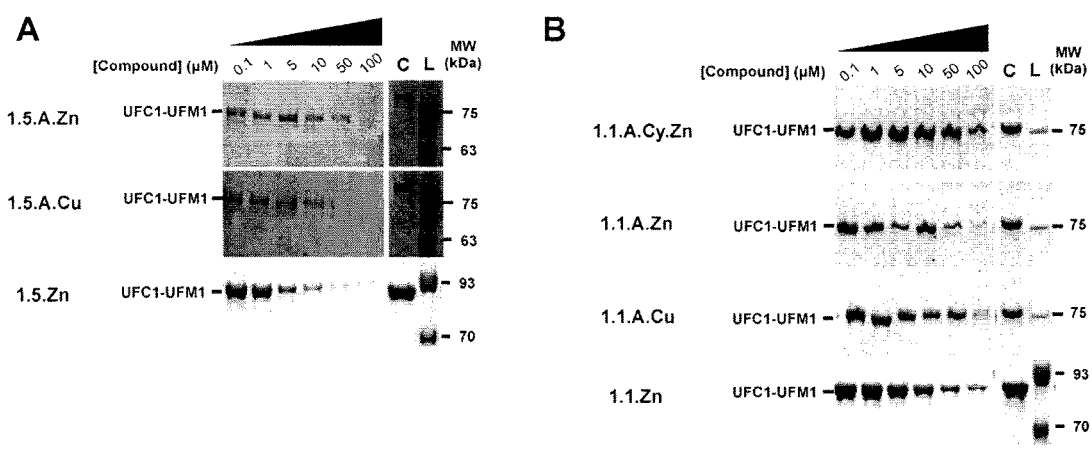
Figure 20:
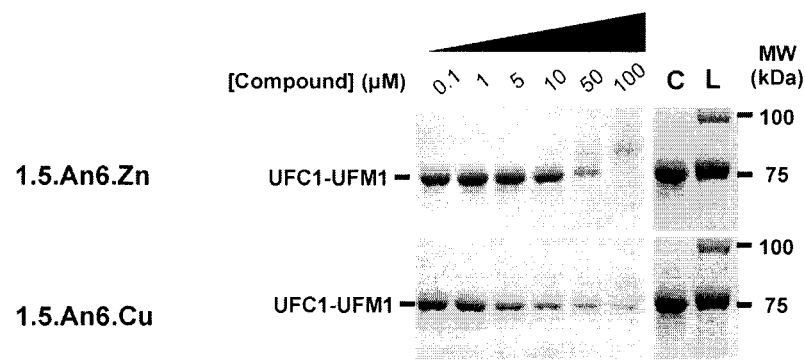
Figure 21:
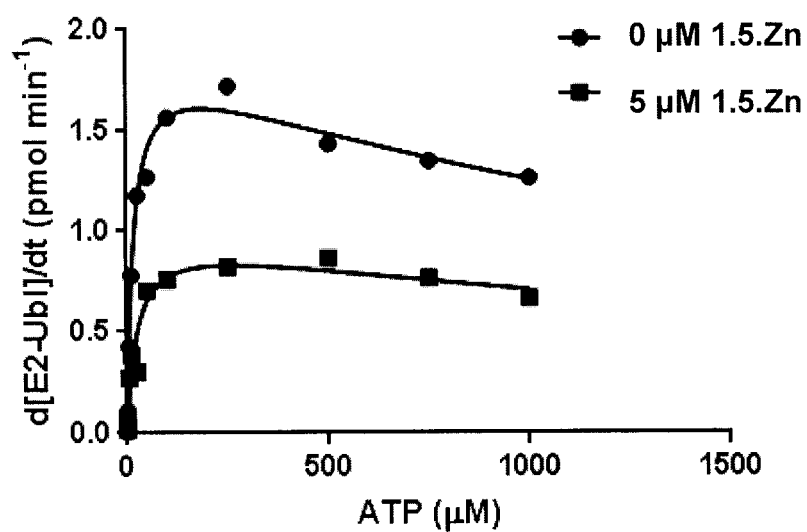
Figure 22:
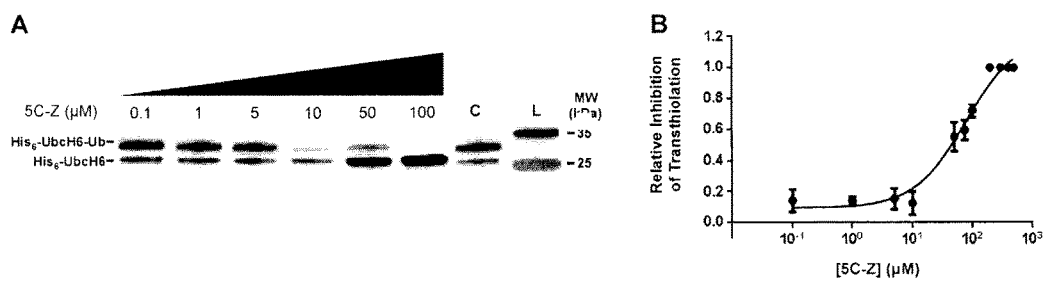
Figure 23:
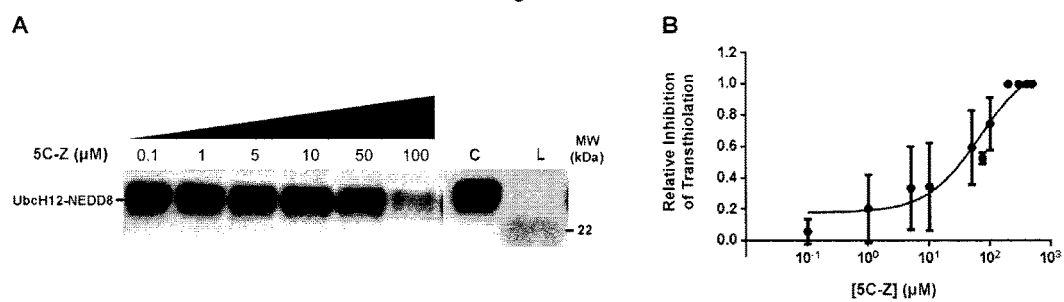
Figure 24:
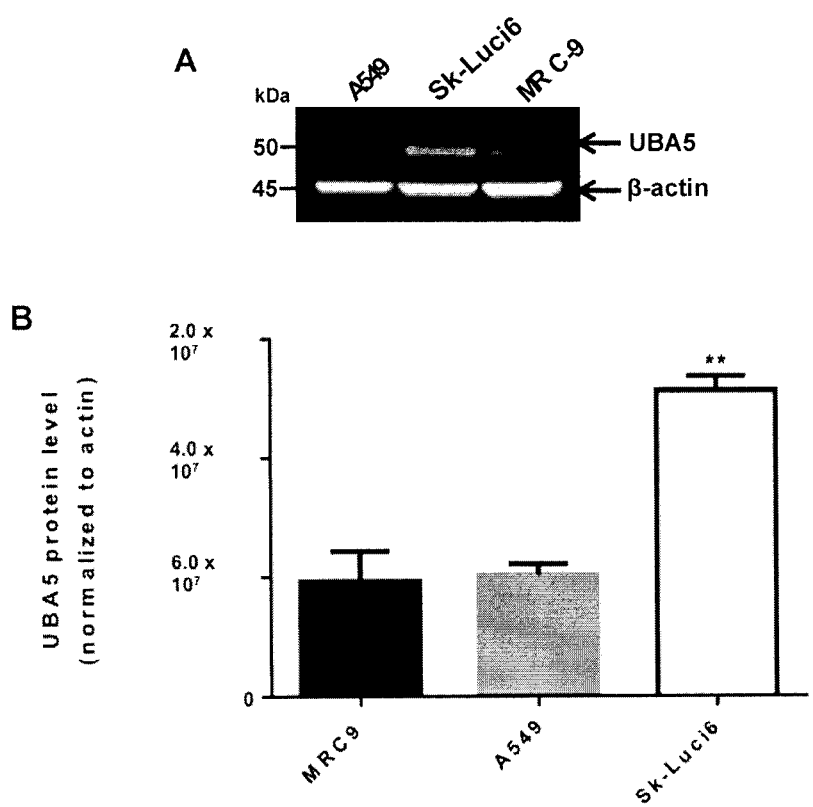
Figure 25:
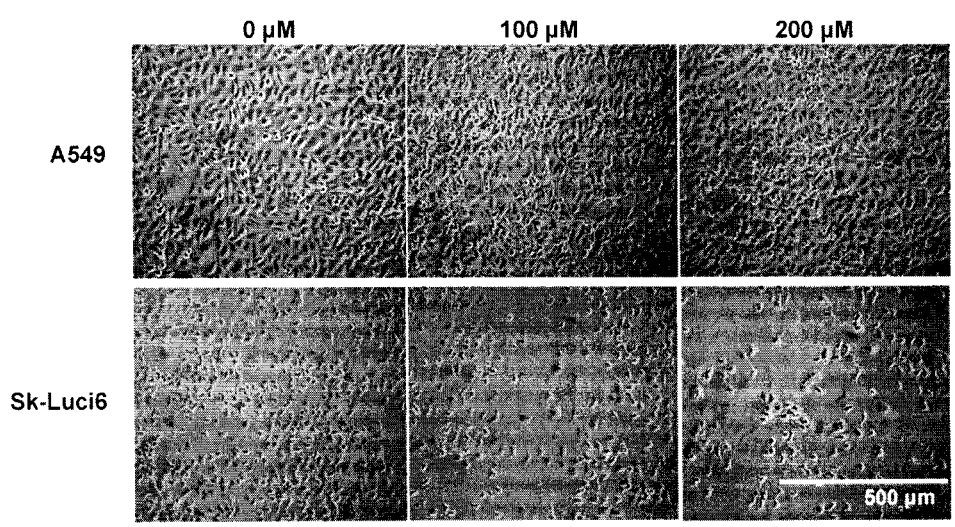
Figure 26:
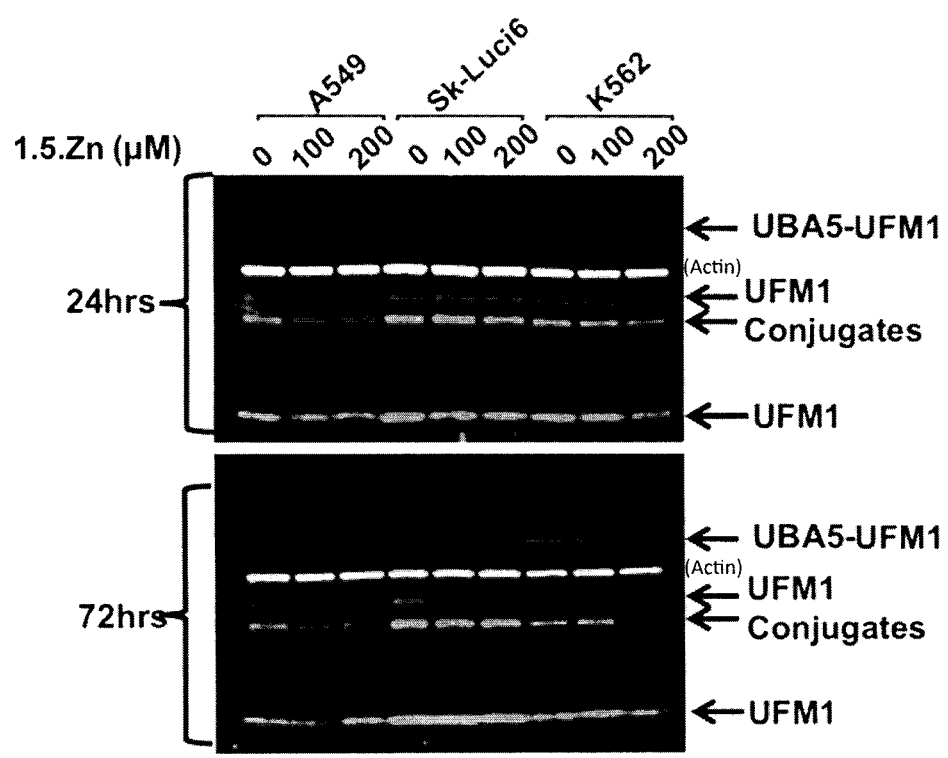
Figure 27:
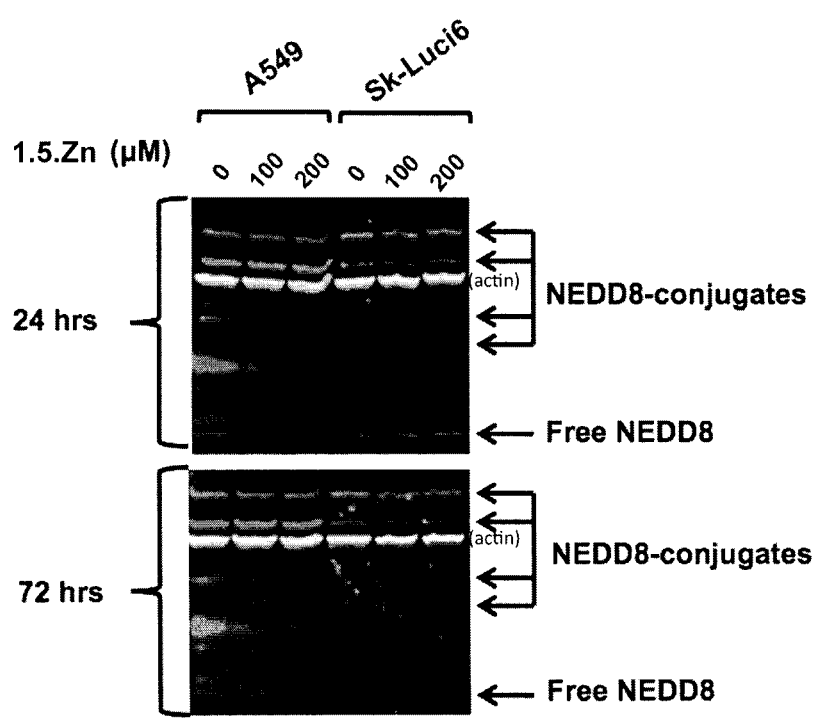

FIG. 14 shows the dose-dependent activity of compounds of the disclosure against GST-UBA5, as measured through the disappearance of the GST-UFC1/GST-UFM1 conjugate band in a transthiolation assay;

FIG. 15 shows the dose-dependent activity of more compounds of the disclosure ligands against GST-UBA5, as measured through the disappearance of the GST-UFC1/GST-UFM1 conjugate band in a transthiolation assay;

FIG. 16 shows the activity of compounds of the disclosure activity against GST-UBA5 up to a concentration of 100 μM in a transthiolation assay;

FIG. 17 shows the dose-dependent activity of other compounds of the disclosure against GST-UBA5, as measured through the disappearance of the GST-UFC1/GST-UFM1 conjugate band in a transthiolation assay;

FIG. 18 A. shows the activity of compounds of the disclosure against GST-UBA5 up to 100 μM, as measured through the disappearance of the GST-UFC1/GST-UFM1 conjugate band in a transthiolation assay. B. shows the activity of other compounds of the disclosure in a dose-dependent inhibition against UBA5 using the same transthiolation assay as described in A;

FIG. 19 A. shows the dose-dependent activity of more compounds of the disclosure against GST-UBA5, as measured through the disappearance of the GST-UFC1/GST-UFM1 conjugate band in a transthiolation assay. B. shows the dose-dependent activity of further compounds of the disclosure against GST-UBA5 in the transthiolation assay as described in A;

FIG. 20 shows the dose-dependent activity of more compounds of the disclosure against GST-UBA5, as measured through the disappearance of the GST-UFC1/GST-UFM1 conjugate band in a transthiolation assay;

FIG. 21 shows the kinetic profiling of the inhibition of transthiolation by a compound of the disclosure with respect to [ATP] (μM);

FIG. 22 (A) shows a dose-dependent inhibition of UAE by a compound of the disclosure, as measured through the disappearance of the $His_6$-UbcH6-Ub conjugate band in a transthiolation assay. (B) shows a Dose-response curve for the inhibition of Ub transthiolation from UAE to $His_6$-UbcH6 by a compound of the disclosure;

FIG. 23 (A) shows a dose-dependent inhibition of NAE by a compound of the disclosure, as measured through the disappearance of the UbcH12-NEDD8 conjugate band in a transthiolation assay. (B) shows a dose-response curve for the inhibition of NEDD8 transthiolation from NAE to UbcH12 by a compound of the disclosure;

FIG. 24 shows the differential UBA5 protein expression observed among the lung cell lines MRC9 (normal lung fibroblast), Sk-Luci6 (large cell anaplastic lung cancer), and A549 (adenocarcinomic human alveolar basal epithelial). (A) Western blot representation of the observed differences in protein levels across these cell lines. (B) Quantification of total UBA5 in these cell lines was determined through Western blot analysis using ImageLab software (n=3, **p<0.01);

FIG. 25 shows phase contrast images of the cell line-specific anti-proliferative effects of a compound of the disclosure (at 0, 100, and 200 μM);

FIG. 26 shows the relative UFMylation levels in A549 (UBA5 null), Sk-Luci6 (UBA5 high) and K562 (UBA5 high) were measured after dosing with a compound of the disclosure at different concentrations (μM) and lysing cells at 24 h or 72 h time points; and FIG. 27 shows NEDD8-conjugate formation with increasing concentrations of a compound of the disclosure (μM) in UBA5-null lung cancer cells (A549) and lung cancer cells expressing high levels of UBA5 (Sk-Luci6).

DESCRIPTION OF VARIOUS EMBODIMENTS

The term "$(C_1-C_p)$_alkyl" as used herein means straight and/or branched chain, saturated alkyl moieties containing from one to "p" carbon atoms and includes (depending on the identity of p) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical.

The term "$(C_2-C_p)$_alkenyl" as used herein means straight and/or branched chain, unsaturated alkyl moieties containing from one to "p" carbon atoms and includes at least one carbon-carbon double bond and includes (depending on the identity of p) ethenyl, 1-propenyl, isopropenyl, 1-butenyl, 2-butenyl, t-butenyl, 1-pentenyl, 2-methyl-1-pentenyl, 3-methyl-1-pentenyl, 4-methyl-1-pentenyl, 1-hexenyl, 2-hexenyl and the like, where the variable p is an integer representing the largest number of carbon atoms in the alkenyl radical.

The term "$C_{3-p}$cycloalkyl" as used herein means a monocyclic, bicyclic or tricyclic saturated carbocylic group containing from three to "p'" carbon atoms and includes (depending on the identity of p) cyclopropyl, cyclobutyl, cyclopentyl, cyclodecyl and the like, where the variable p' is an integer representing the largest number of carbon atoms in the cycloalkyl radical. The term cycloalkyl also includes all of the fully saturated and partially unsaturated derivatives of the below-mentioned aryl groups The term "heteroaryl" as used herein refers to aromatic cyclic or polycyclic ring systems having at least one heteroatom chosen from N, O and S and at least one aromatic ring. Examples of heteroaryl groups include, without limitation, furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl and quinazolinyl, among others.

The term "heterocyclyl" as used herein includes non-aromatic rings or ring systems that contain at least one ring having at least one heteroatom (such as nitrogen, oxygen or sulfur). For example, the heterocyclyl groups include all of the fully saturated and partially unsaturated derivatives of the above-mentioned heteroaryl groups. Examples of heterocyclic groups include, without limitation, pyrrolidinyl, tetrahydrofuranyl, morpholinyl, thiomorpholinyl, piperidinyl, piperazinyl, thiazolidinyl, isothiazolidinyl, and imidazolidinyl.

The term "aryl" as used herein refers to cyclic groups that contain at least one aromatic ring, for example a single ring (e.g. phenyl) or multiple condensed rings (e.g. naphthyl). In an embodiment of the present disclosure, the aryl group contains 6, 9 or 10 atoms such as phenyl, naphthyl, anthracenyl, 1,2-dihydronaphthyl, 1,2,3,4-tetrahydronaphthyl, fluorenyl, indanyl, indenyl and the like The suffix "ene" added on to any of the above groups means that the group is divalent, i.e. inserted between two other groups.

The term "halo" as used herein refers to a halogen atom and includes fluorine (F), chlorine (Cl), bromine (Br) and iodine (I).

The term "polyazamacrocycle chelating group" as used herein refers to a macrocycle containing least 8 atoms, at least two of which are nitrogen atoms (optionally 3, 4, 5 or 6 nitrogen atoms), and which is able to chelate a metal ion. The polyazamacrocycle chelating group may also have carboxylic acid substituents, such as ethanoic substituents, bonded to the nitrogen atoms.

The term "chelatable metal ion" as used herein refers to any metal ion which chelates to the polyazamacrocycle chelating group. Examples of chelatable metal ions include, but are not limited to, ions of transition metals, ions of lanthanides, and include, for example, zinc ions, copper ions, iron ions, nickel ions, manganese ions, cobalt ions, palladium ions, gadolinium ions, terbium ions, europium ions, and molybdenum ions.

The term "counteranion," as used herein, refers to an atom(s) or group(s) having a formal negative charge that is/are present to balance the charge of a chelatable metal ion.

The term "derivative" as used herein refers to a compound, group or moiety which comprises the same basic carbon skeleton and functionality as the parent, but can also bear one or more substituents or substitutions of the parent compound, group or moiety. For example, nucleoside derivatives (guanine, cytosine, thymine or adenine), include amino substitutions, alkyl amine substitutions, heterocyclic substitutions, aryl or heteroaryl substitutions.

The term "pharmaceutically acceptable salt" refers, for example, to a salt that retains the desired biological activity of a compound of the present disclosure and does not impart undesired toxicological effects thereto; and may refer to an acid addition salt or a base addition salt.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

In embodiments of the present disclosure, the compounds may have an asymmetric center. These compounds exist as enantiomers. Where compounds possess more than one asymmetric center, they may exist as diastereomers. It is to be understood that all such isomers and mixtures thereof in any proportion are encompassed within the scope of the present disclosure. It is to be further understood that while the stereochemistry of the compounds may be as shown in any given compound listed herein, such compounds may also contain certain amounts (e.g. less than 20%, suitably less than 10%, more suitably less than 5%) of compounds of the disclosure having alternate stereochemistry. For example, compounds of the disclosure that are shown without any stereochemical designations are understood to be racemic mixtures (i.e. contain an equal amount of each possible enantiomer or diastereomer). However, it is to be understood that all enantiomers and diastereomers are included within the scope of the present disclosure, including mixtures thereof in any proportion.

The term "effective amount" or "therapeutically effective amount" or "pharmaceutically effective amount" as used herein means an amount effective, at dosages and for periods of time necessary to achieve the desired result. For example in the context of treating a subject with a disease mediated by UBA5, an effective amount is an amount that, for example, inhibits the UBA5 enzyme in the subject. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

As used herein, the term "prodrug" refers to a substance that is prepared in an inactive form that is converted to an active form (i.e., drug) within the body or cells thereof by the action of, for example, endogenous enzymes or other chemicals and/or conditions. Prodrug derivatives of the compounds of Formula (I) or pharmaceutically acceptable salts or solvates thereof, can be prepared by methods known to those of ordinary skill in the art, and include esters of any free hydroxyl or carboxyl moieties of the compounds.

As used herein, a "subject" refers to all members of the animal kingdom including mammals, and suitably refers to humans. A member of the animal kingdom includes, without limitation, a mammal (such as a human, primate, swine, sheep, cow, equine, horse, camel, canine, dog, feline, cat, tiger, leopard, civet, mink, stone marten, ferret, house pet, livestock, rabbit, mouse, rat, guinea pig or other rodent, seal, whale and the like), fish, amphibian, reptile, and bird (such as water fowl, migratory bird, quail, duck, goose, poultry, or chicken). In an embodiment of the present disclosure, the subject is in need of a compound or composition of the disclosure.

Compounds of the Disclosure

The present disclosure relates to compounds of the Formula (I) which contain a metal chelating moiety. In one embodiment, when bound to a chelatable metal ion, the compounds are UBA5 inhibitors.

In one embodiment of the disclosure, there is included a compound of the Formula (I)

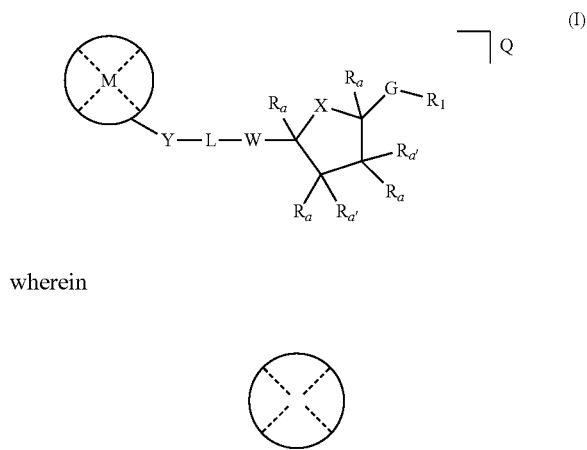

wherein is a polyazamacrocycle chelating group;

M is a chelatable metal ion;

Y is (i) —C(=O)—, or (ii) —CH$_2$—;

L is (i) (C$_1$-C$_{20}$)-alkylene, wherein
   (i.a) at least one of the carbon atoms is optionally replaced with a heteroatom selected from O, NR' and S, wherein R' is H, (C$_1$-C$_6$)-alkyl or —C(=O)—(C$_1$-C$_6$)-alkyl;
   (i.b) two or three adjacent carbon atoms are joined together to form a (C$_3$-C$_{10}$)-cycloalkyl group or —(C$_6$-C$_{10}$)-aryl group; and/or
   (i.c) the (C$_1$-C$_{20}$)-alkylene group is optionally substituted with at least one halo;

(ii) (C$_2$-C$_{20}$)-alkenylene, wherein
   (ii.a) at least one of the carbon atoms is optionally replaced with a heteroatom selected from O, NR' and S, wherein R' is H, (C$_1$-C$_6$)-alkyl or —C(=O)—(C$_1$-C$_6$)-alkyl;
   (ii.b) two or three adjacent carbon atoms are optionally joined together to form a (C$_3$-C$_{10}$)-cycloalkyl group or —(C$_6$-C$_{10}$)-aryl group; and/or
   (ii.c) the (C$_2$-C$_{20}$)-alkenylene group is optionally substituted with at least one halo;

or (iii) a polyethylene glycol (PEG) moiety;

W is
(i) —NH—C(=O)—;
(ii) —NR'—, wherein R' is H, $(C_1-C_6)$-alkyl or —C(=O)—$(C_1-C_6)$-alkyl
X is
(i) —O—;
(ii) NR', wherein R' is H, $(C_1-C_6)$-alkyl or —C(=O)—$(C_1-C_6)$-alkyl;
(iii) —S—; or —S(=O)$_2$—; or
(iv) —C(R")$_2$, wherein each R" is independently or simultaneously H, halo or $(C_1-C_6)$-alkyl;
$R_a$ and $R_{a'}$ are each independently or simultaneously
(i) H;
(ii) OH;
(iii) halo; or
(iv) $(C_1-C_3)$-alkyl; and
G is
(i) O;
(ii) S;
(iii) NR$_2$;
$R_1$ and $R_2$ (if $R_2$ is present) are each independently or simultaneously
(i) H;
(ii) $(C_1-C_6)$-alkyl;
(iii) $(C_3-C_{10})$-cycloalkyl;
(iv) $(C_3-C_{10})$-heterocycloalkyl;
(v) —(CH$_2$)$_n$—$(C_6-C_{10})$-aryl;
(vi) —(CH$_2$)$_n$—$(C_5-C_{10})$-heteroaryl; or
$R_1$ and $R_2$ are joined together to form a
(vii) guanine or a guanine derivative;
(viii) cytosine or a cytosine derivative;
(ix) thymine or a thymine derivative;
(x) adenine or an adenine derivative;
and wherein Q is a suitable counteranion(s), or a solvate, prodrug and/or stereoisomer thereof.

In another embodiment, the polyazamacrocycle chelating group has the following structure

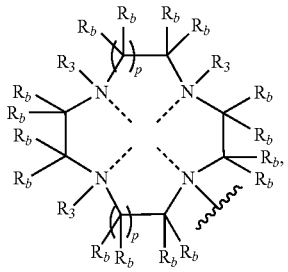

wherein
each $R_3$ is independently or simultaneously
(i) H; or
(ii) $(C_1-C_3)$-alkyl;
each $R_b$ is independently or simultaneously
(i) H;
(ii) $(C_1-C_3)$-alkyl; or
(iii) CF$_3$; and
p is 1 or 2.

In another embodiment, the polyazamacrocycle chelating group has the following structure

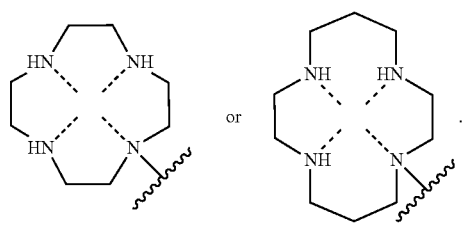

In one embodiment, the polyazamacrocycle chelating group has the following structure

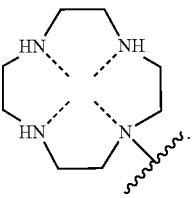

In another embodiment, the chelatable metal ion is any metal ion which upon chelation with the polyazamacrocycle results in a UBA5 inhibitor. Examples of chelatable metal ions include, but are not limited to, ions of transition metals, ions of lanthanides, and include, for example, zinc ions, copper ions, iron ions, nickel ions, manganese ions, cobalt ions, palladium ions, gadolinium ions, terbium ions, europium ions, and molybdenum ions. In one embodiment, the chelatable metal ion is $Zn^{2+}$, $Cu^{2+}$, $Fe^{2+}$, $Ni^{2+}$, $Mn^{2+}$, $Co^{2+}$, $Pd^{2+}$, $Gd^{2+}$, $Tb^{2+}$, $Eu^{2+}$ or $Mo^{2+}$. In one embodiment, the chelatable metal ion is $Zn^{2+}$, $Cu^{2+}$, $Co^{2+}$, $Pd^{2+}$, $Gd^{2+}$, $Tb^{2+}$, $Eu^{2+}$ or $Mo^{2+}$. In one embodiment, M is $Zn^{2+}$ or $Cu^{2+}$. In one embodiment, M is $Zn^{2+}$.

In another embodiment, the polyazamacrocycle and metal ion have the following structure

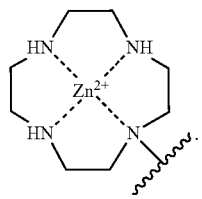

In another embodiment, the compounds of the Formula (I) comprise suitable counteranions as the opposite charge to the metal ion. In one embodiment, the counteranion is a mono-anion, such as a halo, triflate, mesylate, borates, and perchlorate, or a di-anion, such as an oxalate.

In another embodiment of the disclosure, Y is —C(=O)—. In another embodiment, Y is —CH$_2$—.

In a further embodiment, L is $(C_1-C_{10})$-alkylene or $(C_2-C_{10})$-alkenylene, wherein (i) one to five carbon atoms are optionally replaced with a heteroatom selected from O, NR' and S, wherein R' is H, $(C_1-C_6)$-alkyl or —C(=O)—$(C_1-C_6)$-alkyl; (ii) two or three adjacent carbon atoms are joined together to form a $(C_5-C_7)$-cycloalkyl group or —$(C_6)$-aryl group; and/or (iii) the $(C_1-C_{10})$-alkylene or $(C_2-C_{10})$-alkenylene is optionally substituted with at least one fluoro. In another embodiment, L is $(C_1-C_6)$-alkylene or $(C_2-C_6)$-alkenylene, wherein (i) one to three carbon atoms are optionally replaced with a heteroatom selected from O, NR' and S, wherein R' is H, $(C_1-C_3)$-alkyl or $-C(=O)-(C_1-C_3)$-alkyl; (ii) two or three adjacent carbon atoms are joined together to form a cyclohexyl group or a phenyl group; and/or (iii) the $(C_1-C_6)$-alkylene or $(C_2-C_6)$-alkenylene is optionally substituted with at least one fluoro. In an embodiment, L is $(C_1-C_6)$-alkylene or $(C_2-C_6)$-alkenylene, optionally $(C_3-C_6)$-alkylene, or optionally, methylene, ethylene, propylene, butylene, pentylene or hexylene.

In a further embodiment, L is a polyethylene glycol (PEG) moiety, wherein the PEG represents oligomer or polymer chains of the basic unit $H-(O-CH_2-CH_2)_n-OH$.

In one embodiment, L is $(CH_2)_1$, $(CH_2)_2$, $(CH_2)_3$, $(CH_2)_4$, $(CH_2)_5$, $(CH_2)_6$, $(CH_2)_7$, $(CH_2)_8$, $(CH_2)_9$, $(CH_2)_{10}$, or is a polyethylene glycol (PEG) moiety, wherein the PEG represents oligomer or polymer chains of the basic unit $H-(O-CH_2-CH_2)_n-OH$.

In an embodiment, W is $-NH-C(=O)-$.

In another embodiment, W is $-NR'-$, wherein R' is H, $(C_1-C_6)$-alkyl or $-C(=O)-(C_1-C_6)$-alkyl. In another embodiment, W is $-NR'-$, wherein R' is H, $(C_1-C_3)$-alkyl or $-C(=O)-(C_1-C_3)$-alkyl.

In another embodiment of the disclosure, X is $-O-$.

In an embodiment, $R_a$ and $R_{a'}$ are each independently or simultaneously H, OH or F. In a further embodiment, $R_a$ is OH and $R_{a'}$ is H.

In another embodiment of the disclosure, the moiety

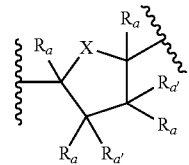

has the following structure

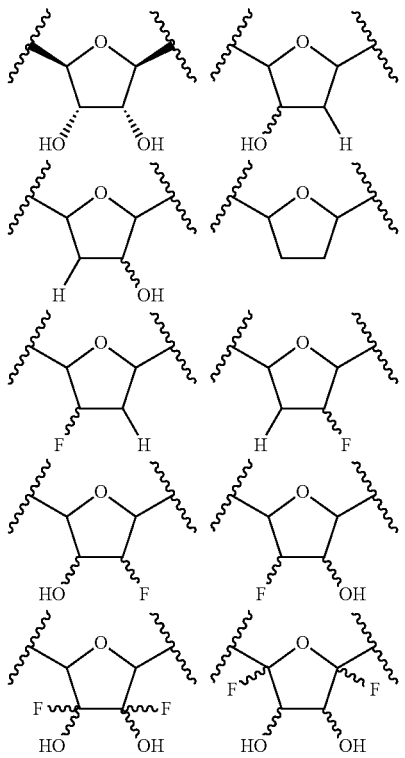

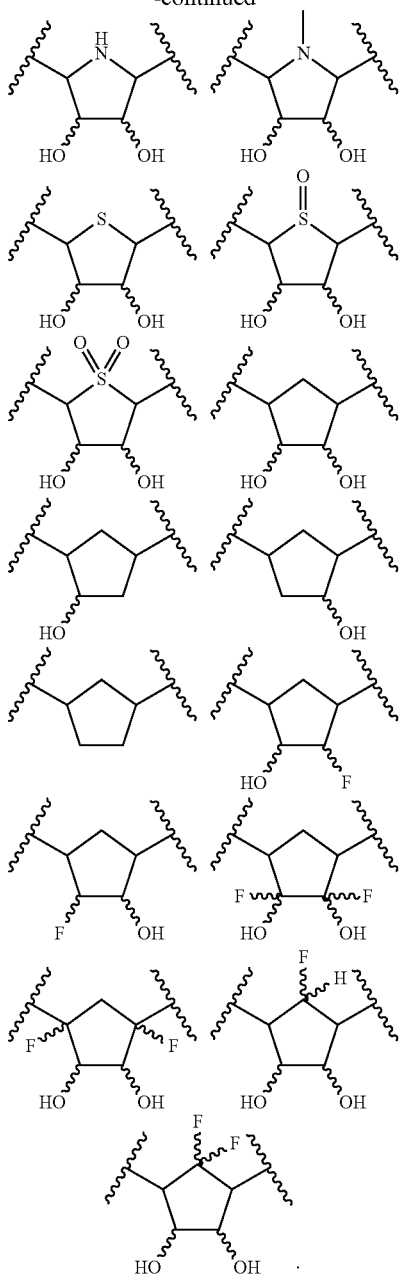

In a further embodiment, the structure is

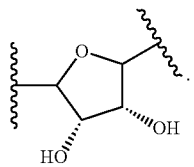 [SMILES: *C1OC(*)[C@H](O)[C@@H]1O]

In another embodiment, $R_1$ and $R_2$ are each independently or simultaneously
(i) H;
(ii) $(C_5-C_7)$-cycloalkyl;
(iii) $(C_5-C_7)$-heterocycloalkyl;
(iv) phenyl or $-(CH_2)$-phenyl;

(v) naphthyl or —(CH$_2$)-naphthyl;
(vi) —(CH$_2$)$_n$—(C$_5$-C$_6$)-heteroaryl;
or
R$_1$ and R$_2$ are joined together to form a
(vii) guanine or a guanine derivative;
(viii) cytosine or a cytosine derivative;
(ix) thymine or a thymine derivative; or
(x) adenine or an adenine derivative.

In a further embodiment, R$_1$ and R$_2$ are each independently or simultaneously
(I) H;
(ii) cyclopentyl or cyclohexyl;
(iii) morpholinyl or piperazinyl;
(iv) phenyl or —(CH$_2$)-phenyl;
(v) naphthyl or —(CH$_2$)-naphthyl;
(vi) pyridinyl or —CH$_2$-pyridinyl;
or
R$_1$ and R$_2$ are joined together to form a
(vii) guanine or a guanine derivative;
(viii) cytosine or a cytosine derivative;
(ix) thymine or a thymine derivative; or
(x) adenine or an adenine derivative.

In a further embodiment, R$_1$ and R$_2$ are joined to form guanine or a guanine derivative; cytosine or a cytosine derivative; thymine or a thymine derivative; or adenine or an adenine derivative. In one embodiment, R$_1$ and R$_2$ are joined together to form adenine or an adenine derivative. In another embodiment, R$_1$ and R$_2$ are joined together to form adenine. In another embodiment, R$_1$ and R$_2$ are joined to form an adenine derivative having the structure

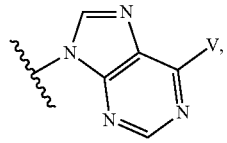

wherein

V is H, OH, halo, (C$_1$-C$_6$)-alkyl, (C$_6$-C$_{10}$)-aryl, (C$_5$-C$_{10}$)-heteroaryl, —NH—(C$_6$-C$_{10}$)-aryl, (C$_3$-C$_{10}$)-cycloalkyl, or (C$_3$-C$_{10}$)-heterocycloalkyl, the latter five groups being optionally substituted with —N(R')$_2$, wherein R' is H or (C$_1$-C$_3$)-alkyl.

In another embodiment, the adenine derivative has the following structure

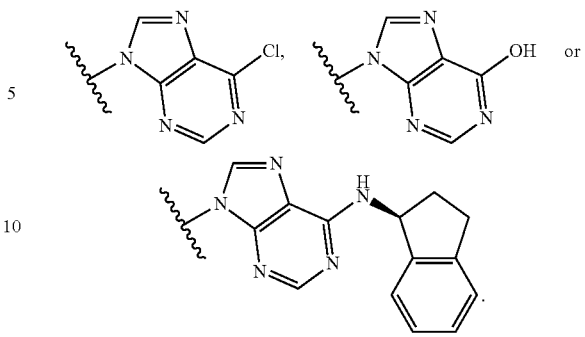

In another embodiment, the compound of the Formula (I) has the structure

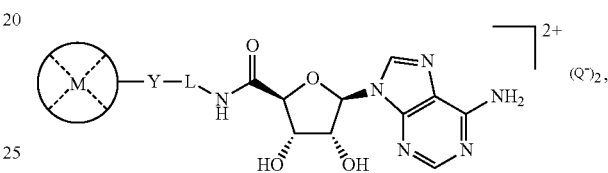

wherein

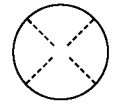

is a polyazamacrocycle chelating group;
M is a chelatable metal ion;
Y is —C(=O)— or —CH$_2$—; and
L is (C$_1$-C$_{10}$)-alkylene or a polyethylene glycol (PEG) moiety.

In another embodiment, the compound of the Formula (I) has the structure

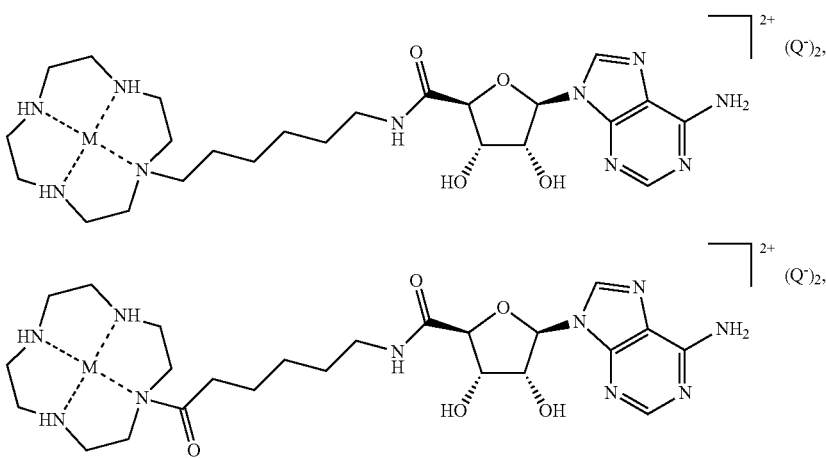

-continued

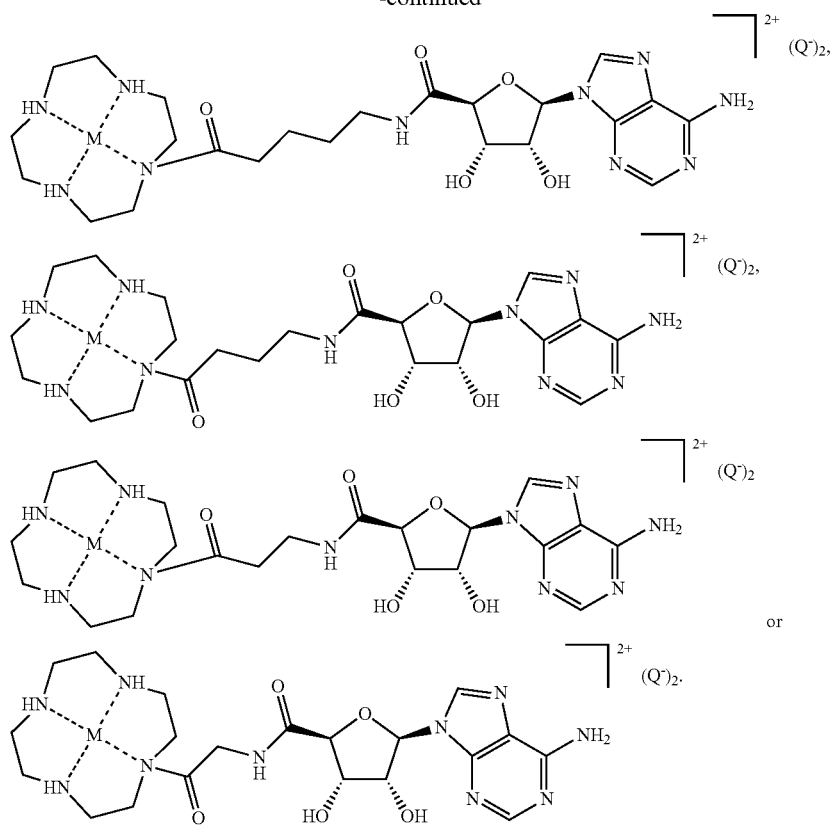

In another embodiment, the compound of the Formula (I) has the structure

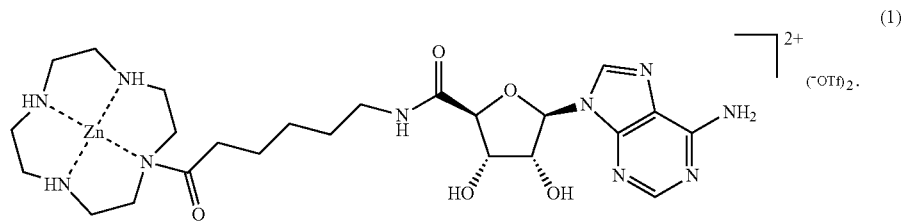

In another embodiment, the present disclosure includes compounds of the Formula (II) having the following structure

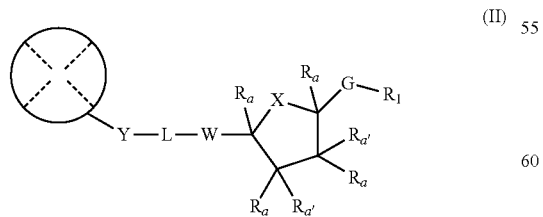

wherein Y, L, W, X, $R_a$, $R_{a'}$, G, $R_1$, and the polyazamacrocycle are as defined above. The compounds of the Formula (II) can be prepared separately from the compounds of the Formula (I) and mixed with a metal solution (or other metal containing preparation or formulation) containing the chelatable metal ion to form a compound of the Formula (I).

In another embodiment, the compound of the Formula (I) has the structure of the Formula (III)

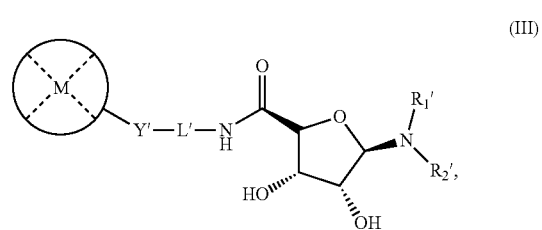

wherein

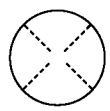

is a polyazamacrocycle chelating group, optionally having 2-6 coordination positions;

M is a chelatable metal ion;

Y' is (i) —C(=O)—, or (ii) —CH$_2$—;

L' is (C$_1$-C$_{10}$)-alkylene, or a polyethylene glycol (PEG) moiety;

R$_1$' and R$_2$' are joined together to form a
(vii) guanine or a guanine derivative;
(viii) cytosine or a cytosine derivative;
(ix) thymine or a thymine derivative; or
(x) adenine or an adenine derivative;
and Q is a suitable counteranion,
or a solvate, prodrug and/or stereoisomer thereof.

In one embodiment,

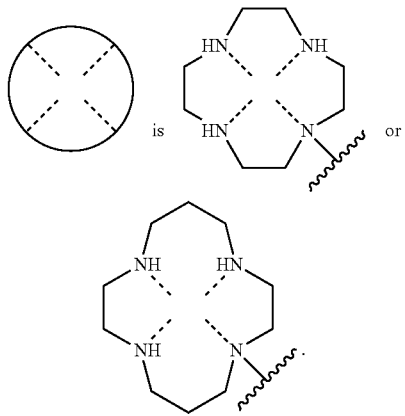

In one embodiment, R$_1$' and R$_2$' are joined together to form adenine or an adenine derivative. In one embodiment, the adenine derivative has the formula

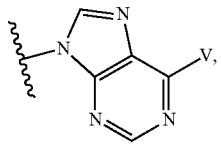

wherein
V is H, halo, OH, (C$_1$-C$_6$)-alkyl, (C$_6$-C$_{10}$-aryl, —NH—(C$_6$-C$_{10}$)-aryl, (C$_5$-C$_{10}$)-heteroaryl, (C$_3$-C$_{10}$)-cycloalkyl, (C$_3$-C$_{10}$)-heterocycloalkyl, the latter five groups being optionally substituted with —N(R')$_2$, wherein R' is H or (C$_1$-C$_3$)-alkyl. In one embodiment, V is Cl, OH or 1-aminoindan.

Compositions

The present disclosure also includes pharmaceutical compositions comprising a compound of the Formula (I), or (II), as defined above, or pharmaceutically acceptable salts, solvates, and prodrugs thereof, and a pharmaceutically acceptable carrier or diluent. The compounds are suitably formulated into pharmaceutical compositions for administration to subjects, preferably humans in a biologically compatible form suitable for administration in vivo. In one embodiment, the compound of the Formula (I) can be prepared in vivo, by administering a compound of the Formula (II) separately from a solution of a chelatable metal ion (or other preparation or formulation of a chelatable metal ion), such that the metal ion is chelated to the compound of the Formula (II) in vivo. In another embodiment, the compound of the Formula (II) is formulated as a powder, in combination with a chelatable metal ion, and upon reconstitution, forms a compound of the Formula (I).

The compositions containing the compounds of Formula (I), or (II), can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (2003-20th edition) and in The United States Pharmacopeia: The National Formulary (USP 24 NF19) published in 1999. On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of the Formula (I) may also be used in combination with other active ingredients, for example, cancer medication (chemotherapeutic agent). In one embodiment, the compound of the Formula (I) acts as a sensitizer to the cancer cells resulting in treatment using the cancer medication.

The present disclosure also includes kits for the treatment of a disease or condition in which inhibition of UBA5 would be beneficial. In one embodiment, the kit comprises:
a) a compound of the Formula (II);
b) a chelatable metal ion; and
c) instructions for use.

Methods of Medical Treatments

In one embodiment of the disclosure, the compounds of the Formula (I) are inhibitors of the UBA5 enzyme. Accordingly, in one embodiment of the disclosure, there is included a method of treating or preventing a disease or condition mediated by the UBA5 enzyme, comprising administering a pharmaceutically effective amount of a compound of the Formula (I) (or a compound of the Formula (II) with a chelatable metal ion) to a subject in need thereof. In one embodiment, the disease or condition mediated by UBA5 is a disease or condition in which inhibition of the UBA5 would be beneficial. In one aspect of the disclosure, the disease or condition is cancer, such as leukemia, lung cancer, or melanoma. In another embodiment, the leukemia is acute leukemia, chronic leukemia, lymphocytic leukemia or myelogenous leukemia. In another embodiment, the disease or condition is a parasitic disease. In another aspect of the disclosure, the disease or condition is a parasitic disease in which the UBA5 enzyme is essential for parasite survival and proliferation in host organisms. In one embodiment, the parasitic disease is Leishmaniasis.

In another embodiment, the compounds of the Formula (I) (or a compound of the Formula (II) with a chelatable metal ion) are useful for inhibiting the enzyme UBA5. In one aspect of the disclosure, the compounds of the Formula (I) (or a compound of the Formula (II) with a chelatable metal ion) are useful for the treatment or prevention of cancer, such as leukemia, lung cancer, or melanoma. In another embodiment, the leukemia is acute leukemia, chronic leukemia, lymphocytic leukemia or myelogenous leukemia. In another aspect of the disclosure, the compounds of the Formula (I) (or a compound of the Formula (II) with a chelatable metal ion) are useful for the treatment or prevention of parasitic diseases, such as Leishmaniasis.

The compounds of the Formula (I) may also be used in combination with other cancer medications or chemotherapeutic agents for the treatment of cancer. In one embodiment, the compound of the Formula (I) acts as a sensitizer to the cancer cells resulting in treatment using the cancer medication.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present disclosure.

The operation of the disclosure is illustrated by the following representative examples. As is apparent to those skilled in the art, many of the details of the examples may be changed while still practicing the disclosure described herein.

Examples

Methods and Materials

Cell Lines and Culture Techniques

Human erythroleukemia K-562 and MV-4-11 cells were cultured in Iscove's modified Dulbecco's medium (Gibco) supplemented with 10% FBS (Sigma). Breast carcinoma lines (MCF7, MDA-MB-231), lung cancer cells (A549, SK-Luci6) and melanoma cells (MDA-MB-435) were gifts from Dr. Leda Raptis (Queen's University). Normal human lung fibroblast cells (MRC-9) were obtained from ATCC (Catalog number: ATCCCCL-212). All remaining cells were grown in Dulbecco's modified Eagle's medium (DMEM,) supplemented with 10% FBS (sigma). Confluence of live cells was estimated visually under phase contrast microscopy.

Cell Proliferation

Sk-Luci6, A549 and MRC-9 were each plated as $5 \times 10^3$ cells per well and grown in 10% serum on a 96 well plate. Cells were treated with either a DMSO control, or 50 to 200 µM of 1.5.Zn (n=3). Cell numbers were obtained at 24 hr time points over a period of 72 hrs using trypan blue exclusion assay (BioRad; #145-0021) and counted using a hemocytometer.

Western Blotting

Cells were washed twice with cold PBS and protein extracts were prepared using RIPA buffer with a protease and phosphatase inhibitor cocktail (Roche #11836153001, #04906845001). Protein concentrations were determined using the BCA protein quantification technique (BCA Protein assay kit, Pierce). In each assay, 30 µg of whole cell protein extract was resolved on a 10% SDS-polyacrylamide gel and transferred to a PVDF membrane (Bio-Rad). The membranes were blocked with SuperBlock (Thermo scientific; No. 37515) for at least 1 hr followed by an overnight incubation in primary antibody. Blots were probed with antibodies against UBA5 (abcam; ab109227) and UFM-1 (abcam; ab09305) in a 1:1000 dilution, and anti-β-actin (1:5000 dilution; Cell Signaling, 3700S) was used as a loading control. Fluorescent labeled secondary antibodies anti-rabbit Alexa Fluor® 647 Conjugate (red, 1:5000) and anti-mouse Alexa Fluor® 488 Conjugate (green, 1:20,000) were used to detect bands (Cell Signaling; 4414S and 4408S, respectively). The bands were visualized and analyzed using Image lab software (Bio-Rad).

In Vitro Enzymatic Assays

All proteins and antibodies, with the exception of GST-UBA5, GST-UFC1 and GST-UFM1, and mouse anti-His antibody (abcam), were purchased from Boston Biochem. To determine the effects of compound 1.5.Zn on Ub/Ubl-E2 loading, tagged and untagged E1 proteins (50 nM His6-UBA1, or UAE; 10 nM APPBP1/UBA3, or NAE; 1 µM GST-UBA5 [in-house]) were incubated with their respective Ub/Ubl's (1 µM Ub; 500 nM NEDD8; 10 µM GST-UFM1 [in-house]) and E2 proteins (500 nM His6-UBCH6; 500 nM UBC12; 10 µM GST-UFC1 [in-house]) and various concentrations of ATP (Sigma-Aldrich; 1 µM, 20 µM, 50 µM, respectively) in 20 µL assay buffer (50 mM HEPES, 5 mM $MgCl_2$, 0.5% BSA, pH 7.4 for UAE and NAE assays, and 50 mM BIS-TRIS, 10 mM $MgCl_2$, 100 mM NaCl, 0.1 mM DTT, pH 6.5 for GST-UBA5 assay) for 1 hour (UAE and NAE) or 30 min (UBA5 assay), in the presence and absence of compound 1.5.Zn. For kinetic assays, the formation of the UFC1-UFM1 transthiolation product was measured under varying concentrations of ATP (0 to 1 mM) in the absence or presence of compound 1.5.Zn at varying time points from 0 to 60 min. Initial rates were recorded over 30 second time intervals from 0 to 2.5 min (normal kinetics) or 0 to 5 min (inhibition kinetics). Reactions were initiated by the addition of ATP and stopped using 4× Laemmli sample buffer (Bio-Rad). The generated protein conjugates were separated on a 10% non-degenerating SDS-polyacrylamide gel (4-15% gels were used for the UAE transthiolaton assay), followed by Western blot analysis, with the exception of GST-UBA5 where protein bands were detected using Coomassie™ Brilliant Blue R-250 staining or Stain-Free gel imaging for the enzymatic assays (Bio-Rad). Transfers for the UAE and NAE immunoblots were performed using nitrocellulose membranes and blocking and blotting was performed as described above with cellular protein extracts. The His6-tagged Ub-UBCH6 complex was detected using an anti-His mouse monoclonal primary antibody (1:500, abcam). A rabbit anti-NEDD8 polyclonal primary antibody (1:500, BostonBiochem) was used for the detection of the E2-NEDD8 complexes. All Ub/Ubl-E2 complex bands were revealed using enhanced chemiluminescent detection (Bio-Rad), and band intensity measurements were carried out using Image Lab software (ChemiDoc XRS, Bio-Rad). Inhibitory data was fit to a dose-response curve (Y=Bottom+ (Top−Bottom)/(1+10^(X-Log IC50))) using GraphPad Prism 6. Kinetic enzymatic assay data was fit to a substrate inhibition curve in the absence of compound 1 (Y=Vmax*X/ (Km+X*(1+X/Ki)) and was fit to a non-competitive inhibition curve incorporating substrate inhibition in the presence of inhibitor at 5 µM (Vmaxinh=Vmax/(1+1/Ki), Y=Vmaxinh*X/(Km+X)). Statistical analysis was performed using an ANOVA with Tukey's multiple comparison post hoc test (GraphPad Prism 6).

Chemical Methods

All solvents and reagents were purchased from Sigma Aldrich and used as received, with the exception of 1,4,7, 10-tetraazacyclododecane (Pure Chemistry Scientific Inc.) and N-benzyloxycarbonyl-6-aminohexanoic acid (Alfa Aesar). During all reactions, product formation was monitored using silica gel thin-layer chromatography (TLC), which was visualized by UV light or developed by treatment with $KMnO_4$ stain. $^1H$ and $^{13}C$ NMR spectra were acquired using a Bruker 400 spectrometer at 23° C., operating at 400 MHz for $^1H$ NMR and 100 MHz for $^{13}C$ NMR spectroscopy. Samples were dissolved in $CDCl_3$ or MeOD-$d_4$, Chemical shifts (δ) were reported in parts per million (ppm), proceeding calibration to residual isotopic solvent peak, and coupling constants (J) were reported in Hz. Low resolution mass spectrometry of the intermediates was carried out using a Waters Micromass ZQ equipped with an ESI source. An AB/Sciex QStar mass spectrometer equipped with an ESI source and MS/MS was utilized for accurate mass determination. Purifications by preparatory high performance liquid chromatography (prepHPLC) were performed using an Atlantis Prep T3 10 μm C18 (2) 250×19 mm column run at 20 mL/min using gradient mixtures of water with 0.1% TFA and acetonitrile. Crude mixtures were injected as a solution in 4:1 0.1% TFA in water/acetonitrile. The purity of the final compound was evaluated using NMR spectroscopy, mass spectrometry, and HPLC. Analytical HPLC conditions were tailored for an Agilent 1100 Series analytical column (4.6× 150 mm silicon hydride column, MicroSolv Technology Corporation) using a gradient starting with 100% acetonitrile down to 70% acetonitrile and 30% MilliQ water with 0.05% trifluoroacetic acid over a period of 20 minutes.

S.1.1 Experimental Procedure—Synthesis of 1.5.Zn in Scheme 1

Scheme 1. Conditons for each synthetic step include: a. Boc$_2$O, CHCl$_3$, 12 hr; b. TBTU, DIPEA, DMF, 12 hr; c. Pd/c, H$_2$, MeOH, 12 hr; d. Acetone, p-TsOH, 3 hr; e. TEMPO, DIB, MeCN, H$_2$O, 6 hr; f. TBTU, DIPEA. DMF. 12 hr; g. TFA, H$_2$O, 2 hr; h. Zn(OTF)$_2$, MeOH, 2 hr.

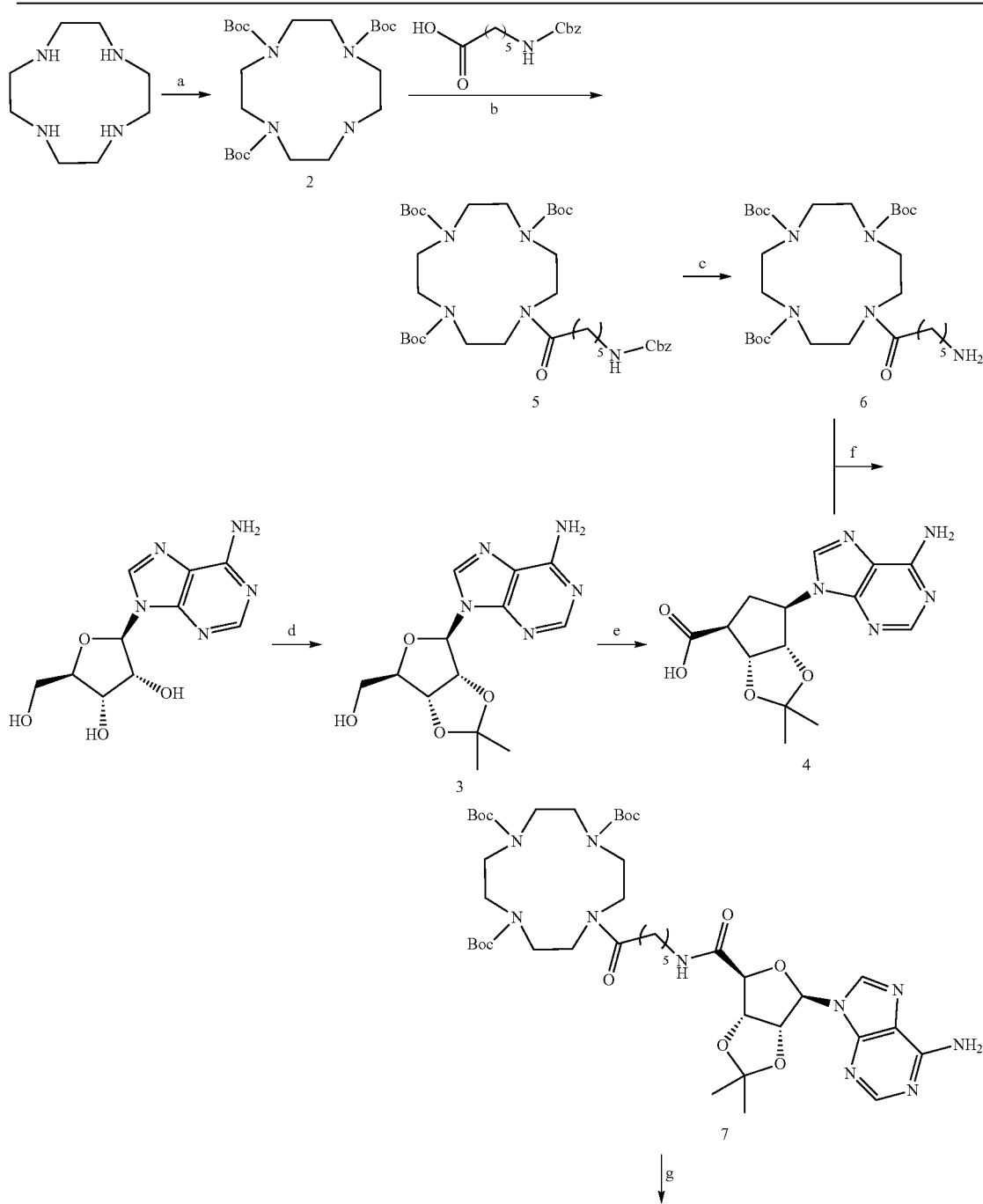

-continued

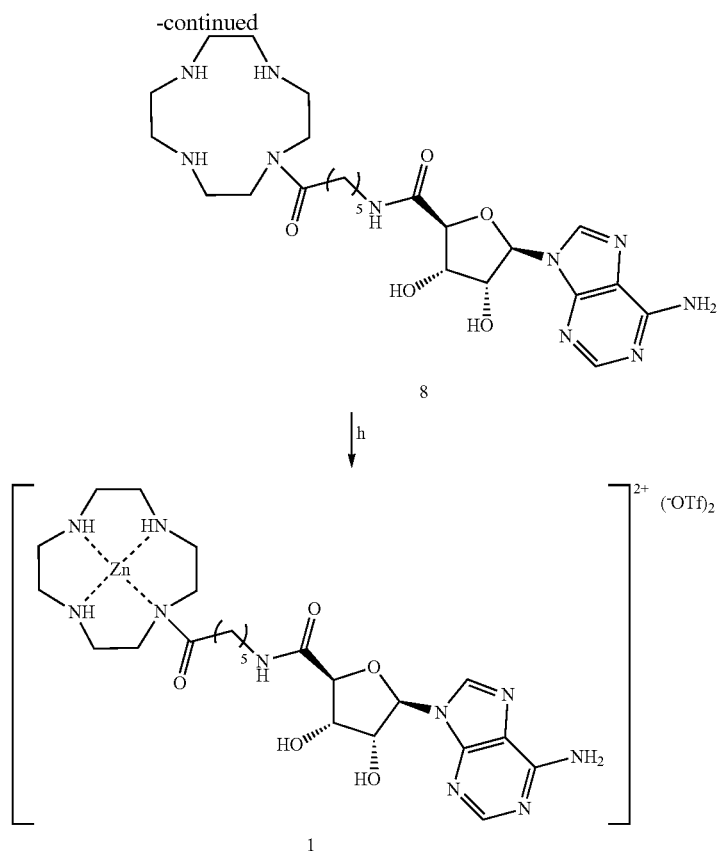

8

↓h 1 (⁻OTf)₂ tri-tert-butyl 1,4,7,10-tetraazacyclododecane-1,4,7-tricarboxylate (2)

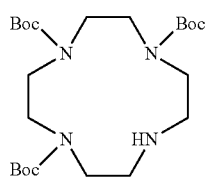

((3aR,4R,6R,6aR)-6-(6-amino-9H-purin-9-yl)-2,2-dimethyltetrahydrofuro[3,4-d][1,3]dioxol-4-yl)methanol (3)

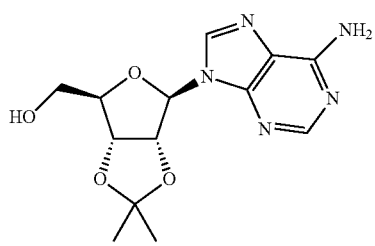 [SMILES: CC1(C)O[C@@H]2[C@H](O1)[C@@H](CO)O[C@H]2n1cnc2c(N)ncnc21]

Di-tert-butyl dicarbonate (16.5 g, 0.076 mol) in chloroform (100 mL) was added dropwise to a chilled mixture of 1,4,7,10-tetraazacyclododecane (5.0 g, 0.029 mol) and diisopropylamine (15 mL, 0.087 mol) in chloroform (200 mL) over a period of three hours. The reaction was then stirred overnight under an atmosphere of nitrogen. The reaction was concentrated, brought up in ethyl acetate (600 mL) and washed with saturated sodium bicarbonate (200 mL), followed by one wash of monobasic potassium phosphate (200 mL of 1 M) and brine (200 mL). The ethyl acetate was dried over sodium sulfate, filtered and concentrated. The crude reaction was purified using flash chromatography (4:1 ethyl acetate:hexanes) to yield a white solid (7.84 g, 57%). $^{1}$H NMR (400 MHz, CDCl3) δ 3.67-3.52 (br, 4H), 3.46-3.14 (m, 8H), 2.88-2.72 (br, 4H), 1.44 (s, 9H), 1.42 (s, 18H); $^{13}$C NMR (100 MHz, CDCl3) δ 155.4, 79.2, 79.1, 50.8, 49.3, 49.3, 48.7, 45.8, 44.8, 28.5, 28.3; LRMS (ESI): m/z [M+H]+ calc'd for C23H45N4O6+473.33, found 473.33.

Adenosine (2.0 g, 7.5 mmol) was stirred in acetone (400 mL) with para-toluene sulfonic acid monohydrate (14.3 g, 75 mmol) for three hours at room temperature under nitrogen. Upon completion, the reaction was basified with saturated sodium bicarbonate (400 mL) until the pH was slightly basic via litmus paper detection. The acetone was concentrated and the product was extracted from the aqueous layer using ethyl acetate (5×200 mL washes). The organic layer was washed with brine, dried over sodium sulfate and solvent removed in vacuo to yield a white solid (1.91 g, 86%). $^{1}$H NMR (400 MHz, CD3OD) δ 8.31 (s, 1H), 8.18 (s, 1H), 6.16-6.12 (d, J=2.5 Hz, 1H), 5.29-5.24 (m, 1H), 5.05-5.01 (m, 1H), 4.39-4.34 (br, 1H), 3.81-3.75 (dd, J=12.2 Hz, 2.5 Hz, 1H), 3.74-3.67 (dd, J=12.2 Hz, 2.8 Hz, 1H), 1.61 (s, 3H), 1.37 (s, 3H); $^{13}$C NMR (100 MHz, CD3OD) δ 155.9, 152.2, 148.5, 140.2, 119.1, 113.7, 91.3, 86.5, 83.7, 81.4, (3aS,4S,6R,6aR)-6-(6-amino-9H-purin-9-yl)-2,2-dimethyltetrahydrofuro[3,4-d][1,3]dioxole-4-carboxylic acid (4)

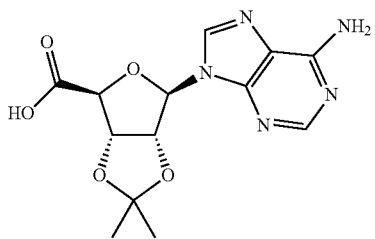 [SMILES: CC1(C)O[C@@H]2[C@H](O1)[C@@H](C(=O)O)O[C@H]2n1cnc2c(N)ncnc21]

Compound 3 (1.0 g, 3.25 mmol) was stirred in acetonitrile:water (1:1, 8 mL: 8 mL) with (diacetoxyiodo)benzene (DIB) (2.3 g, 7.12 mmol) and 2,2,6,6-Tetramethylpiperidine 1-oxyl (TEMPO) (406 mg, 2.6 mmol) for 6 hours at room temperature until product precipitated out of solution. Product was collected by vacuum filtration and dried to yield a white solid (899 mg, 83%). 1H NMR (400 MHz, CDCl3) δ 12.79 (br, 1H), 8.22 (s, 1H), 8.06 (s, 1H), 6.32-6.29 (br, 1H), 5.54-5.49 (d, J=5.1 Hz, 1H), 5.47-5.42 (d, J=5.4 Hz, 1H), 4.68-4.65 (br, 1H), 1.49 (s, 3H), 1.33 (s, 3H); 13C NMR (100 MHz, CDCl3) δ 171.0, 156.3, 152.6, 149.4, 140.7, 119.1, 113.0, 89.8, 85.7, 84.1, 83.7, 26.8, 25.2; LRMS (ESI): m/z [M]− calc'd for C13H17N5O5−320.10, found 320.11.

tri-tert-butyl 10-(6-(((benzyloxy)carbonyl)amino)hexanoyl)-1,4,7,10-tetraazacyclododecane-1,4,7-tricarboxylate (5)

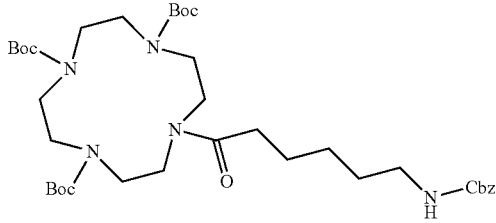 [SMILES: CC(C)(C)OC(=O)N1CCN(C(=O)CCCCCNC(=O)OCc2ccccc2)CCN(C(=O)OC(C)(C)C)CCN(C(=O)OC(C)(C)C)CC1]

6-(phenoxycarbonylamino)hexanoic acid (337 mg, 1.34 mmol, 1 eq) was dissolved in dimethylformamide (5 mL) to which was added O-(Benzotriazol-1-yl)-N,N,N',N'-tetramethyluronium tetrafluoroborate (TBTU) (516 mg, 1.61 mmol, 1.2 eq) and N,N'-diisopropylamine (303 uL, 1.74 mmol, 1.3 eq) at room temperature. After five minutes of stirring, compound 2 (634 mg, 1.34 mmol, 1 eq) was added to the reaction and stirred overnight at room temperature under an atmosphere of nitrogen. Subsequently, the reaction was brought up in ethyl acetate (80 mL) and washed with aqueous saturated sodium bicarbonate (50 mL) three times, dried over sodium sulfate, filtered and concentrated. The crude reaction was purified using silica gel chromatography (1:1 ethyl acetate/hexanes) to yield a white solid (804 mg, 75% yield). mp 64-67° C.; FT-IR (v, cm$^{-1}$, KBr) 3356, 2975, 2934, 1697, 1647, 1468, 1250; $^{1}$H NMR (400 MHz, CD$_{3}$OD) δ 7.38-7.25 (m, 5H), 5.05 (s, 2H), 3.60-3.35 (m, 16H), 3.16-3.09 (m, 2H), 2.39-2.32 (t, J=7.3 Hz, 2H), 1.68-1.58 (quint., J=7.4 Hz, 2H), 1.57-1.42 (m, 29H), 1.42-1.30 (m, 2H); $^{13}$C NMR (100 MHz, CD$_{3}$OD) δ 174.7, 157.3, 157.1, 156.9, 155.8, 137.0, 127.9, 127.4, 127.3, 80.2, 56.7, 50.6, 50.1, 49.4, 32.7, 29.7, 27.9, 26.1, 24.6; LRMS (ESI): m/z [M+H]$^{+}$ calc'd for C$_{37}$H$_{62}$N$_{5}$O$_{9}$$^{+}$ 720.45, found 720.51.

tri-tert-butyl 10-(6-aminohexanoyl)-1,4,7,10-tetraazacyclododecane-1,4,7-tricarboxylate (6)

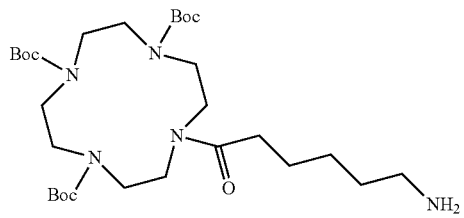 [SMILES: CC(C)(C)OC(=O)N1CCN(C(=O)CCCCCN)CCN(C(=O)OC(C)(C)C)CCN(C(=O)OC(C)(C)C)CC1]

Compound 5 (500 mg, 0.69 mmol) was dissolved in methanol, and 0.1 eq. of 10% w/w palladium on carbon (73 mg, 0.069 mmol) was added. The reaction was purged with hydrogen and stirred overnight at room temperature under a hydrogen atmosphere. The reaction was then filtered through celite and the solvent removed in vacuo to yield a yellow oil (393 mg, 97%). FT-IR (v, cm$^{-1}$, KBr) 3358, 2976, 2934, 1697, 1648, 1165; $^{1}$H NMR (400 MHz, CD$_{3}$OD) δ 3.61-3.35 (m, 16H), 2.67-2.62 (t, J=7.2 Hz, 2H), 2.41-2.35 (t, J=7.4 Hz, 2H), 1.69-1.59 (quint., J=7.6 Hz, 2H), 1.65-1.45 (m, 29H), 1.43-1.34 (m, 2H); $^{13}$C NMR (100 MHz, CD$_{3}$OD) δ 174.6, 157.0, 155.7, 80.2, 50.1, 49.6, 49.4, 40.8, 32.7, 31.9, 27.4, 26.2, 24.8; LRMS (ESI): m/z [M+H]+ calc'd for C$_{29}$H$_{56}$N$_{5}$O$_{7}$$^{+}$ 586.42, found 586.40.

tri-tert-butyl 10-(6-(((3aS,4S,6R,6aR)-6-(6-amino-9H-purin-9-yl)-2,2-dimethyltetrahydrofuro[3,4-d][1,3]dioxole-4-carboxamido)hexanoyl)-1,4,7,10-tetraazacyclododecane-1,4,7-tricarboxylate (7)

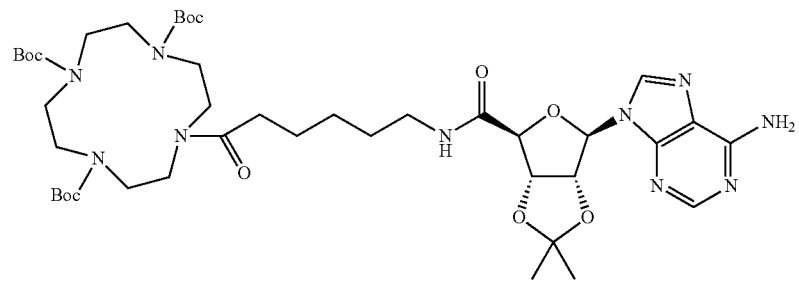 [SMILES: CC(C)(C)OC(=O)N1CCN(C(=O)CCCCCNC(=O)[C@H]2O[C@@H](n3cnc4c(N)ncnc43)[C@@H]3OC(C)(C)O[C@@H]32)CCN(C(=O)OC(C)(C)C)CCN(C(=O)OC(C)(C)C)CC1]

Compound 4 (321 mg, 1.0 mmol, 1 eq) was dissolved in dimethylformamide (4 mL) to which was added O-(Benzotriazol-1-yl)-N,N,N',N'-tetramethyluronium tetrafluoroborate (TBTU) (385 mg, 1.2 mmol, 1.2 eq) and N,N'-diisopropylamine (1.3 mmol, 226 uL, 1.3 eq) at room temperature. After five minutes of stirring, compound 6 (586 mg, 1.0 mmol, 1 eq) was added to the reaction and stirred overnight at room temperature under an atmosphere of nitrogen. Subsequently, the reaction was brought up in ethyl acetate (80 mL) and washed with aqueous saturated sodium bicarbonate (50 mL) three times, dried over sodium sulfate, filtered and concentrated. The crude reaction was purified using silica gel chromatography (1:9 MeOH/DCM) to yield a white solid (693 mg, 78%). mp 138-141° C.; FT-IR (v, cm$^{-1}$, KBr) 3427, 2978, 1629, 1366, 1158; $^1$H NMR (400 MHz, CDCl$_3$) δ 8.27 (s, 1H), 7.86 (s, 1H), 6.15-6.05 (br, 3H), 5.50-5.40 (m, 2H), 4.68 (br, 1H), 3.60-3.24 (m, 16H), 3.00-2.92 (m, 2H), 2.33 (br, 1H), 2.26-2.19 (t, J=7.5 Hz, 2H), 1.60 (s, 3H), 1.47-1.42 (m, 27H), 1.38 (s, 3H); $^{13}$C NMR (100 MHz, CDCl$_3$) δ 174.6, 170.0, 157.0, 155.8, 152.4, 148.8, 140.9, 118.9, 113.3, 90.8, 87.1, 83.7, 83.6, 80.3, 50.6, 50.1, 49.6, 49.4, 38.4, 38.3, 32.6, 28.1, 27.3, 26.1, 25.6, 24.5, 23.9; LRMS (ESI): m/z [M+H]+ calc'd for C$_{42}$H$_{69}$N$_{10}$O$_{11}$$^+$ 889.51, found 889.60.

(2S,3S,4R,5R)—N-(6-(1,4,7,10-tetraazacyclododecan-1-yl)-6-oxohexyl)-5-(6-amino-9H-purin-9-yl)-3,4-dihydroxytetrahydrofuran-2-carboxamide (8)

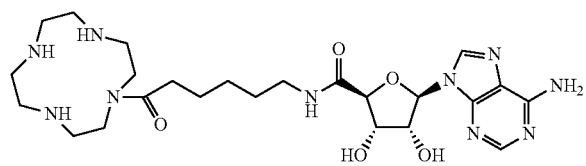 [SMILES: Nc1ncnc2c1ncn2[C@@H]1O[C@H](C(=O)NCCCCCC(=O)N2CCNCCNCCNCC2)[C@@H](O)[C@H]1O]

Compound 7 (500 mg, 0.56 mmol) was dissolved in a solution of 5 mL water and 5 mL trifluoroacetic acid and allowed to stir at room temperature for 2 hours. The solvent was then removed in vacuo and the crude mixture was purified by prepHPLC to yield a white solid (282 mg, 92%). mp 123-128° C.; FT-IR (v, cm$^{-1}$, KBr) 3424, 1644, 1206; $^1$H NMR (400 MHz, CD$_3$OD) δ 8.66 (s, 1H), 8.44 (s, 1H), 6.17-6.14 (d, J=6.5 Hz, 1H), 4.72-4.68 (dd, J=6.4 Hz, 4.9 Hz, 1H), 4.51-4.49 (d, J=2.9 Hz, 1H), 4.42-4.39 (dd, J=4.8 Hz, 2.8 Hz, 1H), 3.80-3.63 (m, 4H), 3.20 (br, 12H), 2.48-2.42 (t, J=7.5 Hz, 2H), 1.66-1.52 (m, 4H), 1.43-1.33 (m, 2H); $^{13}$C NMR (100 MHz, CDCl$_3$) δ 176.3, 170.4, 151.7, 148.1, 145.4, 142.8, 120.6, 119.4, 117.7, 114.8, 111.9, 89.1, 84.4, 73.3, 45.6, 45.0, 44.6, 44.1, 43.2, 42.5, 38.5, 33.1, 28.6, 25.8, 23.9; LRMS (ESI): m/z [M+H]$^+$ calc'd for C$_{24}$H$_{41}$N$_{10}$O$_5$$^+$ 549.33, found 549.24. HRMS (ESI): m/z [M+H]$^+$ calc'd for C$_{24}$H$_{41}$N$_{10}$O$_5$$^+$ 549.3255, found 549.3246.

(2S,3S,4R,5R)—N-(6-(1,4,7,10-tetraazacyclododecan-1-yl)-6-oxohexyl)-5-(6-amino-9H-purin-9-yl)-3,4-dihydroxytetrahydrofuran-2-carboxamide zinc trifluoromethanesulfonate (1.5.Zn)

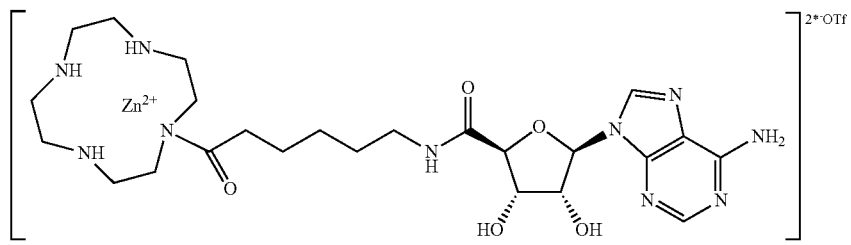

Compound 8 (30 mg, 0.055 mmol) and zinc trifluoromethansulfonate (20 mg, 0.055 mmol) were added to 1 mL of MeOH and allowed to stir for 2 hours. The MeOH was removed in vacuo to yield a clear white solid (50 mg, quantitative). decomp 185° C.; FT-IR (v, cm$^{-1}$, KBr) 3402, 1698, 1655, 1253, 1037; $^1$H NMR (400 MHz, CD$_3$OD) δ 1.41 (quint, J=7.60 Hz, 2H, COCH$_2$CH$_2$CH$_2$CH$_2$CH$_2$NH), 1.59 (quint, J=7.12 Hz, 2H, COCH$_2$CH$_2$CH$_2$CH$_2$CH$_2$NH), 1.66 (quint, J=7.39 Hz, 2H, COCH$_2$CH$_2$CH$_2$CH$_2$CH$_2$NH), 2.48 (t, J=7.42 Hz, 2H, COCH$_2$CH$_2$CH$_2$CH$_2$CH$_2$NH), 3.16-3.34 (m, 14H, 6× cyclen CH$_2$, COCH$_2$CH$_2$CH$_2$CH$_2$CH$_2$NH), 3.67-3.79 (br, 4H, 2× cyclen CH$_2$), 4.41 (dd, J=4.84 and 2.71 Hz, 1H, 3'H), 4.50 (d, J=2.62 Hz, 1H, 4'H), 4.71 (dd, J=6.55 and 4.89 Hz, 1H, 2'H), 6.15 (d, J=6.38 Hz, 1H, 1'H), 8.42 (s, 1H, O2-H), 8.63 (s, 1H, C8-H); LRMS (ESI): m/z [M+H]$^+$ calc'd for C$_{26}$H$_{41}$F$_6$N$_{10}$O$_{11}$S$_2$Zn$^+$ 911.16, found 911.21.

Scheme 2: Synthesis of Further Compounds of the Disclosure

Scheme 2 - Synthesis of derivatives 1C-4C, metal and adenosine C6-modification derivatives of 1
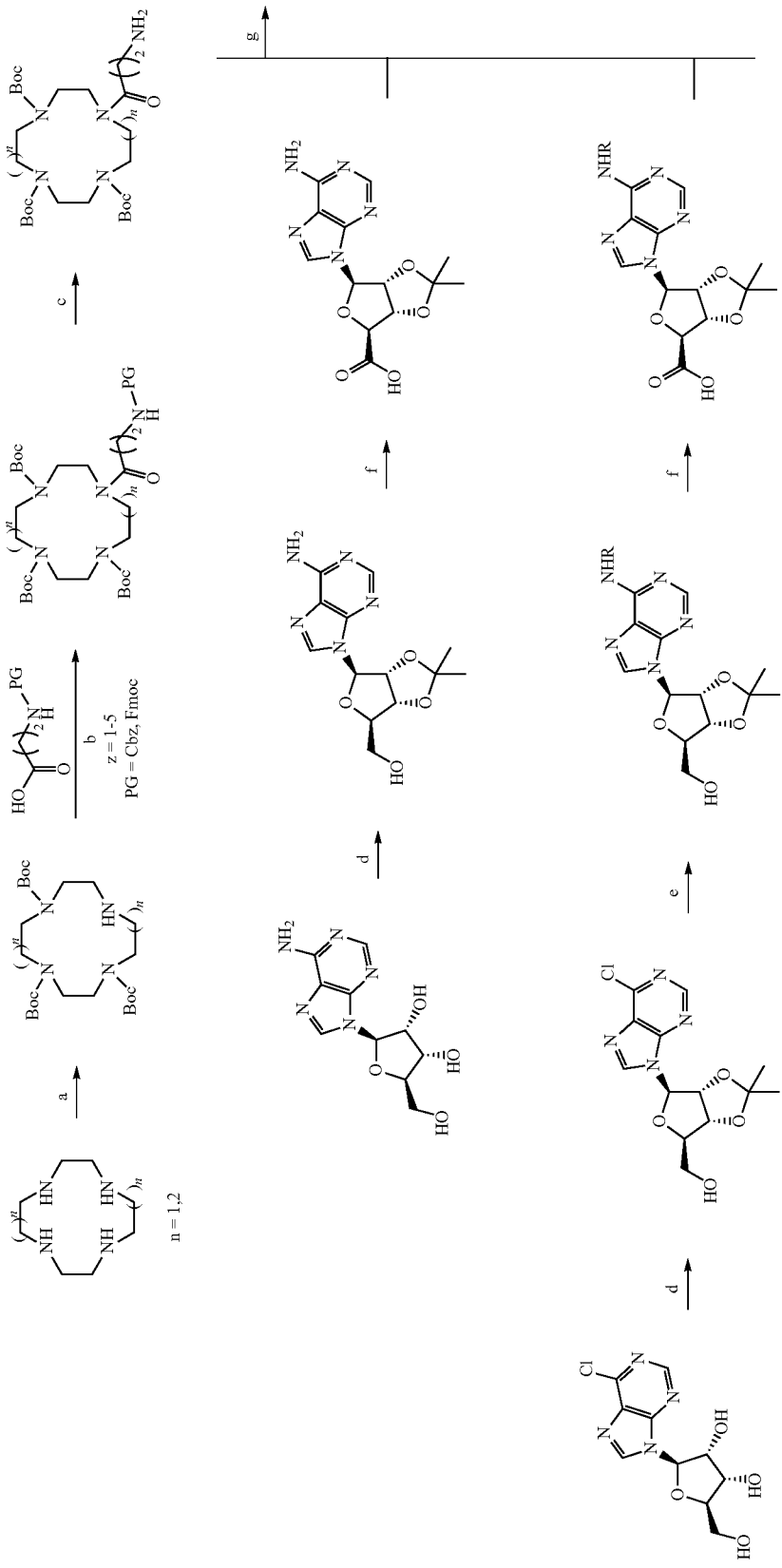

-continued
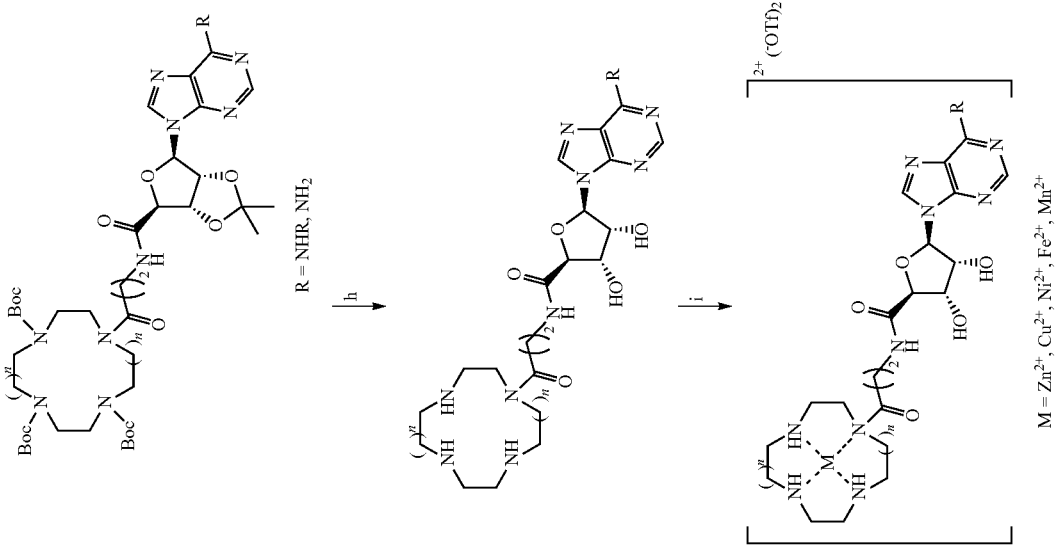
a) Boc₂O (3.1 equiv.), CHCl₃, 0° C.-rt, 12 h; b) TBTU (1.2 equiv.), DIPEA (1.3 equiv.), DMF, rt, 12 h; c) (i) for Cbz: Pd/C (10.0 mol %), H₂, MeOH, rt, 12 h; (ii) for Fmoc: 20% piperidine in DMF, rt, 1-3 h; d) Acetone, p-tsOH (10.0 equiv.), rt, 3 h; e) H₂NR, DIPEA DMSO, 105-135° C., 40 min-5 h, microwave assisted; f) TEMPO (0.5 equiv.), MeCN, H₂O, rt, 6 h; g) TBTU (1.2 equiv.), DIPEA (1.3 equiv.), DIB (2.2 equiv.), DMF, rt,12 h; h) TFA, H₂O, rt, 2 h; i) M(OTf)₂ (M = Zn²⁺, Cu²⁺, Ni²⁺, Fe²⁺, Mn²⁺), MeOH, rt, 2 h.

Scheme 3: Synthesis of Further Compounds of the Disclosure

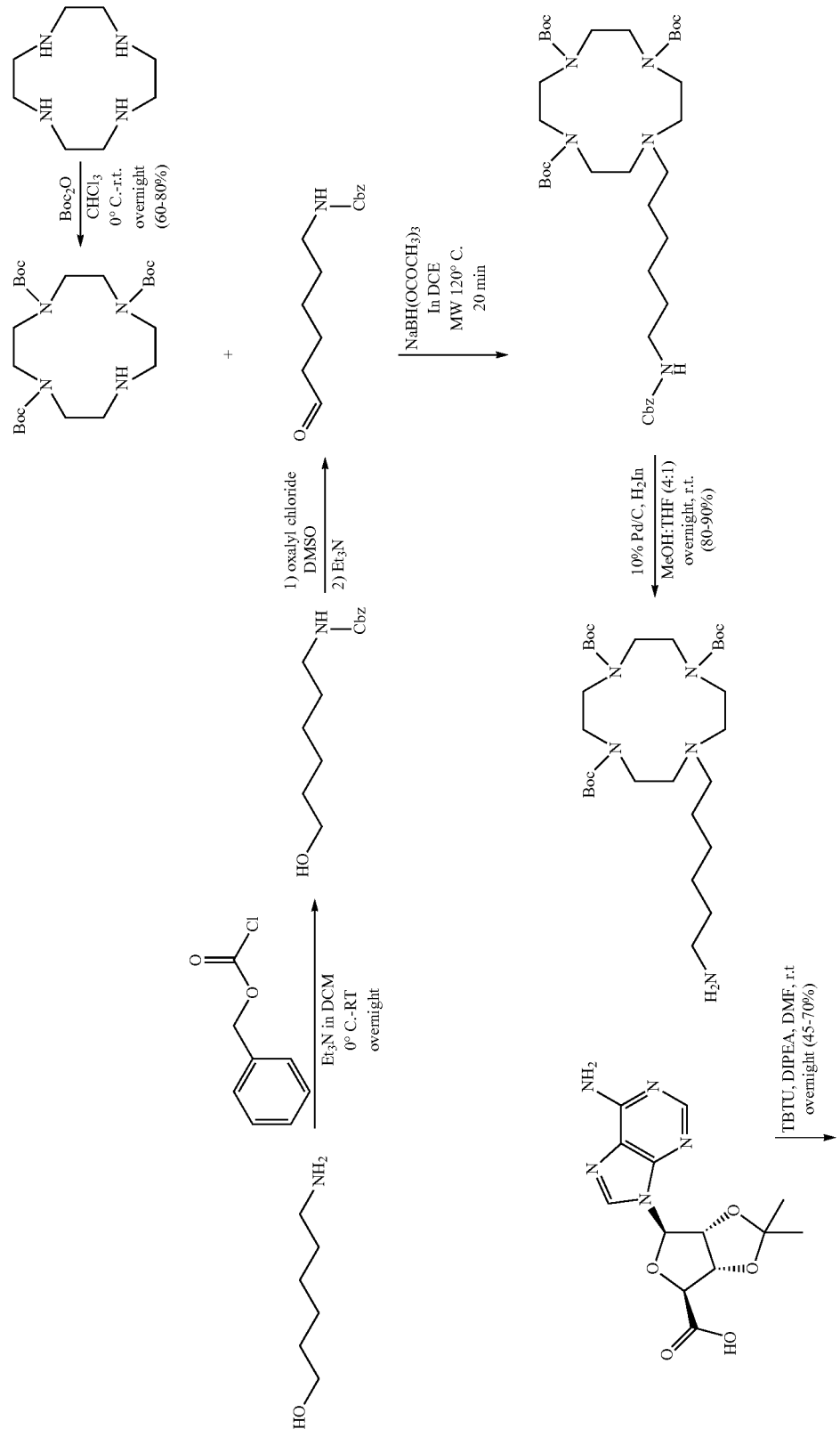
Scheme 3 - Synthesis of 5AC derivative.

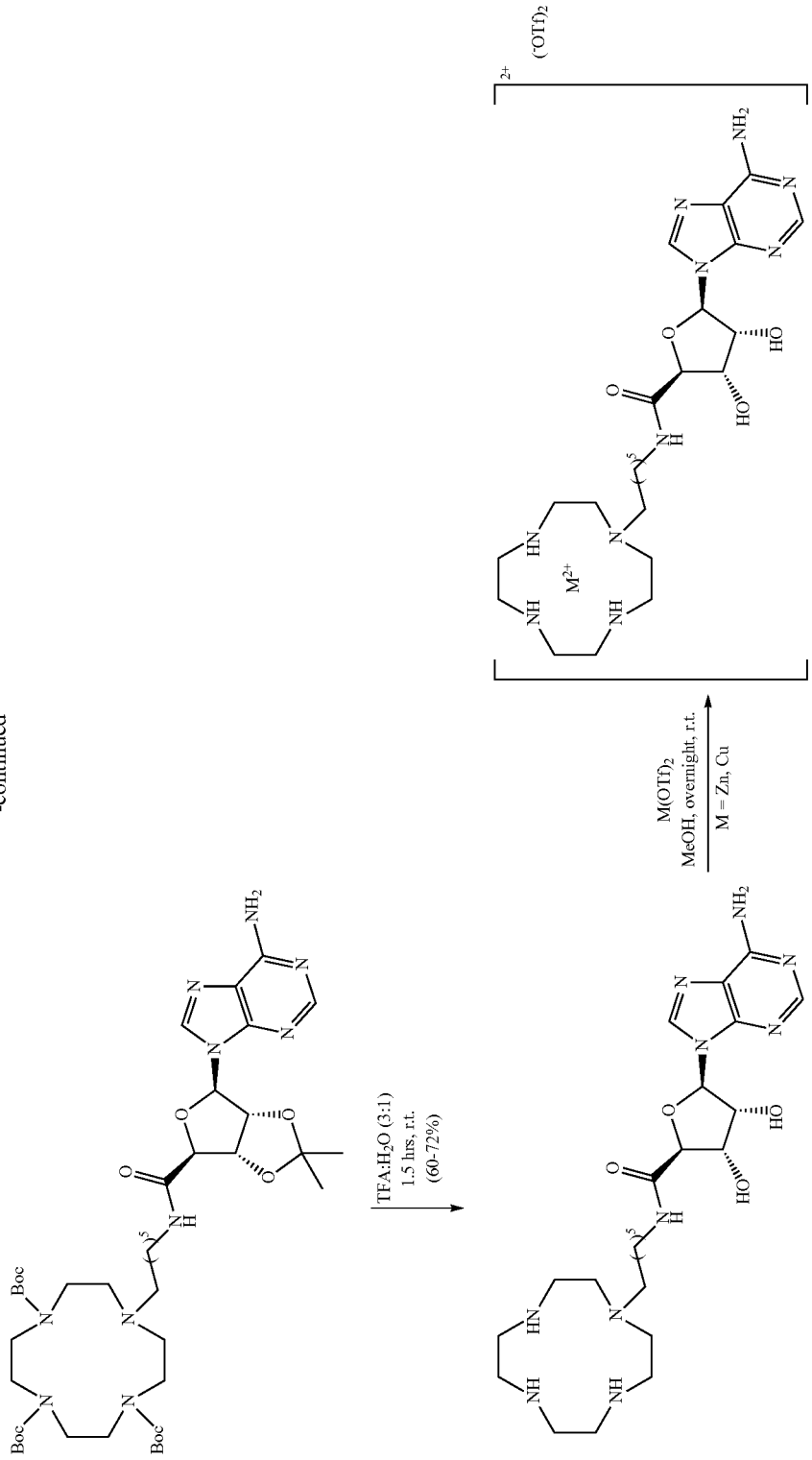

Scheme 4: Synthesis of 1AC derivatives

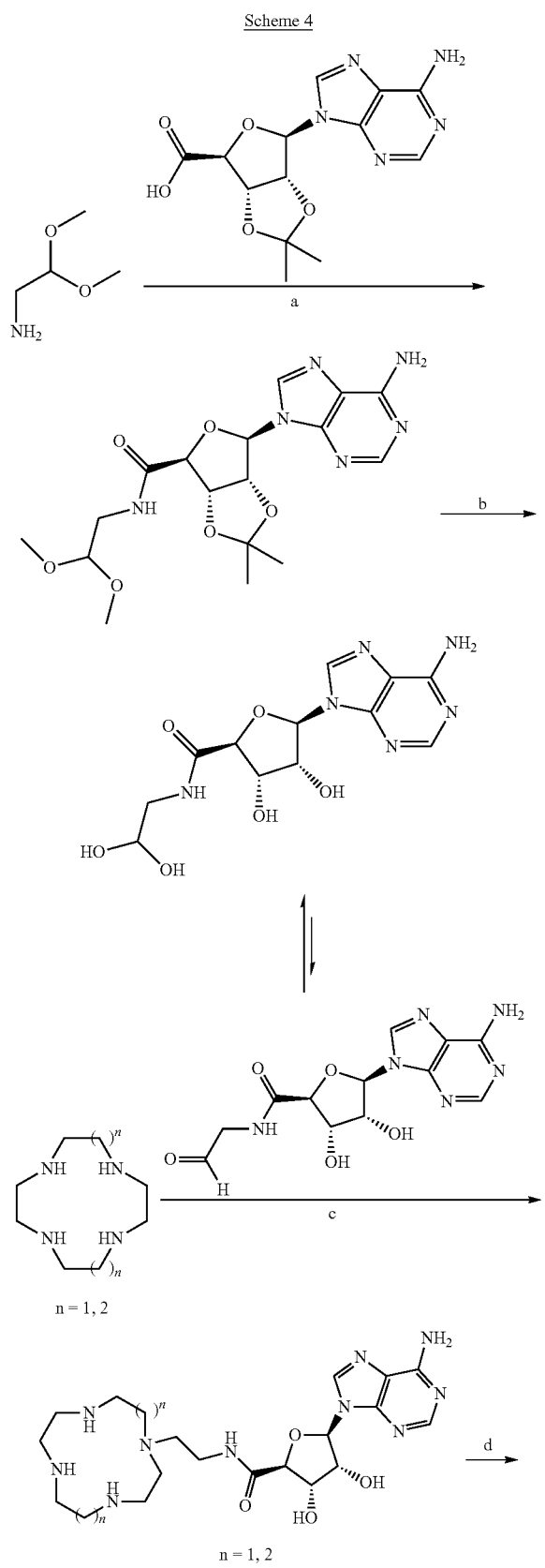

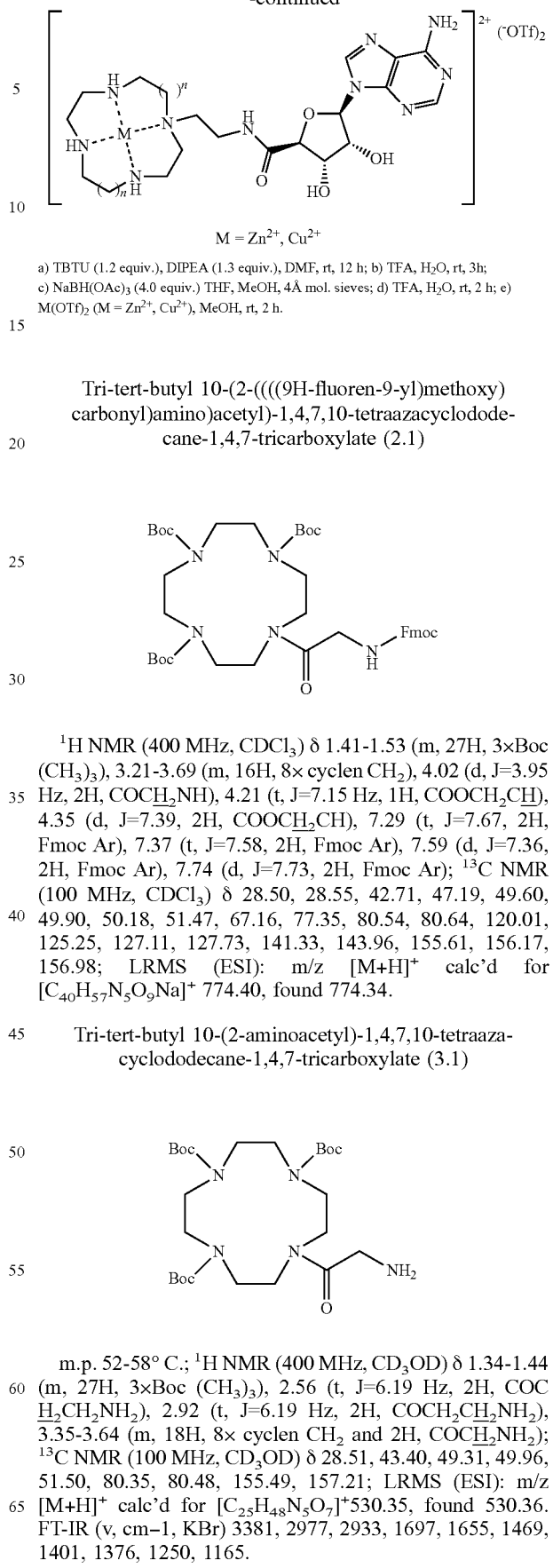

$M = Zn^{2+}, Cu^{2+}$ a) TBTU (1.2 equiv.), DIPEA (1.3 equiv.), DMF, rt, 12 h; b) TFA, H₂O, rt, 3h; c) NaBH(OAc)₃ (4.0 equiv.) THF, MeOH, 4Å mol. sieves; d) TFA, H₂O, rt, 2 h; e) M(OTf)₂ (M = Zn²⁺, Cu²⁺), MeOH, rt, 2 h.

Tri-tert-butyl 10-(2-(((((9H-fluoren-9-yl)methoxy)carbonyl)amino)acetyl)-1,4,7,10-tetraazacyclododecane-1,4,7-tricarboxylate (2.1)

$^1$H NMR (400 MHz, CDCl$_3$) δ 1.41-1.53 (m, 27H, 3×Boc (CH$_3$)$_3$), 3.21-3.69 (m, 16H, 8× cyclen CH$_2$), 4.02 (d, J=3.95 Hz, 2H, COCH$_2$NH), 4.21 (t, J=7.15 Hz, 1H, COOCH$_2$CH), 4.35 (d, J=7.39, 2H, COOCH$_2$CH), 7.29 (t, J=7.67, 2H, Fmoc Ar), 7.37 (t, J=7.58, 2H, Fmoc Ar), 7.59 (d, J=7.36, 2H, Fmoc Ar), 7.74 (d, J=7.73, 2H, Fmoc Ar); $^{13}$C NMR (100 MHz, CDCl$_3$) δ 28.50, 28.55, 42.71, 47.19, 49.60, 49.90, 50.18, 51.47, 67.16, 77.35, 80.54, 80.64, 120.01, 125.25, 127.11, 127.73, 141.33, 143.96, 155.61, 156.17, 156.98; LRMS (ESI): m/z [M+H]$^+$ calc'd for [C$_{40}$H$_{57}$N$_5$O$_9$Na]$^+$ 774.40, found 774.34.

Tri-tert-butyl 10-(2-aminoacetyl)-1,4,7,10-tetraazacyclododecane-1,4,7-tricarboxylate (3.1)

m.p. 52-58° C.; $^1$H NMR (400 MHz, CD$_3$OD) δ 1.34-1.44 (m, 27H, 3×Boc (CH$_3$)$_3$), 2.56 (t, J=6.19 Hz, 2H, COCH$_2$CH$_2$NH$_2$), 2.92 (t, J=6.19 Hz, 2H, COCH$_2$CH$_2$NH$_2$), 3.35-3.64 (m, 18H, 8× cyclen CH$_2$ and 2H, COCH$_2$NH$_2$); $^{13}$C NMR (100 MHz, CD$_3$OD) δ 28.51, 43.40, 49.31, 49.96, 51.50, 80.35, 80.48, 155.49, 157.21; LRMS (ESI): m/z [M+H]$^+$ calc'd for [C$_{25}$H$_{48}$N$_5$O$_7$]$^+$ 530.35, found 530.36. FT-IR (v, cm−1, KBr) 3381, 2977, 2933, 1697, 1655, 1469, 1401, 1376, 1250, 1165.

41

Tri-tert-butyl 10-(2-((3aS,4S,6R,6aR)-6-(6-amino-9H-purin-9-yl)-2,2-dimethyltetrahydrofuro[3,4-d][1,3]dioxole-4-carboxamido)acetyl)-1,4,7,10-tetraazacyclododecane-1,4,7-tricarboxylate

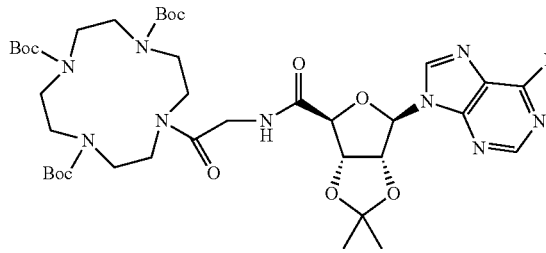

$^1$H NMR (400 MHz, CDCl$_3$) δ 1.30 (s, 3H, COC(CH$_3$)$_2$), 1.34 (s, 9H, Boc), 1.38 (s, 9H, Boc), 1.40 (s, 9H, Boc), 1.53 (s, 3H, COC(CH$_3$)$_2$), 3.09-3.54 (m, 16H, 8× cyclen CH$_2$), 3.61 (dd, J=17.79 and 3.89 Hz, 1H, COCH$_2$NH), 3.73 (dd, J=17.34 and 4.00 Hz, 1H, COCH$_2$NH), 4.66 (d, J=1.80 Hz, 1H, 4'H), 5.34 (dd, J=6.03 and 1.61, 1H, 3'H), 5.45 (dd, J=5.89 and 1.73 Hz, 1H, 2'H), 6.11 (d, J=1.81, 1H, 1'H), 6.29 (s, 2H, NH$_2$), 7.33 (s, 1H, NH), 7.86 (s, 1H, C2-H), 8.15 (s, 1H, C8-H); $^{13}$C NMR (100 MHz, CDCl$_3$) δ 25.14, 26.92, 28.48, 28.52, 40.59, 49.31, 49.47, 49.78, 49.94, 51.44, 80.47, 80.56, 80.62, 83.51, 83.80, 86.88, 91.50, 114.23, 120.07, 139.94, 149.32, 153.07, 155.54, 155.76, 157.01, 169.01; LRMS (ESI): m/z [M+H]$^+$ calc'd for [C$_{38}$H$_{61}$N$_{10}$O$_{11}$]$^+$833.44, found 833.40.

(2S,3S,4R,5R)-5-(6-amino-9H-purin-9-yl)-3,4-dihydroxy-N-(2-oxo-2-(1,4,7,10-tetraazacyclododecan-1-yl)ethyl)tetrahydrofuran-2-carboxamide (1.1.L)

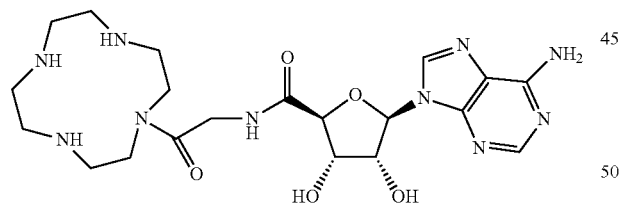

$^1$H NMR (400 MHz, CD$_3$OD) 3.12-3.26 (m, 12H, 6× cyclen CH$_2$), 3.59-3.88 (m, 4H, 2× cyclen CH$_2$), 4.09 (d, J=16.5 Hz, 1H, 4'H), 4.23 (d, J=16.5 Hz, 1H, 3'H), 4.46-4.51 (m, 1H, COCH2CH2NH), 4.51-4.56 (m, 1H, COCH2CH2NH), 4.72 (t, J=5.4 Hz, 1H, 2'H), 6.16 (d, J=6.3 Hz, 1H, 1'H), 8.42 (s, 1H, C2-H), 8.52 (s, 1H, C8-H); $^{13}$C NMR (100 MHz, CD$_3$OD) δ 34.97, 36.64, 44.29, 45.08, 46.43, 46.64, 46.89, 47.34, 74.66, 74.68, 85.25, 90.75, 120.85, 144.33, 147.04, 149.87, 152.98, 172.83, 175.84; $^{13}$C NMR (100 MHz, MeOD) δ 42.54, 44.04, 44.80, 45.28, 46.95, 49.65, 74.67, 74.75, 85.47, 90.32, 101.39, 120.75, 144.38, 146.77, 150.10, 152.72, 172.78, 173.22.

42

(2S,3S,4R,5R)-5-(6-amino-9H-purin-9-yl)-3,4-dihydroxy-N-(2-oxo-2-(1,4,7,10-tetraazacyclododecan-1-yl)ethyl)tetrahydrofuran-2-carboxamide zinc (II) trifluromethanesulfonate (1.1.Zn)

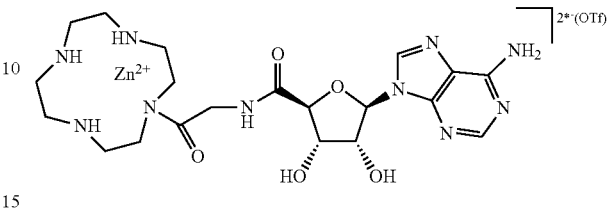

Metal coordination assessed visually. For characterization of ligand, see 1.1.L.

(2S,3S,4R,5R)-5-(6-amino-9H-purin-9-yl)-3,4-dihydroxy-N-(2-oxo-2-(1,4,7,10-tetraazacyclododecan-1-yl)ethyl)tetrahydrofuran-2-carboxamide, copper(II) trifluromethanesulfonate (1.1.Cu)

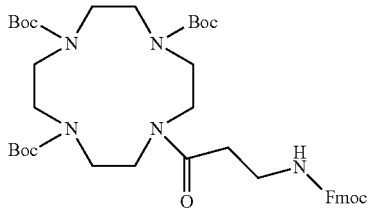

Metal coordination assessed visually. For characterization of ligand, see 1.1.L.

Tri-tert-butyl 10-(3-((((9H-fluoren-9-yl)methoxy)carbonyl)amino)propanoyl)-1,4,7,10-tetraazacyclododecane-1,4,7-tricarboxylate $^1$H NMR (400 MHz, CDCl$_3$) δ 1.38-1.56 (m, 27H, 3×Boc (CH$_3$)$_3$), 2.57 (t, J=4.88 Hz, 2H, COCH$_2$CH$_2$NH), 3.23-3.69 (m, 18H, 8× cyclen CH$_2$, COCH$_2$CH$_2$NH), 4.20 (t, J=7.13 Hz, 1H, COOCH$_2$CH), 4.34 (d, J=6.93 Hz, 2H, COOCH$_2$CH), 5.81 (s, 1H, NH), 7.31 (t, J=7.36 Hz, 2H, Fmoc Ar), 7.39 (t, J=7.36 Hz, 2H, Fmoc Ar), 7.60 (d, J=7.45 Hz, 2H, Fmoc Ar), 7.76 (d, J=7.57 Hz, 2H, Fmoc Ar); $^{13}$C NMR (100 MHz, CDCl$_3$) δ 28.39, 33.45, 36.80, 47.22, 49.77, 50.30, 51.39, 66.62, 80.32, 80.40, 119.90, 125.11, 126.98, 127.60, 141.21, 143.95, 155.43, 156.34, 157.11; LRMS (ESI): m/z [M+H]$^+$ calc'd for [C$_{41}$H$_{59}$N$_5$NaO$_9$]$^+$788.42, found 788.37.

Tri-tert-butyl 10-(3-aminopropanoyl)-1,4,7,10-tetraazacyclododecane-1,4,7-tricarboxylate

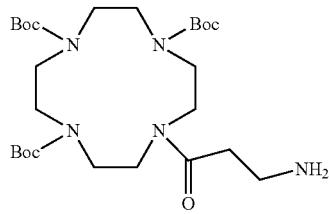 [SMILES: CC(C)(C)OC(=O)N1CCN(C(=O)CCN)CCN(C(=O)OC(C)(C)C)CCN(C(=O)OC(C)(C)C)CC1]

$^1$H NMR (400 MHz, CD$_3$OD) δ 1.44-1.54 (m, 27H, 3×Boc (CH$_3$)$_3$), 2.56 (t, J=6.19 Hz, 2H, COCH$_2$CH$_2$NH$_2$), 2.92 (t, J=6.19 Hz, 2H, COCH$_2$CH$_2$NH$_2$), 3.35-3.64 (m, 16H, 8× cyclen CH$_2$); $^{13}$C NMR (100 MHz, CD$_3$OD) δ 28.79, 28.83, 36.49, 38.59, 50.87, 50.99, 51.35, 52.06, 81.63, 81.68, 157.22, 158.29, 158.51, 174.41; LRMS (ESI): m/z [M+H]$^+$ calc'd for [C$_{26}$H$_{49}$N$_5$O$_7$]$^+$543.36, found 544.24.

Tri-tert-butyl 10-(3-((3aR,4S,6R)-6-(6-amino-9H-purin-9-yl)-2,2-dimethyltetrahydrofuro[3,4-d][1,3]dioxole-4-carboxamido)propanoyl)-1,4,7,10-tetraazacyclododecane-1,4,7-tricarboxylate

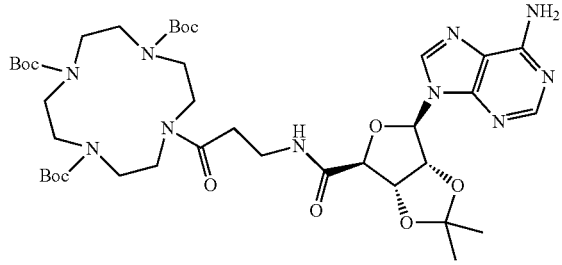 [SMILES: CC(C)(C)OC(=O)N1CCN(C(=O)CCNC(=O)[C@H]2O[C@@H](n3cnc4c(N)ncnc43)[C@@H]3OC(C)(C)O[C@@H]32)CCN(C(=O)OC(C)(C)C)CCN(C(=O)OC(C)(C)C)CC1]

$^1$H NMR (400 MHz, CD$_3$OD) δ 1.39 (s, 3H, COC(CH$_3$)$_2$), 1.44-1.48 (m, 27H, 3×Boc (CH$_3$)$_3$), 1.58 (s, 3H, COC(CH$_3$)$_2$), 2.38 (t, J=6.97 Hz, 2H, COCH$_2$CH$_2$NH), 3.24-3.55 (m, 18H, 8× cyclen CH$_2$, COCH$_2$CH$_2$NH), 4.67 (d, J=1.80 Hz, 1H, 4'H), 5.43 (dd, J=6.04 and 0.79 Hz, 1H, 3'H), 5.49 (dd, J=6.02 and 1.97 Hz, 1H, 2'H), 6.45 (d, J=0.91 Hz, 1H, 1'H), 8.44 (s, 1H, C2-H), 8.48 (s, 1H, C8-H); $^{13}$C NMR (100 MHz, CD$_3$OD) δ 25.31, 27.08, 28.57, 28.62, 28.71, 28.76, 28.80, 33.27, 36.17, 50.54, 50.79, 51.12, 51.36, 51.47, 52.14, 81.86, 81.90, 81.92, 84.98, 85.39, 88.83, 92.64, 115.25, 115.63, 120.78, 144.93, 145.62, 149.60, 152.29, 157.33, 158.40, 171.27; LRMS (ESI): m/z [M+H]+ calc'd for [C$_{39}$H$_{63}$N$_{10}$O$_{11}$]$^+$847.46, found 847.45.

(2S,3S,4R,5R)-5-(6-amino-9H-purin-9-yl)-3,4-dihydroxy-N-(3-oxo-3-(1,4,7,10-tetraazacyclododecan-1-yl)propyl)tetrahydrofuran-2-carboxamide (1.2.L)

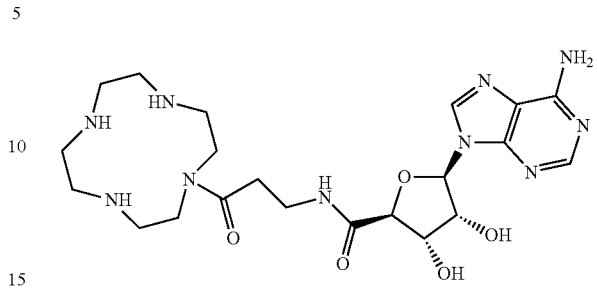

$^1$H NMR (400 MHz, CD$_3$OD) δ 2.59-2.84 (m, 2H, COCH$_2$CH$_2$NH), 3.16-3.30 (m, 12H, 6× cyclen CH$_2$), 3.50-3.88 (m, 6H, 2× cyclen CH$_2$, COCH$_2$CH$_2$NH), 4.47 (d, J=3.25 Hz, 1H, 4'H), 4.50 (t, J=4.10 Hz, 1H, 3'H), 4.72 (t, J=5.36 Hz, 1H, 2'H), 6.13 (d, J=5.85 Hz, 1H, 1'H), 8.43 (s, 1H, C2-H), 8.49 (s, 1H, C8-H); $^{13}$C NMR (100 MHz, CD$_3$OD) δ 34.97, 36.64, 44.29, 45.08, 46.43, 46.64, 46.89, 47.34, 74.66, 74.68, 85.25, 90.75, 120.85, 144.33, 147.04, 149.87, 152.98, 172.83, 175.84; HRMS (ESI): m/z [M+H]$^+$ calc'd for C$_{21}$H$_{35}$N$_{10}$O$_5$$^+$507.2793, found 507.2786.

(2S,3S,4R,5R)-5-(6-amino-9H-purin-9-yl)-3,4-dihydroxy-N-(3-oxo-3-(1,4,7,10-tetraazacyclododecan-1-yl)propyl)tetrahydrofuran-2-carboxamide zinc (II) trifluoromethanesulfonate (1.2.Zn)

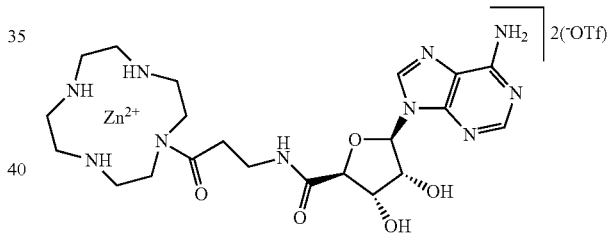

$^1$H NMR (400 MHz, CD$_3$OD) δ 2.57-2.87 (m, 2H, COCH$_2$CH$_2$NH), 3.15-3.29 (m, 12H, 6× cyclen CH$_2$), 3.47-3.92 (m, 6H, 2× cyclen CH$_2$, COCH$_2$CH$_2$NH), 4.46 (d, J=3.42 Hz, 1H, 4'H), 4.51 (t, J=4.24 Hz, 1H, 3'H), 4.72 (t, J=5.30, 1H, 2'H), 6.12 (d, J=5.59 Hz, 1H, 1'H), 8.39 (s, 1H, C2-H), 8.46 (s, 1H, C8-H).

(2S,3S,4R,5R)-5-(6-amino-9H-purin-9-yl)-3,4-dihydroxy-N-(3-oxo-3-(1,4,7,10-tetraazacyclododecan-1-yl)propyl)tetrahydrofuran-2-carboxamide, copper(II) trifluromethanesulfonate (1.2.Cu)

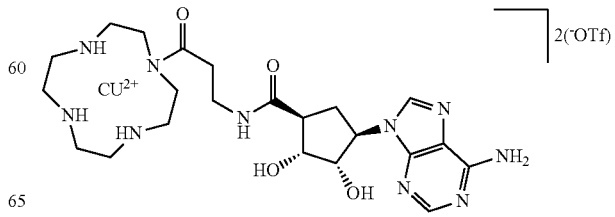

Metal coordination assessed visually. For characterization of ligand, see 1.2.L.

Tri-tert-butyl 10-(4-(((benzyloxy)carbonyl)amino)butanoyl)-1,4,7,10-tetraazacyclododecane-1,4,7-tricarboxylate

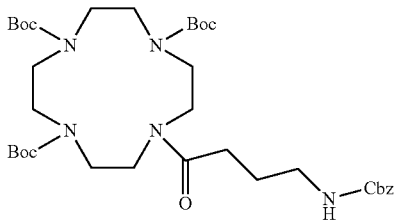 [SMILES: CC(C)(C)OC(=O)N1CCN(C(=O)CCCNC(=O)OCc2ccccc2)CCN(C(=O)OC(C)(C)C)CCN(C(=O)OC(C)(C)C)CC1]

$^1$H NMR (400 MHz, CDCl$_3$) δ 1.38-1.55 (m, 27H, 3×Boc (CH$_3$)$_3$), 1.87 (quint, J=6.47 Hz, 2H, COCH$_2$C$\underline{H}_2$CH$_2$NH), 2.37 (t, J=6.41 Hz, 2H, COC$\underline{H}_2$CH$_2$CH$_2$NH), 3.25 (q, J=6.11 Hz, 2H, COCH$_2$CH$_2$C$\underline{H}_2$NH), 3.28-3.68 (m, 16H, 8× cyclen CH$_2$), 5.08 (s, 2H, Cbz CH$_2$), 5.55 (s, 1H, NH), 7.27-7.38 (m, 5H, Cbz Ar); $^{13}$C NMR (100 MHz, CDCl$_3$) δ 24.94, 28.41, 28.46, 38.56, 40.70, 49.76, 50.33, 51.45, 66.40, 80.21, 80.32, 80.37, 127.94, 128.05, 128.40, 136.73, 155.44, 156.49, 157.13; LRMS (ESI): m/z [M+H]$^+$ calc'd for [C$_{35}$H$_{57}$N$_5$NaO$_9$]$^+$714.40, found 714.32.

Tri-tert-butyl 10-(4-aminobutanoyl)-1,4,7,10-tetraazacyclododecane-1,4,7-tricarboxylate

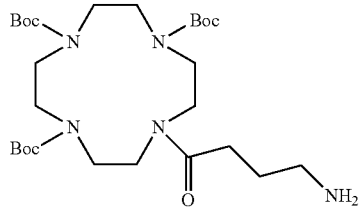 [SMILES: CC(C)(C)OC(=O)N1CCN(C(=O)CCCN)CCN(C(=O)OC(C)(C)C)CCN(C(=O)OC(C)(C)C)CC1]

$^1$H NMR (400 MHz, CD$_3$OD) δ 1.44-1.56 (br, 27H, 3×Boc (CH$_3$)$_3$), 1.80 (quint, J=7.25 Hz, 2H, COCH$_2$C$\underline{H}_2$CH$_2$NH$_2$), 2.44 (t, J=7.28 Hz, 2H, COC$\underline{H}_2$CH$_2$CH$_2$NH$_2$), 2.71 (t, J=7.03 Hz, 2H, COCH$_2$CH$_2$C$\underline{H}_2$NH$_2$), 3.36-3.63 (m, 16H, 8× cyclen CH$_2$); $^{13}$C NMR (100 MHz, CD$_3$OD) δ 28.81, 28.84, 29.00, 31.67, 42.08, 50.76, 50.91, 51.02, 51.05, 51.47, 52.03, 81.59, 157.19, 158.32, 175.51; LRMS (ESI): m/z [M+H]$^+$ calc'd for [C$_{27}$H$_{51}$N$_5$O$_7$]$^+$558.38, found 558.41.

Tri-tert-butyl 10-(4-((3aS,4S,6R,6aR)-6-(6-amino-9H-purin-9-yl)-2,2-dimethyltetrahydrofuro[3,4-d][1,3]dioxole-4-carboxamido)butanoyl)-1,4,7,10-tetraazacyclododecane-1,4,7-tricarboxylate

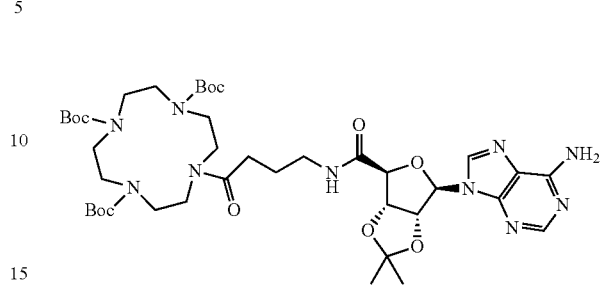

$^1$H NMR (400 MHz, CDCl$_3$) δ 1.39 (s, 3H, COC(C$\underline{H}_3$)$_2$), 1.42-1.51 (m, 27H, 3×Boc (CH$_3$)$_3$), 1.51-1.69 (m, 5H, COC(C$\underline{H}_3$)$_2$, COCH$_2$C$\underline{H}_2$CH$_2$NH), 2.13-2.29 (m, 2H, COCH$_2$CH$_2$CH$_2$NH), 2.92-3.58 (m, 18H, 8× cyclen CH$_2$, COCH$_2$CH$_2$CH$_2$NH), 4.71 (d, J=1.09 Hz, 1H, 4'H), 5.36-5.45 (m, 2H, 2'H and 3'H), 6.12 (d, J=1.96 Hz, 1H, 1'H), 6.35 (s, 2H, NH$_2$), 7.52 (br, 1H, NH), 7.92 (s, 1H, C2-H), 8.33 (s, 1H, C8-H); $^{13}$C NMR (100 MHz, CDCl$_3$) δ 24.30, 25.22, 27.10, 28.50, 28.54, 39.08, 49.68, 50.04, 50.30, 51.43, 80.27, 80.38, 80.43, 82.90, 83.76, 86.17, 91.81, 114.37, 120.21, 140.09, 149.26, 153.25, 155.47, 155.94, 157.24, 168.95; LRMS (ESI): m/z [M+H]$^+$ calc'd for [C$_{40}$H$_{64}$N$_{10}$O$_{11}$]$^+$861.48, found 861.55.

(2S,3S,4R,5R)-5-(6-amino-9H-purin-9-yl)-3,4-dihydroxy-N-(4-oxo-4-(1,4,7,10-tetraazacyclododecan-1-yl)butyl)tetrahydrofuran-2-carboxamide (1.3.L)

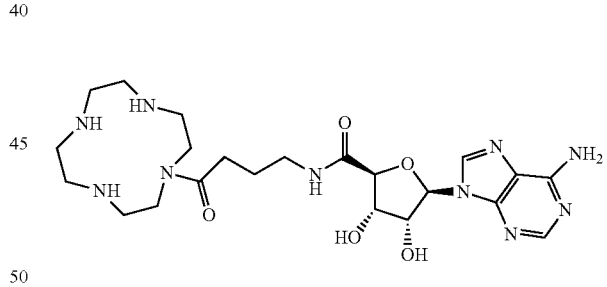

$^1$H NMR (400 MHz, CD$_3$OD) δ 1.72-1.93 (m, 2H, COCH$_2$C$\underline{H}_2$CH$_2$NH), 2.41-2.57 (m, 2H, COC$\underline{H}_2$CH$_2$CH$_2$NH), 3.13-3.30 (m, 12H, 6× cyclen CH$_2$), 3.37-3.85 (m, 6H, COCH$_2$CH$_2$C$\underline{H}_2$NH, 2× cyclen CH$_2$), 4.50 (d, J=3.68 Hz, 1H, 4'H), 4.54 (t, J=4.39 Hz, 1H, 3'H), 4.71 (t, J=5.42 Hz, 1H, 2'H), 6.13 (d, J=5.73 Hz, 1H, 1'H), 8.49 (s, 1H, C2-H), 8.52 (s, 1H, C8-H); $^{13}$C NMR (100 MHz, CD$_3$OD) δ 26.18, 31.77, 39.57, 45.69, 46.67, 48.25, 48.73, 49.22, 50.88, 73.34, 74.97, 86.49, 90.49, 121.18, 142.67, 150.14, 153.94, 157.58, 172.27, 176.26; HRMS (ESI): m/z [M+H]$^+$ calc'd for C$_{22}$H$_{37}$N$_{10}$O$_5$$^+$521.2937, found 521.2942.

(2S,3S,4R,5R)-5-(6-amino-9H-purin-9-yl)-3,4-dihydroxy-N-(4-oxo-4-(1,4,7,10-tetraazacyclododecan-1-yl)butyl)tetrahydrofuran-2-carboxamide zinc (II) trifluoromethanesulfonate (1.3.Zn)

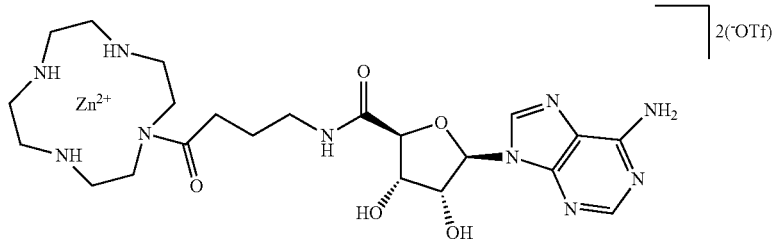 [SMILES: Nc1ncnc2c1ncn2[C@@H]1O[C@H](C(=O)NCCCC(=O)N2CCNCCNCCNCC2)[C@@H](O)[C@H]1O ; [Zn+2]]

$^1$H NMR (400 MHz, CD$_3$OD) δ 1.73-1.96 (m, 2H, COCH$_2$CH$_2$CH$_2$NH), 2.48 (t, J=5.81 Hz, 2H, COCH$_2$CH$_2$CH$_2$NH), 3.14-3.29 (m, 12H, 6× cyclen CH$_2$), 3.44-3.86 (m, 6H, 2× cyclen CH$_2$, COCH$_2$CH$_2$CH$_2$NH), 4.48 (d, J=4.38 Hz, 1H, 4'H), 4.61 (t, J. 4.79 Hz, 1H, 3'H), 4.71 (t, J=5.20 Hz, 1H, 2'H), 6.12 (d, J=5.18 Hz, 1H, 1'H), 8.41 (s, 1H, C2-H), 8.47 (s, 1H, C8-H).

(2S,3S,4R,5R)-5-(6-amino-9H-purin-9-yl)-3,4-dihydroxy-N-(4-oxo-4-(1,4,7,10-tetraazacyclododecan-1-yl)butyl)tetrahydrofuran-2-carboxamide, copper(II) trifluromethanesulfonate (1.3.Cu)

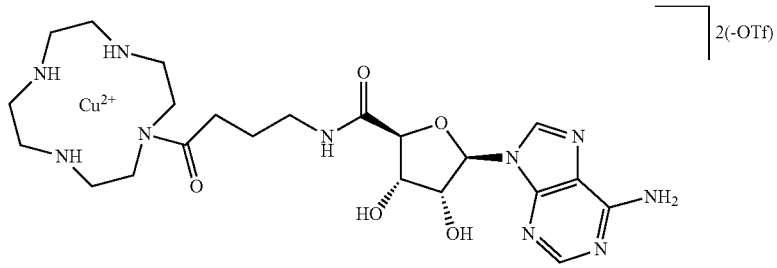

Metal coordination assessed visually. For characterization of ligand, see 1.3.L.

Tri-tert-butyl 10-(5-((((9H-fluoren-9-yl)methoxy)carbonyl)amino)pentanoyl)-1,4,7,10-tetraazacyclododecane-1,4,7-tricarboxylate

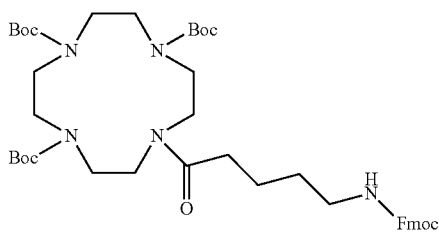

$^1$H NMR (400 MHz, CDCl$_3$) δ 1.44-1.49 (m, 27H, 3×Boc (CH$_3$)$_3$), 1.51-1.61 (m, 2H, COCH$_2$CH$_2$CH$_2$CH$_2$NH), 1.65-1.74 (m, 2H, COCH$_2$CH$_2$CH$_2$CH$_2$NH), 2.34 (t, J=6.89 Hz, 2H, COCH$_2$CH$_2$CH$_2$CH$_2$NH), 3.22 (q, J=6.39 Hz, 2H, COCH$_2$CH$_2$CH$_2$CH$_2$NH), 3.26-3.63 (m, 16H, 8× cyclen CH$_2$), 4.21 (t, J=6.73 Hz, 1H, COOCH$_2$CH), 4.37 (d, J=6.90 Hz, 2H, COOCH$_2$CH), 5.09 (s, 1H, NH), 7.31 (t, J=7.48 Hz, 2H, Fmoc Ar), 7.39 (t, J=7.54 Hz, 2H, Fmoc Ar), 7.60 (d, J=7.56 Hz, 2H, Fmoc Ar), 7.76 (d, J=7.47 Hz, 2H, Fmoc Ar); $^{13}$C NMR (100 MHz, CDCl$_3$) δ 22.20, 28.39, 28.41, 28.60, 29.41, 40.58, 47.20, 49.60, 50.24, 51.31, 66.47, 80.13, 80.25, 80.33, 119.86, 125.04, 126.94, 127.55, 141.19, 143.97; LRMS (ESI): m/z [M+H]$^+$ calc'd for [C$_{43}$H$_{63}$N$_5$NaO$_9$]$^+$ 816.45, found 816.51.

Tri-tert-butyl 10-(5-aminopentanoyl)-1,4,7,10-tetraazacyclododecane-1,4,7-tricarboxylate

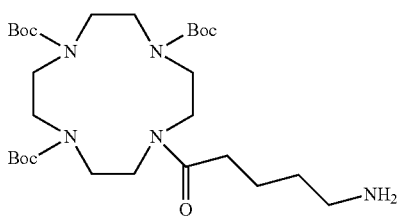 [SMILES: CC(C)(C)OC(=O)N1CCN(C(=O)CCCCN)CCN(C(=O)OC(C)(C)C)CCN(C(=O)OC(C)(C)C)CC1]

$^1$H NMR (400 MHz, CDCl$_3$) δ 1.30-1.45 (m, 27H, 3×Boc (CH$_3$)$_3$), 1.52-1.63 (m, 2H, COCH$_2$CH$_2$CH$_2$CH$_2$NH$_2$), 1.90 (br, 2H, COCH$_2$CH$_2$CH$_2$CH$_2$NH$_2$), 2.23 (t, J=7.23 Hz, 2H, COCH$_2$CH$_2$CH$_2$CH$_2$NH$_2$), 2.63 (t, J=6.35 Hz, 2H, COCH$_2$CH$_2$CH$_2$CH$_2$NH$_2$), 3.07-3.64 (m, 16H, 8× cyclen CH$_2$); $^{13}$C NMR (100 MHz, CDCl$_3$) δ 22.52, 28.45, 29.64, 33.06, 33.22, 41.84, 49.57, 50.33, 51.37, 80.08, 80.22, 80.34, 155.38, 157.27, 167.11; LRMS (ESI): m/z [M+H]$^+$ calc'd for [$C_{28}H_{54}N_5O_7$]$^+$572.39, found 572.49.

Tri-tert-butyl 10-(5-((3aS,4S,6R,6aR)-6-(6-amino-9H-purin-9-yl)-2,2-dimethyltetrahydrofuro[3,4-d][1,3]dioxole-4-carboxamido)pentanoyl)-1,4,7,10-tetraazacyclododecane-1,4,7-tricarboxylate

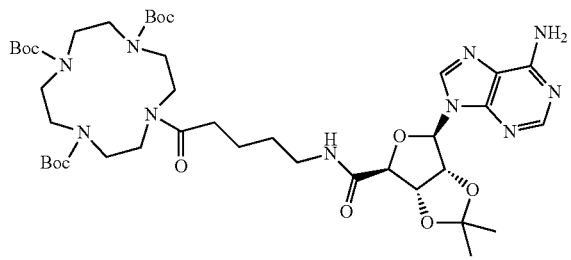 [SMILES: CC(C)(C)OC(=O)N1CCN(C(=O)CCCCNC(=O)[C@H]2O[C@@H](n3cnc4c(N)ncnc43)[C@@H]3OC(C)(C)O[C@@H]32)CCN(C(=O)OC(C)(C)C)CCN(C(=O)OC(C)(C)C)CC1]

$^1$H NMR (400 MHz, CDCl$_3$) δ 1.39 (s, 3H, COC(CH$_3$)$_2$), 1.44-1.50 (m, 27H, 3×Boc (CH$_3$)$_3$), 1.52-1.73 (m, 5H, COC(CH$_3$)$_2$, COCH$_2$CH$_2$CH$_2$CH$_2$NH), 2.20-2.32 (m, 2H, COCH$_2$CH$_2$CH$_2$CH$_2$NH), 2.95-3.13 (br, 2H, COCH$_2$CH$_2$CH$_2$CH$_2$NH), 3.15 (m, 18H, COCH$_2$CH$_2$CH$_2$CH$_2$NH, 8× cyclen CH$_2$), 4.71 (s, 1H, 4'H), 5.40-5.53 (br, 2H, 3'H, 2'H), 6.18 (s, 1H, 1'H), 6.90 (s, 2H, NH$_2$), 7.99 (s, 1H, C2-H), 8.30 (s, 1H, C8-H); $^{13}$C NMR (100 MHz, CDCl$_3$) δ 22.06, 24.96, 26.81, 28.24, 28.26, 28.57, 32.35, 38.57, 49.38, 49.99, 51.20, 79.95, 80.06, 80.10, 82.60, 83.48, 85.98, 91.35, 113.98, 119.88, 139.78, 148.86, 152.98, 155.23, 155.96, 156.97, 168.60; LRMS (ESI): m/z [M+H]+ calc'd for [$C_{42}H_{68}N_{10}O_{11}$]$^+$875.49, found 875.52.

(2S,3S,4R,5R)-5-(6-amino-9H-purin-9-yl)-3,4-dihydroxy-N-(5-oxo-5-(1,4,7,10-tetraazacyclododecan-1-yl)pentyl)tetrahydrofuran-2-carboxamide (1.4.L)

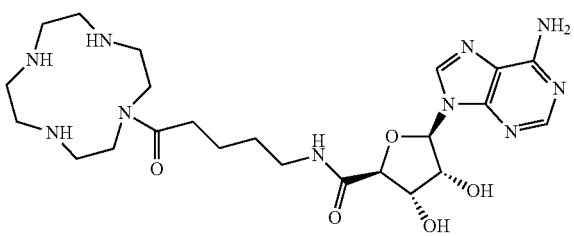 [SMILES: Nc1ncnc2c1ncn2[C@@H]1O[C@H](C(=O)NCCCCC(=O)N2CCNCCNCCNCC2)[C@@H](O)[C@H]1O]

$^1$H NMR (400 MHz, CD$_3$OD) δ 1.54-1.69 (m, 4H, COCH$_2$CH$_2$CH$_2$CH$_2$NH), 2.50 (t, J=6.82 Hz, 2H, COCH$_2$CH$_2$CH$_2$CH$_2$NH), 3.20-3.27 (m, 12H, 6× cyclen CH$_2$), 3.33-3.42 (m, 2H, COCH$_2$CH$_2$CH$_2$CH$_2$NH), 3.66-3.80 (m, 4H, 2× cyclen CH$_2$), 4.46-4.51 (m, 2H, 4'H, 3'H), 4.73 (dd, J=6.37 and 4.93 Hz, 1H, 2'H), 6.14 (d, J=6.13 Hz, 1H, 1'H), 8.48 (s, 1H, C2-H), 8.60 (s, 1H, C8-H); $^{13}$C NMR (100 MHz, CD$_3$OD) δ 22.62, 29.66, 33.85, 39.49, 44.21, 44.86, 45.54, 46.29, 46.68, 47.26, 74.74, 74.78, 85.65, 90.87, 121.01, 144.70, 146.37, 149.67, 152.76, 172.16, 177.60; HRMS (ESI): m/z [M+H]$^+$ calc'd for $C_{23}H_{39}N_{10}O_5^+$ 535.3086, found 535.3099.

(2S,3S,4R,5R)-5-(6-amino-9H-purin-9-yl)-3,4-dihydroxy-N-(5-oxo-5-(1,4,7,10-tetraazacyclododecan-1-yl)pentyl)tetrahydrofuran-2-carboxamide zinc (II) trifluoromethanesulfonate (1.4.Zn)

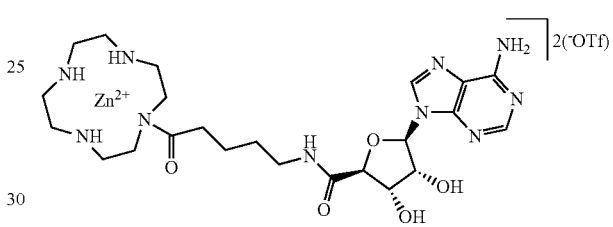

$^1$H NMR (400 MHz, CD$_3$OD) δ 1.56-1.74 (m, 4H, COCH$_2$CH$_2$CH$_2$CH$_2$NH), 2.53 (t, J=6.81 Hz, 2H, COCH$_2$CH$_2$CH$_2$CH$_2$NH), 3.20-3.27 (m, 12H, 6× cyclen CH$_2$), 3.36-3.43 (m, 2H, COCH$_2$CH$_2$CH$_2$CH$_2$NH), 3.66-3.82 (m, 4H, 2× cyclen CH$_2$), 4.46-4.53 (m, 2H, 4'H, 3'H), 4.72 (t, J=5.36 Hz, 1H, 2'H), 6.12 (d, J=5.97 Hz, 1H, 1'H), 8.42 (s, 1H, C2-H), 8.54 (s, 1H, C8-H).

(2S,3S,4R,5R)-5-(6-amino-9H-purin-9-yl)-3,4-dihydroxy-N-(5-oxo-5-(1,4,7,10-tetraazacyclododecan-1-yl)pentyl)tetrahydrofuran-2-carboxamide, copper(II) trifluoromethanesulfonate (1.4.Cu)

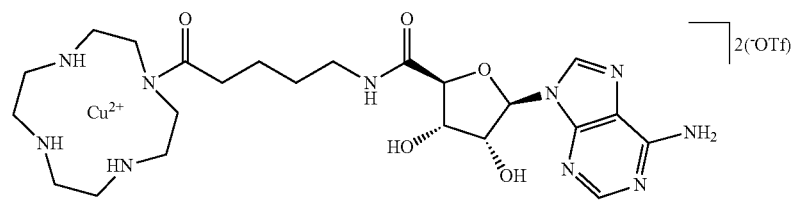

Metal coordination assessed visually. For characterization of ligand, see 1.4.L.

(2S,3S,4R,5R)—N-(6-(1,4,7,10-tetraazacyclodode-can-1-yl)-6-oxohexyl)-5-(6-amino-9H-purin-9-yl)-3,4-dihydroxytetrahydrofuran-2-carboxamide copper (II) trifluoromethanesulfonate (1.5.Cu)

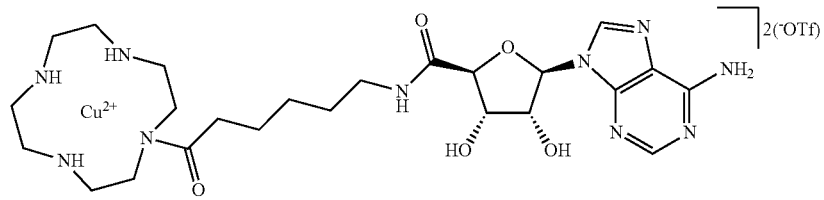

Metal coordination assessed visually. For characterization of ligand, see 1.5.L.

(2S,3S,4R,5R)—N-(6-(1,4,7,10-tetraazacyclodode-can-1-yl)-6-oxohexyl)-5-(6-amino-9H-purin-9-yl)-3,4-dihydroxytetrahydrofuran-2-carboxamide manganese (II) trifluoromethanesulfonate (1.5.Mn)

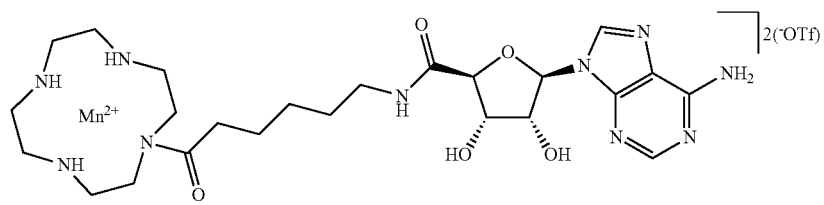

Metal coordination assessed visually. For characterization of ligand, see 1.5.L.

(2S,3S,4R,5R)—N-(6-(1,4,7,10-tetraazacyclodode-can-1-yl)-6-oxohexyl)-5-(6-amino-9H-purin-9-yl)-3,4-dihydroxytetrahydrofuran-2-carboxamide nickel (II) trifluoromethanesulfonate (1.5.Ni)

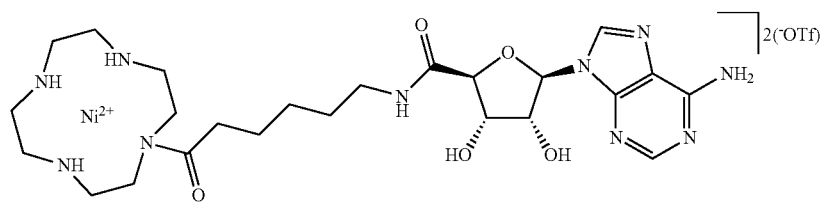

Metal coordination assessed visually. For characterization of ligand, see 1.5.L.

(2S,3S,4R,5R)—N-(6-(1,4,7,10-tetraazacyclododecan-1-yl)-6-oxohexyl)-5-(6-amino-9H-purin-9-yl)-3,4-dihydroxytetrahydrofuran-2-carboxamide iron (II) trifluoromethanesulfonate (1.5.Fe)

NH$_2$), 7.23 (bs, 1H, NH), 7.90 (s, 1H, C2-H), 8.14-8.19 (m, 1H, C8-H); $^{13}$C NMR (100 MHz, CDCl$_3$) δ 25.10, 26.85, 28.42, 28.49, 28.53, 40.29, 40.54, 45.75, 46.53, 47.17, 47.65, 48.42, 79.86, 80.01, 80.20, 83.66, 83.99, 87.31, 91.68, 91.74, 114.05, 120.27, 120.33, 149.20, 149.26, 152.86, 155.56, 155.78, 156.02, 169.06.

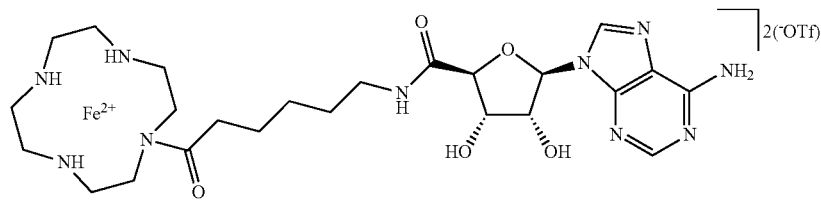

Metal coordination assessed visually. For characterization of ligand, see 1.5.L.

Tri-tert-butyl 11-(2-((3aS,4S,6R,6aR)-6-(6-amino-9H-purin-9-yl)-2,2-dimethyltetrahydrofuro[3,4-d][1,3]dioxole-4-carboxamido)acetyl)-1,4,8,11-tetraazacyclotetradecane-1,4,8-tricarboxylate (2S,3S,4R,5R)-5-(6-amino-9H-purin-9-yl)-3,4-dihydroxy-N-(2-oxo-2-(1,4,8,11-tetraazacyclotetradecan-1-yl)ethyl)tetrahydrofuran-2-carboxamide, zinc(II) trifluromethanesulfonate (1.1.Cy.Zn)

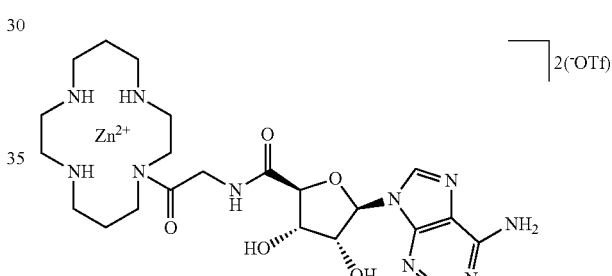

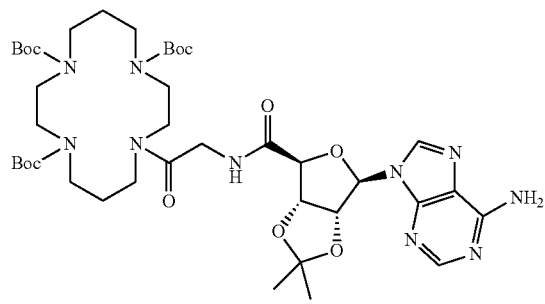 [SMILES: CC(C)(C)OC(=O)N1CCCN(C(=O)OC(C)(C)C)CCN(C(=O)OC(C)(C)C)CCCN(C(=O)CNC(=O)[C@H]2O[C@@H](n3cnc4c(N)ncnc43)[C@@H]3OC(C)(C)O[C@@H]32)CC1]

Metal coordination assessed visually.

(2S,3S,4R,5R)-5-(6-amino-9H-purin-9-yl)-3,4-dihydroxy-N-(2-oxo-2-(1,4,8,11-tetraazacyclotetradecan-1-yl)ethyl)tetrahydrofuran-2-carboxamide, copper (II) trifluoromethanesulfonate (1.1.Cy.Cu)

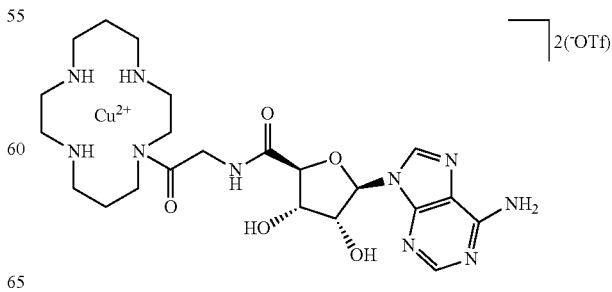

$^1$H NMR (400 MHz, CDCl$_3$) δ 1.34 (s, 3H, COC(CH$_3$)$_2$), 1.37-1.43 (m, 27H, 3×Boc), 1.56 (s, 3H, COC(CH$_3$)$_2$), 2.97-3.79 (m, 22H, 20H from 10× cyclam CH$_2$, 2H from COCH$_2$NH), 4.71 (s, 1H, 4'H), 5.35-5.43 (m, 1H, 3'H), 5.55 (d, J=6.19 Hz, 1H, 2'H), 6.14 (s, 1H, 1'H), 6.20 (bs, 2H, Metal coordination assessed visually.

tri-tert-butyl 11-(6-(((3aS,4S,6R,6aR)-6-(6-amino-9H-purin-9-yl)-2,2-dimethyltetrahydrofuro[3,4-d][1,3]dioxole-4-carboxamido)hexanoyl)-1,4,8,11-tetraazacyclotetradecane-1,4,8-tricarboxylate

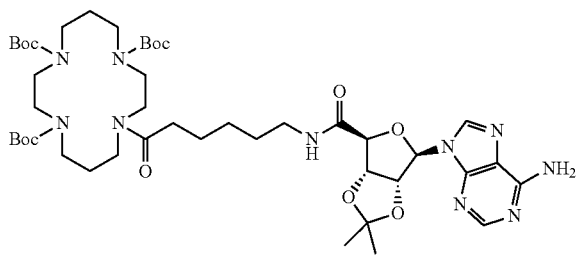 [SMILES: CC(C)(C)OC(=O)N1CCCN(C(=O)OC(C)(C)C)CCN(C(=O)OC(C)(C)C)CCCN(C(=O)CCCCCNC(=O)[C@H]2O[C@@H](n3cnc4c(N)ncnc43)[C@@H]3OC(C)(C)O[C@@H]32)CC1]

$^1$H NMR (400 MHz, CDCl$_3$) δ 0.88-1.25 (m, 4H), 1.40 (s, 3H), 1.41-1.52 (m, 27H), 1.62 (s, 3H), 1.68-1.87 (m, 4H), 2.17-2.45 (m, 2H), 2.64-3.64 (m, 20H), 4.70 (s, 1H), 5.39-5.61 (m, 2H), 6.00-6.20 (m, 1H), 6.23-6.50 (m, 2H), 6.56-7.04 (m, 1H), 7.91 (s, 1H), 8.29 (s, 1H).

(2S,3S,4R,5R)-5-(6-amino-9H-purin-9-yl)-3,4-dihydroxy-N-(6-oxo-6-(1,4,8,11-tetraazacyclotetradecan-1-yl)hexyl)tetrahydrofuran-2-carboxamide (1.5.Cy.L)

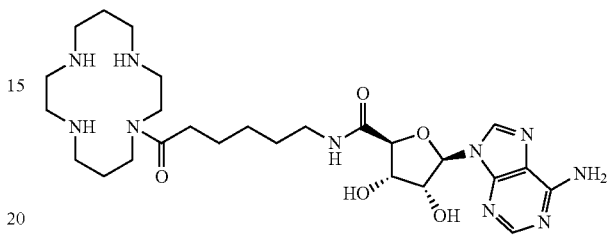

$^1$H NMR (400 MHz, CD$_3$OD) δ 1.32-1.45 (m, 2H, CH$_2$), 1.57 (p, J=7.5 Hz, 2H, CH$_2$), 1.64 (p, J=7.4 Hz, 2H, CH$_2$), 2.02-2.13 (m, 4H, cyclam-CH$_2$ & CH$_2$), 2.41 (t, J=7.4 Hz, 2H, NHCH$_2$), 3.10 (br. t, J=6.6 Hz, 2H, cyclam-CH$_2$), 3.18-3.44 (m, 12H, cyclam-CH$_2$), 3.55 (br. t, J=6.8 Hz, 2H, cyclam-CH$_2$), 3.71 (br. s, 2H, cyclam-CH$_2$), 4.40 (dd, J=4.9, 2.7 Hz, 1H, 4'H), 4.49 (d, J=2.7 Hz, 1H, 3'H), 4.71 (dd, J=6.4, 4.8 Hz, 1H, 2'H), 6.15 (d, J=6.4 Hz, 1H, 1'H), 8.43 (s, 1H, C2-H), 8.65 (s, 1H, C8-H); $^{13}$C NMR (100 MHz, CD$_3$OD) δ 24.09, 25.87, 28.60, 32.51, 38.44, 43.50, 44.67, 73.31, 73.48, 84.39, 89.07, 111.76, 114.65, 117.54, 119.37, 120.43, 142.91, 145.00, 148.12, 151.46, 160.21, 160.56, 160.92, 170.42.

(2S,3S,4R,5R)-5-(6-amino-9H-purin-9-yl)-3,4-dihydroxy-N-(6-oxo-6-(1,4,8,11-tetraazacyclotetradecan-1-yl)hexyl)tetrahydrofuran-2-carboxamide, zinc(II) trifluromethanesulfonate (1.5.Cy.Zn)

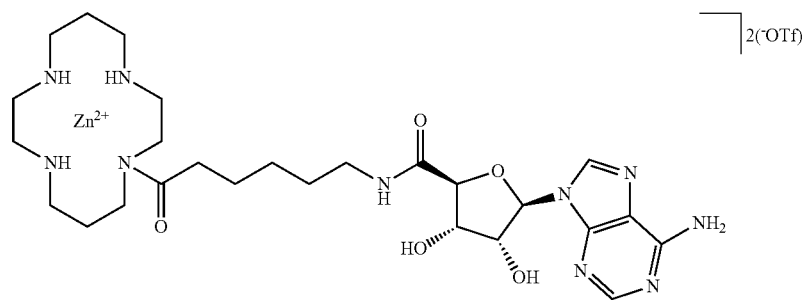

Metal coordination assessed visually. For characterization of ligand, see 1.5.Cy.L.

(2S,3S,4R,5R)-5-(6-amino-9H-purin-9-yl)-3,4-dihydroxy-N-(6-oxo-6-(1,4,8,11-tetraazacyclotetradecan-1-yl)hexyl)tetrahydrofuran-2-carboxamide, copper (II) trifluromethanesulfonate (1.5.Cy.Cu)

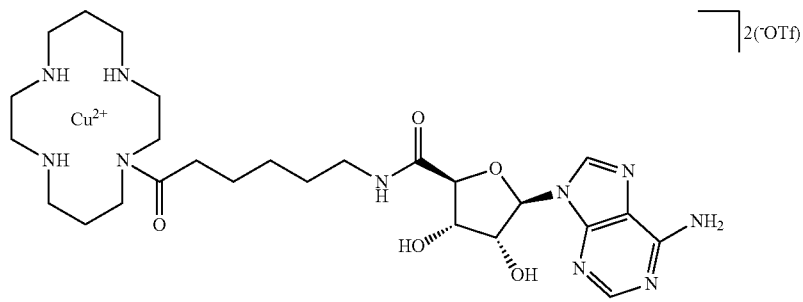

Metal coordination assessed visually. For characterization of ligand, see 1.5.Cy.L.

(2S,3S,4R,5R)—N-(6-(1,4,7,10-tetraazacyclododecan-1-yl)hexyl)-5-(6-amino-9H-purin-9-yl)-3,4-dihydroxytetrahydrofuran-2-carboxamide (1.5.A.L)

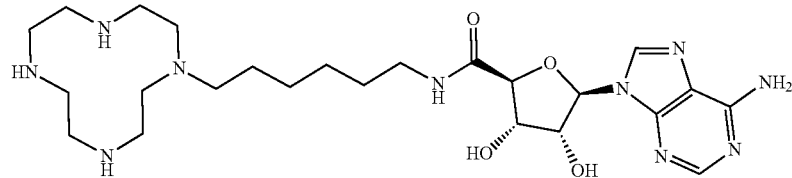 [SMILES: Nc1ncnc2c1ncn2[C@@H]1O[C@H](C(=O)NCCCCCCN2CCNCCNCCNCC2)[C@@H](O)[C@H]1O]

$^1$H NMR (400 MHz, CD$_3$OD) δ 1.19-1.59 (m, 6H), 2.55-2.74 (m, 2H), 2.78-3.13 (m, 12H), 3.17-3.29 (m, 6H), 4.22-4.50 (m, 2H), 4.53-4.72 (m, 1H), 5.94-6.17 (m, 1H), 8.24-8.41 (m, 1H), 8.43-8.63 (m, 1H).

(2S,3S,4R,5R)—N-(6-(1,4,7,10-tetraazacyclododecan-1-yl)hexyl)-5-(6-amino-9H-purin-9-yl)-3,4-dihydroxytetrahydrofuran-2-carboxamide, zinc(II) trifluromethanesulfonate (1.5.A.Zn)

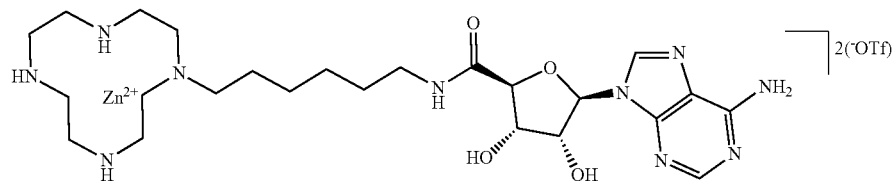 [SMILES: Nc1ncnc2c1ncn2[C@@H]1O[C@H](C(=O)NCCCCCCN2CCNCCNCCNCC2)[C@@H](O)[C@H]1O ; [Zn+2]]

Metal coordination assessed visually.

(2S,3S,4R,5R)—N-(6-(1,4,7,10-tetraazacyclododecan-1-yl)hexyl)-5-(6-amino-9H-purin-9-yl)-3,4-dihydroxytetrahydrofuran-2-carboxamide, copper(II) trifluromethanesulfonate (1.5.A.Cu)

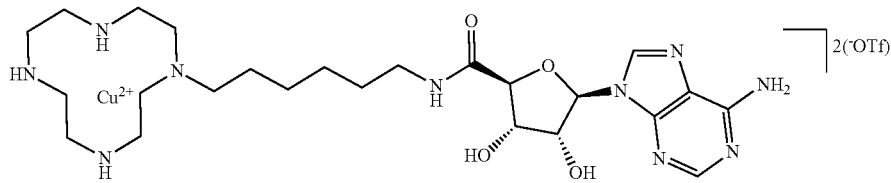

Metal coordination assessed visually.

(3aS,4S,6R,6aR)-6-(6-amino-9H-purin-9-yl)-N-(2,2-dimethoxyethyl)-2,2-dimethyltetrahydrofuro[3,4-d][1,3]dioxole-4-carboxamide

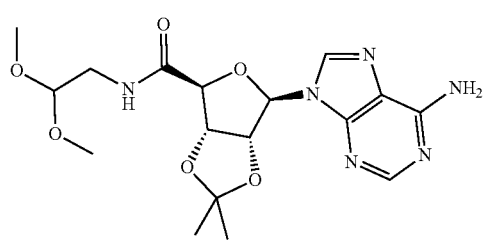 [SMILES: COC(CNC(=O)[C@H]1O[C@@H](n2cnc3c(N)ncnc32)[C@@H]2OC(C)(C)O[C@@H]21)OC]

$^1$H NMR (400 MHz, CDCl$_3$) δ 1.21 (s, 3H, COC(CH$_3$)$_2$), 1.43 (s, 3H, COC(CH$_3$)$_2$), 3.02 (s, 3H, OCH$_3$), 3.03 (s, 3H, OCH$_3$), 3.81 (t, J=5.47 Hz, 1H, CH$_2$CH(OCH$_3$)$_2$), 4.54 (d, J=1.51 Hz, 1H, 4'H), 5.22 (dd, J=6.54 and 2.12 Hz, 1H, 3'H), 5.31 (dd, J=6.14 and 1.79 Hz, 6.04 (d, J=2.17 Hz, 1H, 1'H), 6.77 (s, 2H, NH$_2$), 8.11 (s, 1H, C$_{ar}$H).

(2S,3S,4R,5R)—N-(2-(1,4,7,10-tetraazacyclododecan-1-yl)ethyl)-5-(6-amino-9H-purin-9-yl)-3,4-dihydroxytetrahydrofuran-2-carboxamide (1.1A.L)

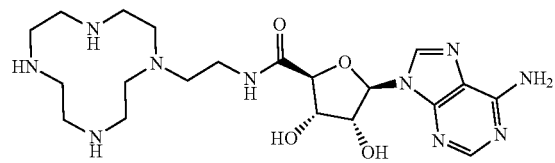 [SMILES: Nc1ncnc2c1ncn2[C@@H]1O[C@H](C(=O)NCCN2CCNCCNCCNCC2)[C@@H](O)[C@H]1O]

$^1$H NMR (400 MHz, CD$_3$OD) δ 2.71 (t, J=5.28 Hz, 2H, CH$_2$CH$_2$NH), 2.83-3.23 (m, 16H, 8× cyclen CH$_2$), 3.32-3.39 (CH$_2$CH$_2$NH), 3.48-3.58 (CH$_2$CH$_2$NH), 4.49 (t, J=4.20 Hz, 1H, 3'H), 4.52 (d, J=3.98 Hz, 1H, 4'H), 4.68 (t, J=5.08 Hz, 1H, 2'H), 6.17 (d, J=5.29 Hz, 1H, 1'H), 8.47 (s, 1H, C2-H), 8.69 (s, 1H, C8-H).

(2S,3S,4R,5R)—N-(2-(1,4,7,10-tetraazacyclododecan-1-yl)ethyl)-5-(6-amino-9H-purin-9-yl)-3,4-dihydroxytetrahydrofuran-2-carboxamide, zinc(II) trifluoromethanesulfonate (1.1.A.Zn)

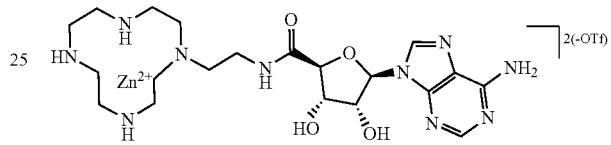

(2S,3S,4R,5R)—N-(2-(1,4,7,10-tetraazacyclododecan-1-yl)ethyl)-5-(6-amino-9H-purin-9-yl)-3,4-dihydroxytetrahydrofuran-2-carboxamide, copper(II) trifluromethanesulfonate (1.1.A.Cu)

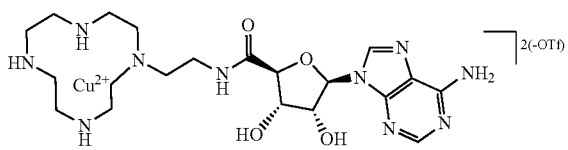

Metal coordination assessed visually.

(2S,3S,4R,5R)—N-(2-(1,4,8,11-tetraazacyclotetradecan-1-yl)ethyl)-5-(6-amino-9H-purin-9-yl)-3,4-dihydroxytetrahydrofuran-2-carboxamide (1.1.Cy.A.L)

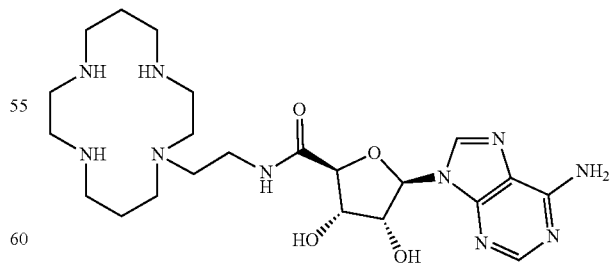

$^1$H NMR (400 MHz, CD$_3$OD) δ 1.83-1.88 (m, 2H), 1.94-1.99 (m, 2H), 2.65-2.88 (m, 12H), 3.13 (bs, 4H), 3.43-3.49 (m, 4H), 4.47 (t, J=4.29 Hz, 1H), 4.53 (d, J=3.43 Hz, 1H), 4.73 (t, J=5.58 Hz, 1H), 6.13 (d, J=6.10 Hz, 1H), 8.36 (s, 1H), 8.50 (s, 1H).

(2S,3S,4R,5R)—N-(2-(1,4,8,11-tetraazacyclotetradecan-1-yl)ethyl)-5-(6-amino-9H-purin-9-yl)-3,4-dihydroxytetrahydrofuran-2-carboxamide, zinc(II) trifluoromethanesulfonate (1.1.Cy.A.Zn)

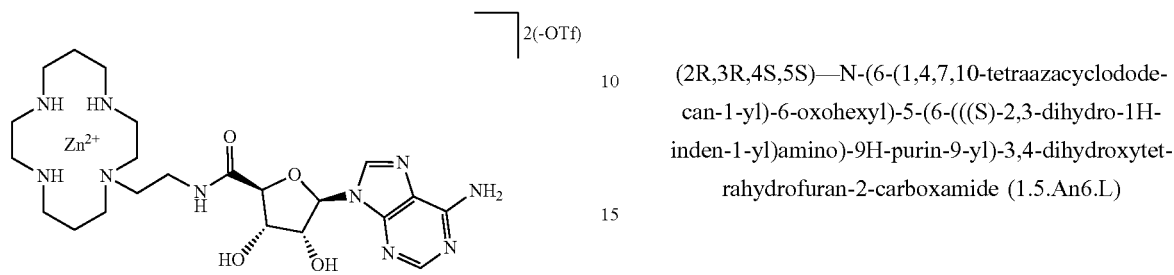

Metal coordination was assessed visually. For ligand characterization, see 1.1.Cy.A.L.

(2R,3R,4S,5S)—N-(6-(1,4,7,10-tetraazacyclododecan-1-yl)-6-oxohexyl)-5-(6-(((S)-2,3-dihydro-1H-inden-1-yl)amino)-9H-purin-9-yl)-3,4-dihydroxytetrahydrofuran-2-carboxamide (1.5.An6.L)

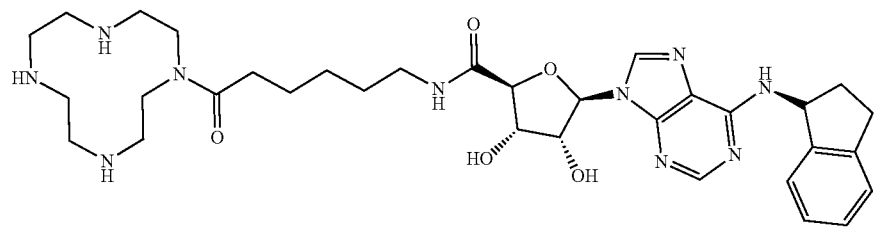

¹H NMR (400 MHz, CD₃OD) δ 1.36-1.51 (m, 2H), 1.58-1.75 (m, 4H), 1.97-2.12 (m, 1H), 2.34-2.52 (m, 2H), 2.60-3.02 (m, 13H), 3.03-3.17 (m, 2H), 3.33-3.46 (m, 2H), 3.46-3.63 (m, 4H), 4.33 (d, J=4.7 Hz, 1H), 4.48 (s, 1H), 4.78 (dd, J=7.5, 4.8 Hz, 1H), 6.02 (d, J=7.6 Hz, 1H), 7.06-7.37 (m, 4H), 8.19-8.32 (m, 2H), 8.36 (br. s).

(2S,3S,4R,5R)-5-(6-(((S)-2,3-dihydro-1H-inden-1-yl)amino)-9H-purin-9-yl)-3,4-dihydroxy-N-(6-oxo-6-(1,4,7,10-tetraazacyclododecan-1-yl)hexyl)tetrahydrofuran-2-carboxamide, zinc(II) trifluoromethanesulfate (1.5.An6.Zn)

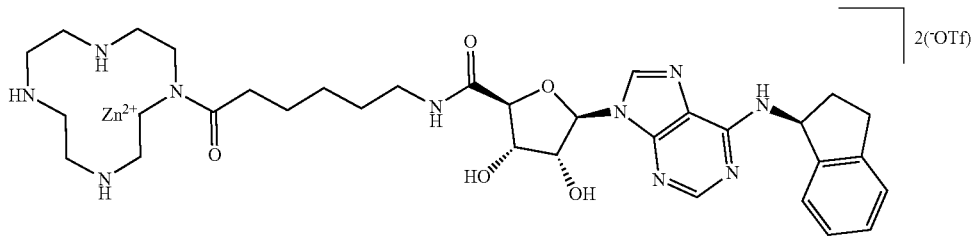 [SMILES: O=C(NCCCCCC(=O)N1CCNCCNCCNCC1)[C@H]1O[C@@H](n2cnc3c(N[C@H]4CCc5ccccc54)ncnc32)[C@H](O)[C@@H]1O ; [Zn+2]]

Metal coordination assessed visually. For characterization of ligand, see 1.5.An6.L.

(2S,3S,4R,5R)-5-(6-(((S)-2,3-dihydro-1H-inden-1-yl)amino)-9H-purin-9-yl)-3,4-dihydroxy-N-(6-oxo-6-(1,4,7,10-tetraazacyclododecan-1-yl)hexyl)tetrahydrofuran-2-carboxamide, copper(II) trifluoromethanesulfonate (1.5.An6.Cu)

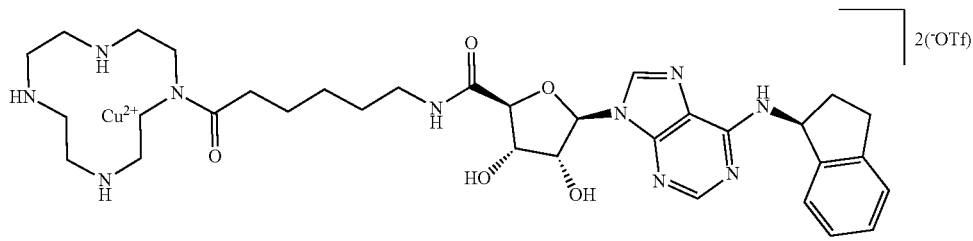

Metal coordination assessed visually. For characterization of ligand, see 1.5.An6.L.

Tri-tert-butyl 10-(11-aminoundecanoyl)-1,4,7,10-tetraazacyclododecane-1,4,7-tricarboxylate

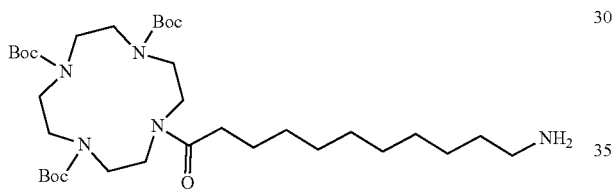

$^1$H NMR (400 MHz, CDCl$_3$) δ 1.09-1.19 (m, 14H), 1.23-1.35 (m, 27H), 1.44-1.57 (m, 2H), 2.14 (t, J=7.6 Hz, 2H), 2.53 (t, J=7.0 Hz, 2H), 3.02-3.52 (m, 16H); $^{13}$C NMR (100 MHz, CDCl$_3$) δ 25.06, 26.55, 28.18, 29.10, 29.14, 29.19, 29.22, 33.40, 41.88, 49.22, 49.57, 50.11, 51.07, 79.71, 79.83, 80.00, 155.07, 157.01.

Tri-tert-butyl 10-(11-((3aS,4S,6R,6aR)-6-(6-amino-9H-purin-9-yl)-2,2-dimethyltetrahydrofuro[3,4-d][1,3]dioxole-4-carboxamido)undecanoyl)-1,4,7,10-tetraazacyclododecane-1,4,7-tricarboxylate

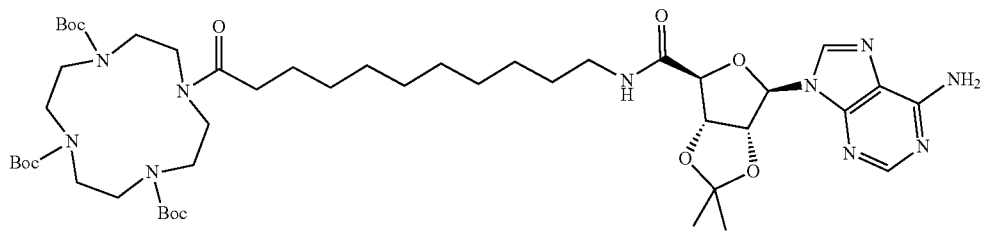 [SMILES: CC(C)(C)OC(=O)N1CCN(C(=O)CCCCCCCCCCNC(=O)[C@H]2O[C@@H](n3cnc4c(N)ncnc43)[C@@H]3OC(C)(C)O[C@@H]32)CCN(C(=O)OC(C)(C)C)CCN(C(=O)OC(C)(C)C)CC1]

$^1$H NMR (400 MHz, CDCl$_3$) δ 0.90-1.03 (m, 4H), 1.11-1.35 (m, 10H), 1.39 (s, 3H), 1.48 (s, 27H), 1.57 (s, 3H), 1.57-1.67 (m, 2H), 2.34 (t, J=7.6 Hz, 2H), 2.74-2.88 (m, 2H), 3.34-3.62 (m, 16H), 4.63 (d, J=1.8 Hz, 1H), 5.47 (dd, J=6.1, 1.4 Hz, 1H), 5.59 (dd, J=6.1, 1.9 Hz, 1H), 6.34 (d, J=1.4 Hz, 1H), 8.16 (s, 1H), 8.24 (s, 1H).

(2S,3S,4R,5R)-5-(6-amino-9H-purin-9-yl)-3,4-dihydroxy-N-(11-oxo-11-(1,4,7,10-tetraazacyclododecan-1-yl)undecyl)tetrahydrofuran-2-carboxamide (1.10.L)

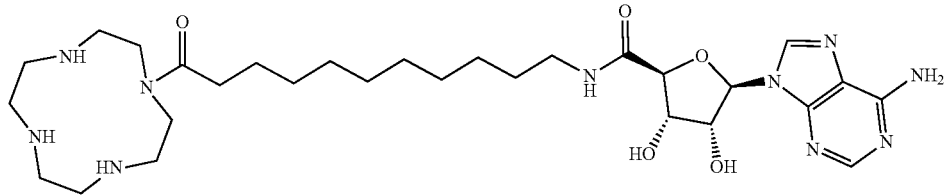 [SMILES: Nc1ncnc2c1ncn2[C@@H]1O[C@H](C(=O)NCCCCCCCCCCC(=O)N2CCNCCNCCNCC2)[C@@H](O)[C@H]1O]

$^1$H NMR (400 MHz, CD$_3$OD) δ 1.17-1.39 (m, 12H, CH$_2$), 1.54 (m, 4H, CH$_2$), 2.34-2.47 (m, 2H, CH$_2$), 3.07-3.33 (m, 16H, cylen-CH$_2$ & CH$_2$), 3.72 (br. s, 4H, cyclen-CH$_2$), 4.38 (dd, J=4.8, 2.5 Hz, 1H, 4'H), 4.50 (d, J=2.4 Hz, 1H, 3'H), 4.72 (dd, J=6.6, 4.7 Hz, 1H, 2'H), 6.13 (d, J=6.7 Hz, 1H, 1'H), 8.39 (s, 1H, C2-H), 8.61 (s, 1H, C8-H).

(2S,3S,4R,5R)-5-(6-amino-9H-purin-9-yl)-3,4-dihydroxy-N-(11-oxo-11-(1,4,7,10-tetraazacyclododecan-1-yl)undecyl)tetrahydrofuran-2-carboxamide, zinc (II) trifluromethanesulfonate (1.10.Zn)

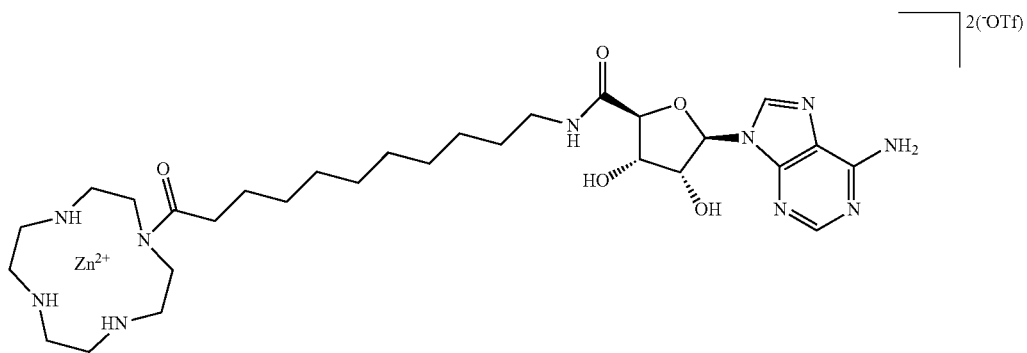

Metal coordination assessed visually. For characterization of ligand, see above.

(2S,3S,4R,5R)-5-(6-amino-9H-purin-9-yl)-3,4-dihydroxy-N-(11-oxo-11-(1,4,7,10-tetraazacyclododecan-1-yl)undecyl)tetrahydrofuran-2-carboxamide, copper (II) trifluromethanesulfonate (1.10.Cu)

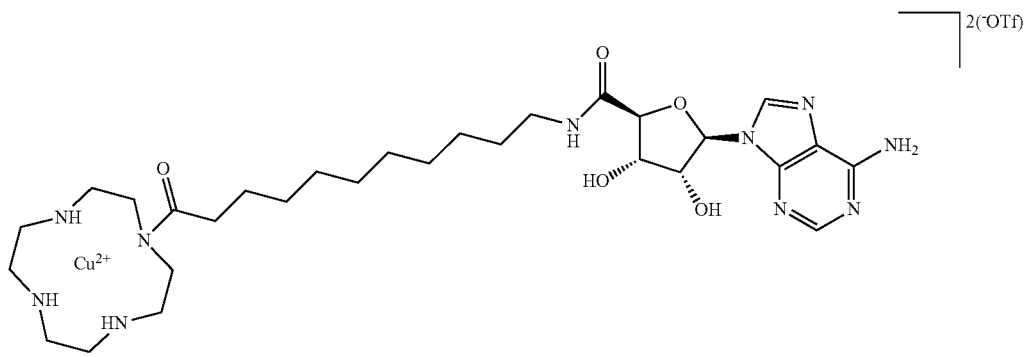

Metal coordination assessed visually. For characterization of ligand, see above.

(3aS,4S,6R,6aR)-6-(6-chloro-9H-purin-9-yl)-2,2-dimethyltetrahydrofuro[3,4-d][1,3]dioxole-4-carboxylic acid

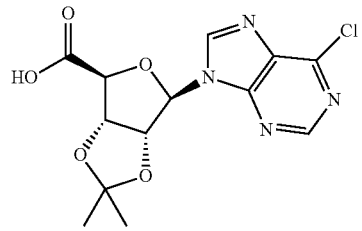 [SMILES: CC1(C)O[C@@H]2[C@H](O1)[C@@H](C(=O)O)O[C@H]2n1cnc2c(Cl)ncnc21]

$^1$H NMR (400 MHz, CD$_3$OD) δ 1.41 (s, 3H), 1.58 (s, 3H), 4.81 (d, J=1.1 Hz, 1H), 5.59-5.75 (m, 2H), 6.47 (s, 1H), 8.67 (s, 1H), 8.69 (s, 1H); $^{13}$C NMR (100 MHz, CD$_3$OD) δ 20.76, 25.22, 26.88, 85.19, 85.80, 88.17, 93.05, 114.84, 132.52, 148.33, 151.38, 152.69, 152.90, 172.83.

(2S,3S,4R,5R)-5-(6-chloro-9H-purin-9-yl)-3,4-dihydroxy-N-(6-oxo-6-(1,4,7,10-tetraazacyclododecan-1-yl)hexyl)tetrahydrofuran-2-carboxamide (1.5.Cl6.L)

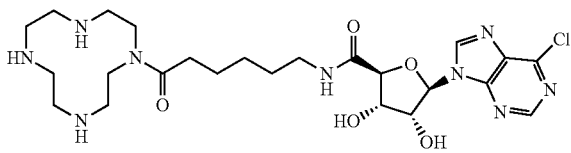 [SMILES: O=C(NCCCCCC(=O)N1CCNCCNCCNCC1)[C@H]1O[C@@H](n2cnc3c(Cl)ncnc32)[C@H](O)[C@@H]1O]

$^1$H NMR (400 MHz, CD$_3$OD) δ 1.30-1.41 (m, 2H), 1.48-1.70 (m, 4H), 2.44 (t, J=7.5 Hz, 2H), 3.11-3.26 (m, 12H), 3.26-3.36 (m, 2H), 3.72 (br. s, 4H), 4.47 (dd, J=4.8, 2.7 Hz, 1H), 4.49 (d, J=2.7 Hz, 1H), 4.82 (dd, J=6.6, 4.7 Hz, 1H), 6.20 (d, J=6.6 Hz, 1H), 8.79 (s, 1H), 8.86 (s, 1H).

(2S,3S,4R,5R)-5-(6-chloro-9H-purin-9-yl)-3,4-dihydroxy-N-(6-oxo-6-(1,4,7,10-tetraazacyclododecan-1-yl)hexyl)tetrahydrofuran-2-carboxamide, zinc(II) trifluromethanesulfonate (1.5.Cl6.Zn)

Metal coordination assessed visually. For characterization of ligand, see above.

(2S,3S,4R,5R)-3,4-dihydroxy-5-(6-hydroxy-9H-purin-9-yl)-N-(6-oxo-6-(1,4,7,10-tetraazacyclododecan-1-yl)hexyl)tetrahydrofuran-2-carboxamide (1.5.OH6.L)

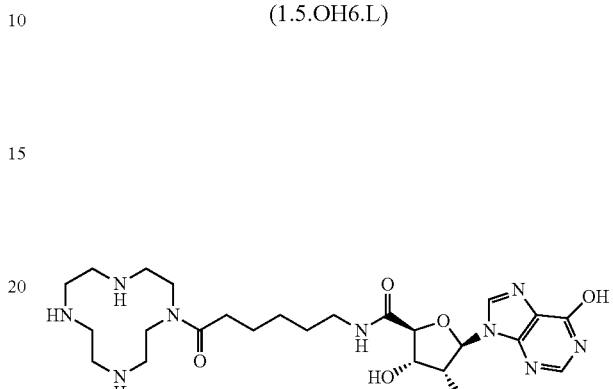

$^1$H NMR (400 MHz, CD$_3$OD) δ 1.07-1.30 (m, 2H, COCH$_2$CH$_2$CH$_2$CH$_2$CH$_2$NH), 1.36-1.60 (m, 4H, COCH$_2$CH$_2$CH$_2$CH$_2$CH$_2$NH), 2.39 (t, J=7.49 Hz, 2H, COCH$_2$CH$_2$CH$_2$CH$_2$CH$_2$NH), 3.02-3.42 (m, 2H, COCH$_2$CH$_2$CH$_2$CH$_2$CH$_2$NH; 12H, 6× cyclen CH$_2$), 3.56-3.90 (m, 4H, 2× cyclen CH$_2$), 4.48 (d, J=2.55 Hz, 1H, 4'H), 4.55 (dd, J=5.03 and 2.97 Hz, 1H, 3'H), 4.77 (t, J=5.49 Hz, 1H, 2'H), 6.12 (d, J=5.86 Hz, 1H, 1'H), 8.17 (s, 1H, C2-H), 8.43 (s, 1H, C8-H); $^{13}$C NMR (100 MHz, CD$_3$OD) δ 25.52, 27.37, 30.21, 34.79, 39.78, 44.09, 44.76, 45.67, 46.23, 46.45, 46.99, 47.12, 74.71, 74.75, 85.97, 90.74, 142.26, 147.13, 149.84, 159.07, 172.01, 172.10, 177.82 (note: some TFA peaks identified in carbon; not reported).

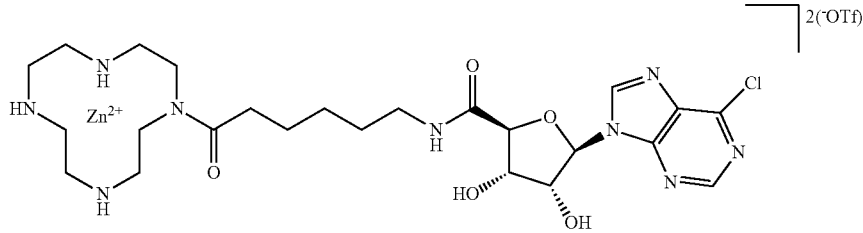 [SMILES: O=C(NCCCCCC(=O)N1CCNCCNCCNCC1)[C@H]1O[C@@H](n2cnc3c(Cl)ncnc32)[C@H](O)[C@@H]1O ; [Zn+2]]

| (2S,3S,4R,5R)-3,4-dihydroxy-5-(6-hydroxy-9H-purin-9-yl)-N-(6-oxo-6-(1,4,7,10-tetraazacyclodode-can-1-yl)hexyl)tetrahydrofuran-2-carboxamide, zinc (II) trifluromethanesulfonate (1.5.O6.Zn) | 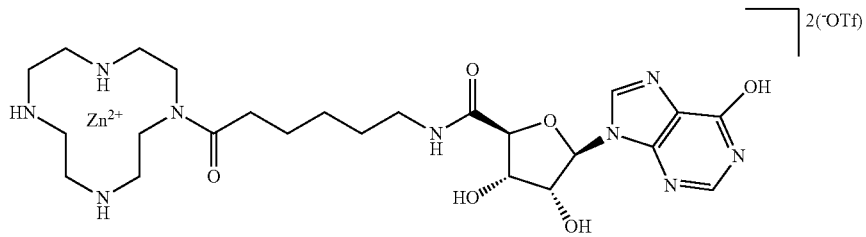 |
|---|---|
| Metal coordination assessed visually. For characterization of ligand, see above. | |
| (2S,3S,4R,5R)-3,4-dihydroxy-5-(6-hydroxy-9H-purin-9-yl)-N-(6-oxo-6-(1,4,7,10-tetraazacyclodode-can-1-yl)hexyl)tetrahydrofuran-2-carboxamide, copper(II) trifluromethanesulfonate (1.5.OH6.Cu) | 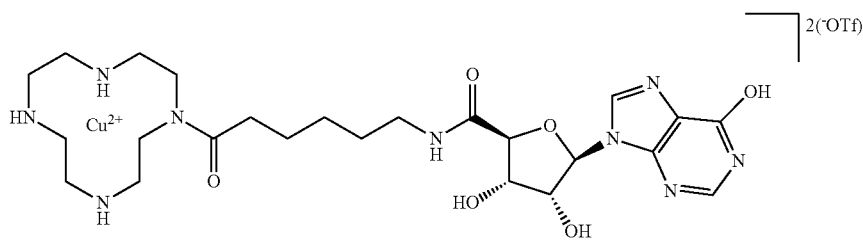 |
| Metal coordination assessed visually. For characterization of ligand, see above. | |
| Tri-tert-butyl 10-(6-(((3aS,4S,6R,6aR)-6-(6-(benzy-lamino)-9H-purin-9-yl)-2,2-dimethyltetrahydrofuro[3,4-d][1,3]dioxole-4-carboxamido)hexanoyl)-1,4,7,10-tetraazacyclododecane-1,4,7-tricarboxylate | 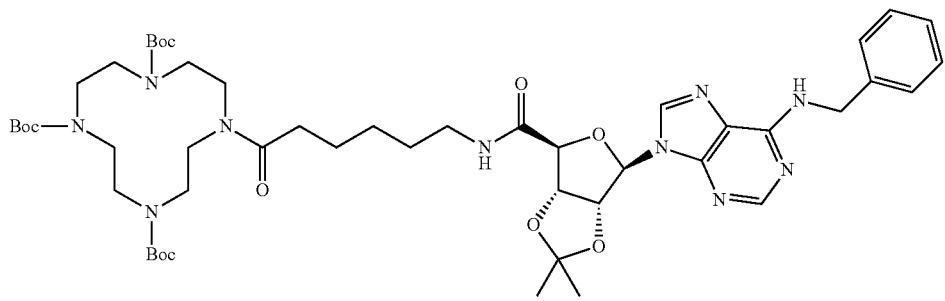 [SMILES: CC(C)(C)OC(=O)N1CCN(C(=O)CCCCCNC(=O)[C@H]2O[C@@H](n3cnc4c(NCc5ccccc5)ncnc43)[C@@H]3OC(C)(C)O[C@@H]32)CCN(C(=O)OC(C)(C)C)CCN(C(=O)OC(C)(C)C)CC1] |

$^1$H NMR (400 MHz, CDCl$_3$) δ 0.95-1.08 (m, 4H, COCH$_2$CH$_2$CH$_2$CH$_2$CH$_2$NH), 1.36-1.41 (m, 2H from COCH$_2$CH$_2$CH$_2$CH$_2$CH$_2$NH, 3H from COC(CH$_3$)$_2$), 1.43-1.51 (m, 27H, 3×Boc), 1.56 (s, 3H, COC(CH$_3$)$_2$), 2.19-2.30 (m, 2H, COCH$_2$CH$_2$CH$_2$CH$_2$CH$_2$NH), 2.75-2.85 (m, 2H, COCH$_2$CH$_2$CH$_2$CH$_2$CH$_2$NH), 3.28-3.61 (m, 16H, 8× cyclen CH$_2$), 4.62 (d, J=1.42 Hz, 1H, 4'H), 5.45 (d, J=6.09 Hz, 1H, 3'H), 5.48 (s, 2H, Bz-CH$_2$), 5.59 (dd, J=6.04 Hz and 1.20 Hz, 1H, 2'H), 6.32 (s, 1H, 1'H), 7.19-7.24 (m, 1H, Bz-H), 7.28 (t, J=6.89 Hz, 2H, Bz-H), 7.37 (d, J=7.35 Hz, 2H, Bz-H), 8.16 (s, 1H, C2-H), 8.22 (s, 1H, C8-H).

(2S,3S,4R,5R)-5-(6-(benzylamino)-9H-purin-9-yl)-3,4-dihydroxy-N-(6-oxo-6-(1,4,7,10-tetraazacyclododecan-1-yl)hexyl)tetrahydrofuran-2-carboxamide (1.5.Bz6.L)

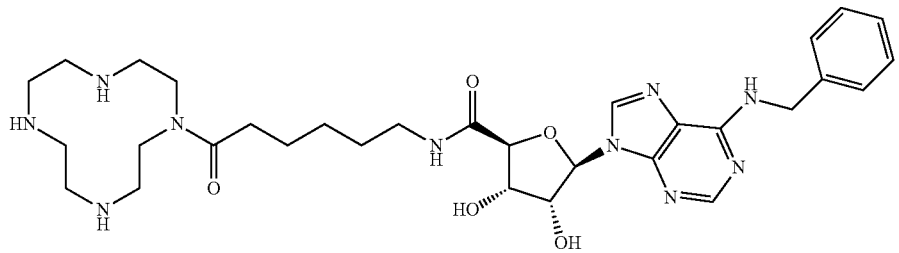 [SMILES: O=C(NCCCCCC(=O)N1CCNCCNCCNCC1)[C@H]1O[C@@H](n2cnc3c(NCc4ccccc4)ncnc32)[C@H](O)[C@@H]1O]

¹H NMR (400 MHz, CD₃OD) δ 1.35-1.47 (m, 2H, COCH₂CH₂CH₂CH₂CH₂NH), 1.52-1.74 (m, 4H, COCH₂CH₂CH₂CH₂CH₂NH), 2.47 (t, J=7.42 Hz, 2H, COCH₂CH₂CH₂CH₂CH₂NH), 3.16-3.25 (m, 12H, 6× cyclen CH₂), 3.62-3.78 (m, 4H, 2× cyclen CH₂), 4.37 (bs, 1H, 4'H), 4.54 (bs, 1H, 3'H), 4.66 (bs, 1H, 2'H), 6.13 (d, J=4.88 Hz, 1H, 1'H), 7.27-7.46 (m, 5H, Bz-H), 8.43-8.52 (m, 2H, C2-H and C8-H) (note: Bz-CH₂ and COCH₂CH₂CH₂CH₂CH₂NH are covered by water and methanol residual peaks, respectively).

Tri-tert-butyl 10-(6-((3aS,4S,6R,6aR)-2,2-dimethyl-6-(6-((thiophen-2-ylmethyl)amino)-9H-purin-9-yl)tetrahydrofuro[3,4-d][1,3]dioxole-4-carboxamido)hexanoyl)-1,4,7,10-tetraazacyclododecane-1,4,7-tricarboxylate

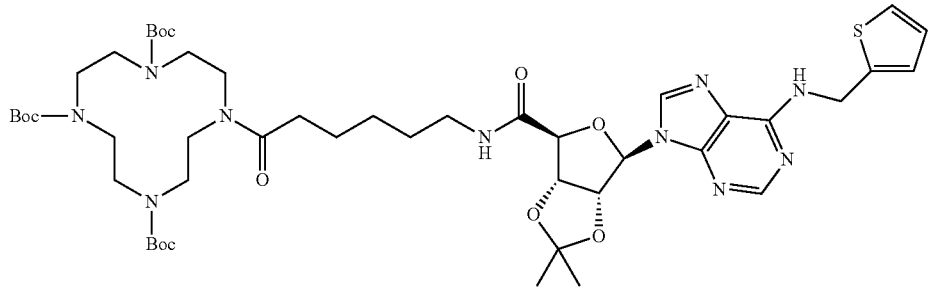 [SMILES: CC(C)(C)OC(=O)N1CCN(C(=O)CCCCCNC(=O)[C@H]2O[C@@H](n3cnc4c(NCc5cccs5)ncnc43)[C@@H]3OC(C)(C)O[C@@H]32)CCN(C(=O)OC(C)(C)C)CCN(C(=O)OC(C)(C)C)CC1]

¹H NMR (400 MHz, CD₃OD) δ 0.91-1.07 (m, 4H, COCH₂CH₂CH₂CH₂CH₂NH), 1.29-1.33 (m, 2H, COCH₂CH₂CH₂CH₂CH₂NH), 1.41 (s, 3H, COC(CH₃)₂), 1.45-1.50 (m, 27H, 3×Boc), 1.58 (s, 3H, COC(CH₃)₂), 2.26 (t, J=7.53 Hz, 2H, COCH₂CH₂CH₂CH₂CH₂NH), 2.76-2.83 (m, 2H, COCH₂CH₂CH₂CH₂CH₂NH), 3.35-3.61 (m, 16H, 8× cyclen CH₂), 4.63 (s, 1H, 4'H), 4.97 (bs, 2H, thiophene-CH₂), 5.47-5.52 (m, 1H, 3'H), 5.64 (dd, J=5.90 and 1.52 Hz, 1H, 2'H), 6.34 (s, 1H, 1'H), 6.94 (dd, J=5.44 and 3.91 Hz, 1H, thiophene-H), 7.07 (d, J=3.04 Hz, 1H, thiophene-H), 7.26 (d, J=7.25 Hz, 1H, thiophene-H), 8.19 (s, 1H, C2-H), 8.27 (s, 1H, C8-H).

(3aS,4S,6R,6aR)-6-(6-(((S)-2,3-dihydro-1H-inden-1-yl)amino)-9H-purin-9-yl)-2,2-dimethyltetrahydrofuro[3,4-d][1,3]dioxole-4-carboxylic acid

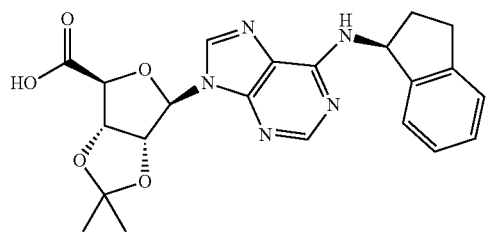 [SMILES: CC1(C)O[C@@H]2[C@H](O1)[C@@H](C(=O)O)O[C@H]2n1cnc2c(N[C@H]3CCc4ccccc43)ncnc21]

¹H NMR (400 MHz, CD₃Cl) δ 1.41 (s, 3H), 1.60 (s, 3H), 2.42-2.70 (m, 2H), 2.87 (m, 1H), 2.95-3.10 (m, 1H), 4.76 (s, 1H), 5.20-5.72 (m, 2H), 6.19 (s, 1H), 7.02-7.39 (m, 4H), 8.06 (bs, 1H), 8.34 (bs, 1H), 12.11 (s, 1H, COOH).

(2S,3S,4R,5R)-5-(6-(((S)-2,3-dihydro-1H-inden-1-yl)amino)-9H-purin-9-yl)-3,4-dihydroxy-N-(2-oxo-2-(1,4,7,10-tetraazacyclododecan-1-yl)ethyl)tetrahydrofuran-2-carboxamide (1.1.An6.L)

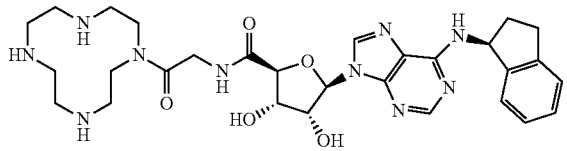 [SMILES: O=C(NCC(=O)N1CCNCCNCCNCC1)[C@H]1O[C@@H](n2cnc3c(N[C@H]4CCc5ccccc54)ncnc32)[C@H](O)[C@@H]1O]

¹H NMR (400 MHz, CD₃OD) δ 2.03-2.21 (m, 1H), 2.65-2.83 (m, 1H), 2.92-3.05 (m, 1H), 3.08-3.29 (m, 12H), 3.62-3.93 (m, 4H), 4.03-4.20 (m, 1H), 4.24-4.35 (m, 1H), 4.43-4.56 (m, 1H), 4.59 (d, J=2.6 Hz, 1H), 4.75 (dd, J=6.8, 4.8 Hz, 1H), 6.13-6.30 (m, 1H), 6.69 (bs, 1H), 7.22 (t, J=7.3 Hz, 2H), 7.26-7.36 (m, 2H), 8.50 (bs, 1H), 8.73 (bs, 1H).

Ethyl 4-(6-amino-9H-purin-9-yl)butanoate

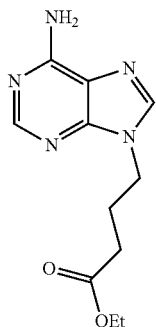 [SMILES: CCOC(=O)CCCn1cnc2c(N)ncnc21]

¹H NMR (400 MHz, Chloroform-d) δ 8.28 (s, 1H, CH), 7.77 (s, 1H, CH), 6.75 (s, 2H, NH₂), 4.22 (t, J=7.0 Hz, 2H, NCH₂), 4.05 (q, J=7.1 Hz, 2H, OCH₂), 2.28 (t, J=7.1 Hz, 2H, CH₂COOEt), 2.16 (p, J=7.0 Hz, 2H, CH₂CH₂CH₂), 1.16 (t, J=7.2 Hz, 3H, CH₃). ¹³C NMR (101 MHz, CDCl₃) δ 172.41, 156.02, 152.95, 150.01, 140.34, 119.63, 60.68, 42.90, 30.87, 25.25, 14.16. HRMS (ESI-TOF) m/z: [M+H]⁺ Calcd for C₁₁H₁₆N₅ 250.1299; Found 250.1297.

4-(6-amino-9H-purin-9-yl)butanoic acid

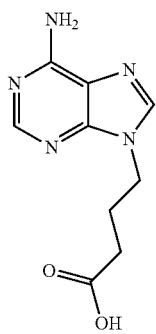

¹H NMR (400 MHz, DMSO-d₆) δ 12.18 (br. s, 1H, COOH), 8.34 (s, 1H, CH), 8.33 (s, 1H, CH), 8.22 (br. s, 2H, NH₂), 4.22 (t, J=7.0 Hz, 2H, NCH₂), 2.24 (t, J=7.4 Hz, 2H, CH₂COOH), 2.04 (p, J=7.0 Hz, 2H, CH₂CH₂CH₂). HRMS (ESI-TOF) m/z: [M+H]⁺ Calcd for C₉H₁₂N₅O₂ 222.0986; Found 222.0990.

tri-tertbutyl 10-(6-(4-(6-amino-9H-purin-9-yl)butanamido)hexanoyl)-1,4,7,10-tetraazacyclododecane-1,4,7-tricarboxylate

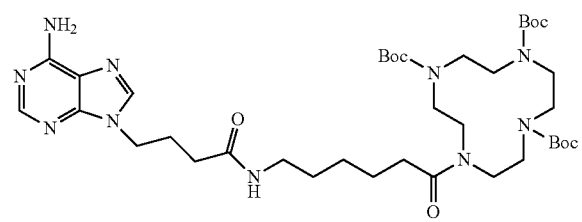 [SMILES: CC(C)(C)OC(=O)N1CCN(C(=O)CCCCCNC(=O)CCCn2cnc3c(N)ncnc32)CCN(C(=O)OC(C)(C)C)CCN(C(=O)OC(C)(C)C)CC1]

¹H NMR (400 MHz, Chloroform-d) δ 8.31 (s, 1H, CH), 7.83 (s, 1H, CH), 6.83 (br. s, 1H, NH), 6.09 (br.s, 2H, NH₂), 4.26 (t, J=5.7 Hz, 2H, NCH₂), 3.61-3.26 (m, 16H, cyclen-CH₂), 3.29-3.17 (q, J=6.7 Hz, 2H, NHCH₂), 2.28 (t, J=7.2 Hz, 2H, CH₂CONH), 2.23-2.10 (m, 4H, CH₂), 1.70-1.57 (m, 2H, CH₂), 1.57-1.46 (m, 2H, CH₂), 1.46-1.39 (m, 27H, CH₃), 1.39-1.29 (m, 2H, CH₂). ¹³C NMR (101 MHz, CDCl₃) δ 171.62, 157.41, 155.69, 155.50, 152.79, 150.26, 140.97, 119.68, 80.52, 80.43, 80.23, 51.54, 50.40, 49.70, 43.04, 39.27, 32.98, 29.23, 28.59, 28.57, 26.75, 24.73. HRMS (ESI-TOF) m/z: [M+H]⁺ Calcd for C₃₈H₆₅N₁₀O₈ 789.4981; Found 789.4985.

N-(6-(1,4,7,10-tetraazacyclododecan-1-yl)-6-oxohexyl)-4-(6-amino-9H-purin-9-yl)butanamide (2.1)

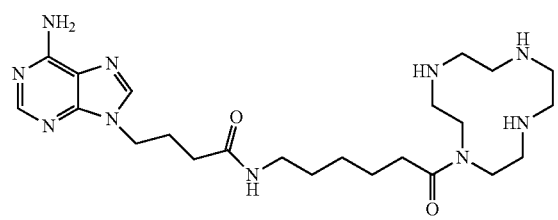 [SMILES: Nc1ncnc2c1ncn2CCCC(=O)NCCCCCC(=O)N1CCNCCNCCNCC1]

¹H NMR (400 MHz, Methanol-d₄) δ 8.20 (s, 1H, CH), 8.12 (s, 1H, CH), 4.27 (t, J=6.4 Hz, 2H), 3.71-3.32 (m, 5H), 3.11 (t, J=6.8 Hz, 2H), 3.01-2.57 (m, 11H), 2.45 (t, J=7.5 Hz) & 2.39 (t, J=7.4 Hz) (2H), 2.26-2.12 (m, 4H), 1.61 (p, J=7.6 Hz, 2H), 1.47 (p, J=7.2 Hz, 2H), 1.39-1.29 (m, 2H). ¹³C NMR (101 MHz, MeOD) δ 177.28, 174.34, 157.32, 153.70, 150.78, 142.78, 120.05, 54.81, 49.64, 49.42, 49.21, 49.00, 48.79, 48.57, 48.36, 46.80, 45.63, 44.35, 40.25, 34.56, 33.79, 30.11, 27.67, 27.23, 26.08. HRMS (ESI-TOF) m/z: [M+H]⁺ Calcd for C₂₃H₄₁N₁₀O₂ 489.3408; Found 489.3410.

75 tri-tertbutyl 10-(6-(1H-imidazole-1-carboxamido)hexanoyl)-1,4,7,10-tetraazacyclododecane-1,4,7-tricarboxylate

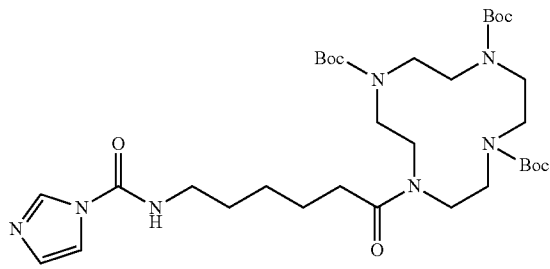 [SMILES: CC(C)(C)OC(=O)N1CCN(C(=O)CCCCCNC(=O)n2ccnc2)CCN(C(=O)OC(C)(C)C)CCN(C(=O)OC(C)(C)C)CC1]

¹H NMR (400 MHz, Chloroform-d) δ 8.26 (s, 1H, CH), 7.81 (s, 1H, NH), 7.59 (s, 1H, CH), 6.98 (s, 1H, CH), 3.64-3.21 (m, 18H, Cyclen-CH₂, CH₂), 2.32 (t, J=6.5 Hz, 2H, CH₂), 1.76-1.52 (m, 4H, 2 CH₂), 1.52-1.23 (m, 29H, CH₂, 9 CH₃). ¹³C NMR (101 MHz, CDCl₃) δ 157.15 (NH CON), 155.30 (NCOCH₂), 149.09 (COC(CH₃)₃), 136.03 (CH), 129.69 (CH), 116.33 (CH), 80.43 (COC(CH₃)₃), 80.38 (COC(CH₃)₃), 80.15 (COC(CH₃)₃), 53.33 (cyclen-CH₂), 51.39 (cyclen-CH₂), 50.16 (cyclen-CH₂), 49.84 (cyclen-CH₂), 49.32 (cyclen-CH₂), 48.21 (cyclen-CH₂), 39.55 (CH₂), 32.29 (CH₂), 28.38 (CH₃), 28.33 (CH₃), 27.61 (CH₃), 25.62 (CH₂), 23.80 (CH₂), 22.68 (CH₂). MS (ESI): [M+H]⁺=680; [M+Na]⁺=702; [M+K]⁺=718.

tert-butyl (2-(6-amino-9H-purin-9-yl)ethyl)-azanecarboxylate

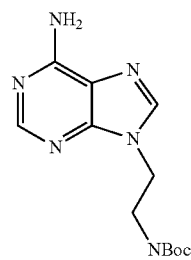

¹H NMR (400 MHz, Methanol-d₄) δ 8.19 (s, 1H, CH), 8.02 (s, 1H, CH), 4.86 (s, 2H, NH₂), 4.29 (t, J=5.9 Hz, 2H, NCH₂), 3.46 (t, J=5.7 Hz, 2H, NHCH₂), 1.31 (s, 7H) & 1.11 (s, 2H) (CH₃). ¹³C NMR (101 MHz, MeOD) δ 158.20 (NC$_{ar}$N), 157.27 (CO), 153.64 (CH), 150.93 (CNH₂), 142.95 (CH), 120.06 (NC$_{ar}$C), 80.25 (C), 44.90 (CH₂), 40.98 (CH₂), 28.61 & 28.19 (CH₃). MS (ESI): [M+H]⁺=279; [M+Na]⁺=301; [M+K]⁺=318.

76

9-(2-aminoethyl)-9H-purin-6-amine

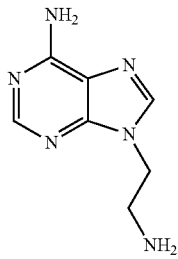 [SMILES: NCCn1cnc2c(N)ncnc21]

¹H NMR (400 MHz, Methanol-d₄) δ 8.19 (d, J=1.9 Hz, 1H, CH), 8.10 (d, J=1.8 Hz, 1H, CH), 4.26 (td, J=6.3, 1.8 Hz, 2H, CH₂NH₂), 3.14 (t, J=6.3 Hz) & 3.06 (t, J=6.3 Hz) (2H, NCH₂). ¹³C NMR (101 MHz, MeOD) δ 157.33, 153.67 (CH), 150.83, 142.97 (CH), 120.17, 47.57 & 45.49 (NCH₂), 42.23 (CH₂NH₂). MS (ESI): [M+H]⁺=179; [M+Na]⁺=201.

tri-tert-butyl 10-(6-(3-(2-(6-amino-9H-purin-9-yl)ethyl)ureido)hexanoyl)-1,4,7,10-tetraazacyclododecane-1,4,7-tricarboxylate

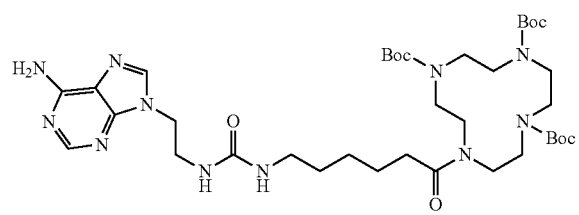 [SMILES: CC(C)(C)OC(=O)N1CCN(C(=O)CCCCCNC(=O)NCCn2cnc3c(N)ncnc32)CCN(C(=O)OC(C)(C)C)CCN(C(=O)OC(C)(C)C)CC1]

¹H NMR (400 MHz, Chloroform-d) δ 8.21 (s, 1H, CH), 7.76 (s, 1H, CH), 6.34 (br. s, 2H, NH₂), 5.61 (t, J=5.8 Hz, 1H, NH), 5.37 (t, J=5.6 Hz, 1H, NH), 4.29 (t, J=5.7 Hz, 2H, CH₂), 3.62-3.51 (m, 2H, CH₂), 3.49-3.20 (m, 16H, cyclen-CH₂), 3.12-2.99 (m, 2H, CH₂), 2.23 (t, J=7.2 Hz, 2H, CH₂), 1.61-1.47 (m, 2H, CH₂), 1.40 (d, J=9.6 Hz, 29H, Boc-CH₃ & CH₂), 1.30-1.13 (m, 2H, CH₂). ¹³C NMR (101 MHz, CDCl₃) δ 158.37, 157.09, 155.51, 155.28, 152.59, 149.80, 141.06, 119.42, 80.30, 80.22, 80.05, 53.26, 50.12, 49.39, 44.12, 39.85, 39.72, 29.65, 28.31, 28.28, 26.37, 24.59. MS (ESI) [M+H]⁺=790; [M+Na]⁺=812; [M+K]⁺=828.

1-(6-(1,4,7,10-tetraazacyclododecan-1-yl)-6-oxohexyl)-3-(2-(6-amino-9H-purin-9-yl)ethyl)urea (2.2)

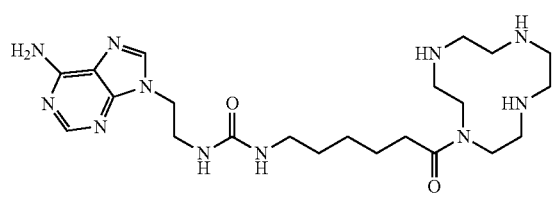 [SMILES: Nc1ncnc2c1ncn2CCNC(=O)NCCCCCC(=O)N1CCNCCNCCNCC1]

¹H NMR (400 MHz, Methanol-d₄) δ 8.20 (s, 1H, CH), 8.04 (s, 1H, CH), 4.38-4.24 (m, 2H, CH₂), 3.65-3.35 (m, 6H, cyclen-CH₂ & CH₂), 3.01 (t, J=7.2 Hz, 1H), 3.16-2.62 (m, 12H, cyclen-CH₂), 2.44 (t, J=7.7 Hz, 2H, CH₂), 1.59 (p, J=7.3 Hz, 2H, CH$_2$), 1.40 (p, J=7.3 Hz, 2H, CH$_2$), 1.35-1.18 (m, 2H, CH$_2$). $^{13}$C NMR (101 MHz, MeOD) δ 175.69, 159.22, 155.73, 152.12, 149.36, 141.47, 118.54, 53.28, 49.01, 45.13, 44.02, 43.76, 39.22, 39.05, 32.98, 29.44, 25.94, 24.49. MS (ESI) [M+H]$^+$=490; [M+Na]$^+$=512.

Discussion

The relative levels of UBA5 and UFM1 protein expression in a variety of cancers, including leukaemia (MV4-11 and K562), breast (MCF-7 and MDA-231), lung (A549 and Sk-Luci6), and melanoma (MDA-435) cell lines was investigated. From the screen, the highest levels of UBA5 expression were identified in leukaemia (K562), lung (Sk-Luci6), and melanoma (MDA-435), compared to other cancerous and normal lung (MRC9) cell lines (as shown in FIG. 1A). The pattern of free UFM1 protein expression levels did not parallel that of UBA5 (as shown in FIG. 2), although there were noticeable differences in the relative amounts of UFM1-protein conjugates between cell lines (FIG. 1B). Based on the elevated levels of UBA5 in cancer cells compared to normal lung cells, this system is implicated in cancer progression.

Figure 1:
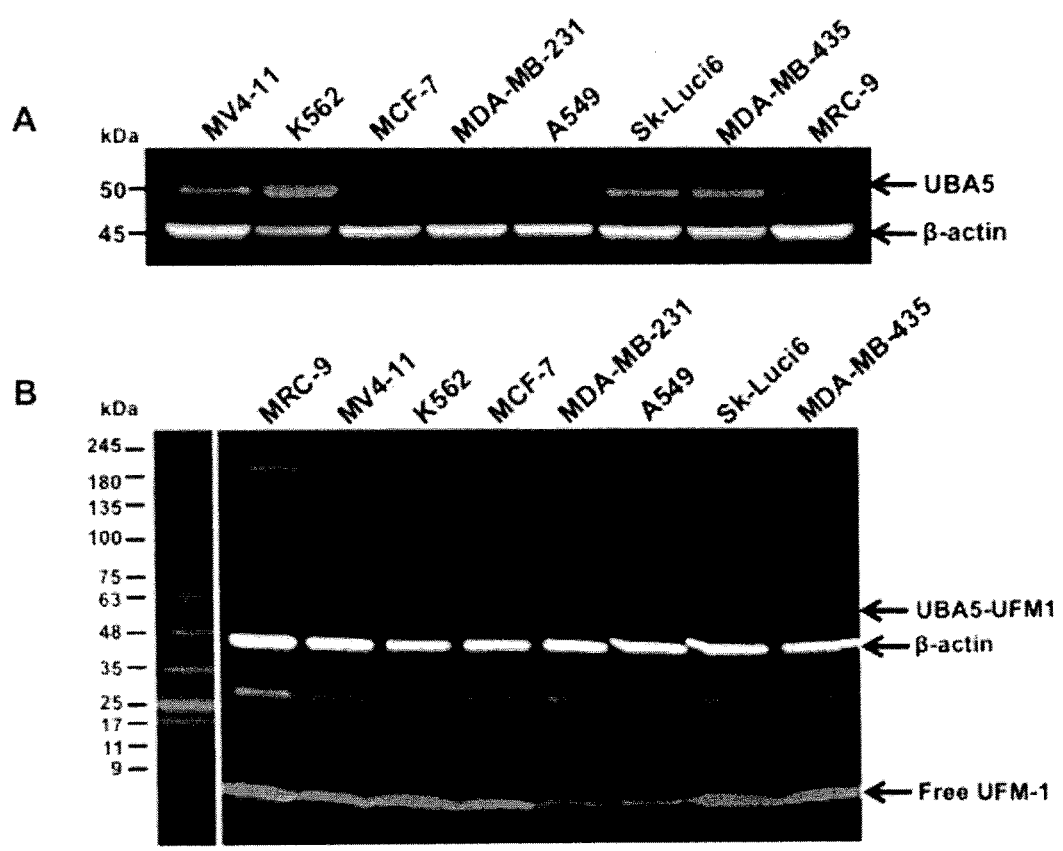
FIG. 1 is a Western blot showing UBA5 protein levels in human cancer cell lines.
Figure 2:
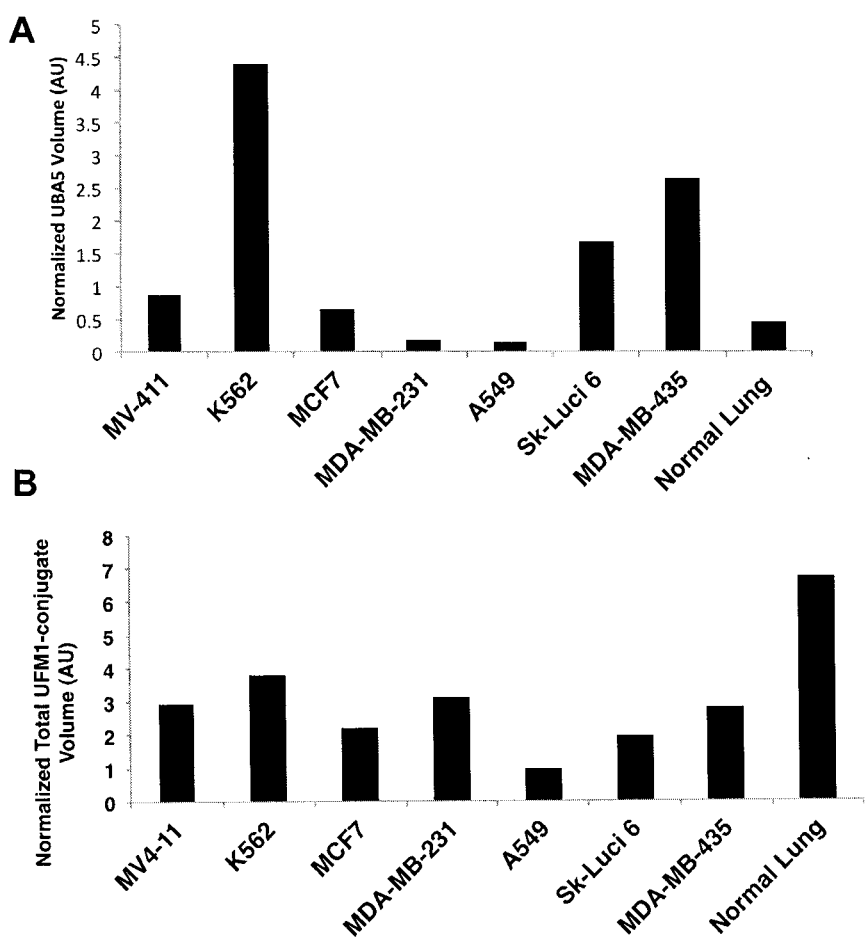
FIG. 2 is the quantification of Western blots conducted in FIG. 1 using β-actin as a loading control for protein quantity.

FIG. 1 shows the detection of UBA5 and UFM1 expression levels across a panel of cancer cells. (A) Relative protein expression levels of human UBA5 in a range of human cell lines, including: leukaemia (MV-4-11, K562), breast (MCF-7, MDA-MB-231), lung (A549, Sk-Luci6), melanoma (MDA-MB-435), and normal lung (MRC-9). Elevated UBA5 levels were detected in K562, Sk-Luci6 and MDA-MB-435 cells, with relatively no difference in expression amongst MV-4-11, MCF-7, MDA-MB-231 and A549 cancer cell lines compared to normal lung cells. (B) The pattern of UFM1 expression differed between cancer cell lines, however there was no notable difference in total UFM1 detected among cancers and normal cell line. Blots were incubated with rabbit anti-UBA5 (A, 1:1000) or anti-UFM1 (B, 1:1000) antibodies, and mouse anti-β-actin (1:5000) was detected as a loading control. Bands were visualized using anti-rabbit Alexa Fluor® 647 (red, 1:5000) and anti-mouse Alexa Fluor® 488 (green, 1:20,000) secondary antibodies.

Westerns conducted in FIG. 1 were quantified using β-actin as a loading control for protein quantity as shown in FIG. 2. Normalized volume is quantified in arbitrary units (AU) based on relative intensities of bands compared to the control β-actin using ImageLab software (BioRad). (A) Normalized volumes of UBA5 in a range of human cell lines, including: leukaemia (MV-4-11, K562), breast (MCF-7, MDA-MB-231), lung (A549, Sk-Luci6), melanoma (MDA-MB-435), and normal lung (MRC-9). Elevated UBA5 levels were observed in K562, Sk-Luci6 and MDA-MB-435 cells, with relatively no difference in expression amongst MV-4-11, MCF-7, MDA-MB-231 and A549 cancer cell lines compared to normal lung cells. (B) In the same cell lines screened for UBA5 levels, there was no noticeable difference in the level of total UFM1 conjugates among cancers, however conjugate levels were lower in all cancer compared to normal lung cells. There was no noticeable difference in total UFM1 levels (conjugated and free UFM1) among all cell lines.

Figure 3:
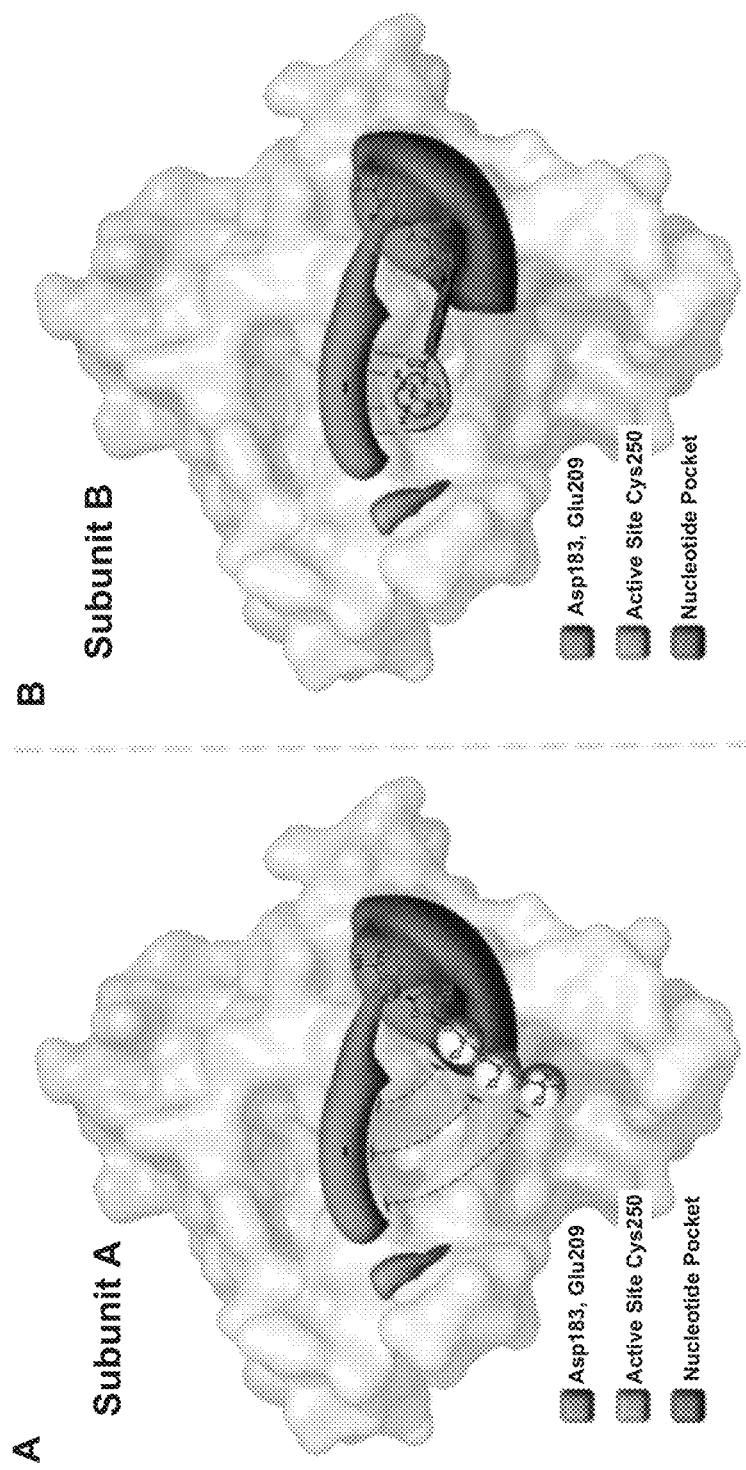
FIG. 3 shows the binding pocket of UBA5 in relation to a compound of the disclosure.

The active form of UBA5 exists as a homodimer. However, crystallographic data suggests that the ATP pocket responsible for UFM1 adenylation, denoted as the "active" ATP pocket on subunit A, is conformationally unequivalent to the ATP pocket on subunit B. Specifically, the lysine (K127) and conserved aspartic acid (D183) residues of the ATP pocket, which are crucial to facilitate the adenylation of UFM1 by coordinating to the phosphate tail of ATP and the ribose sugar alcohols, are well defined in subunit A but poorly resolved in subunit B, indicating a structural flexibility of these residues in the "inactive" UBA5 monomer. From the co-crystallization of UBA5 with ATP, it was identified that the triphosphate tail of ATP repelled away from the negatively charged D183 and glutamic acid (E209) residues that compose the outer edge of the ATP binding pocket in subunit A and B (as shown in FIG. 3A). Compound 1.5.Zn is proposed to bind in the nucleotide binding pocket, as well as an electropositive zinc (II) coordination complex bound to electronegative residues on UBA5 (as shown in FIG. 3B). These two moieties were separated by an alkyl chain in compound 1.5.Zn, which bound to the conformationally flexible pocket in subunit B (structure as shown in FIG. 4A).

The ability of compound 1.5.Zn to inhibit UBA5 and block subsequent UFM1 transfer to its E2 (UFC1) was evaluated by detecting the relative amounts of E2-UFM1 product formation in a transthiolation assay. As shown in FIG. 4B, dose-dependent inhibition of the UFC1-UFM1 protein conjugate formation with increasing concentrations of compound 1.5.Zn was observed, which exhibited an IC$_{50}$ of 4.1 μM (95% Confidence Interval [CI]=2.1-7.7 μM) (as shown in FIG. 4C). Reactions were resolved using SDS-PAGE and bands were stained with Coomassie™ Brilliant Blue R-250. Relative inhibition was assessed by comparison of treated lanes with the normal reaction lane (Lane 8 in both gels). Positive controls included incubation of reactions with DTT or a non-hydrolyzable form of ATP, ApCpp.

Removing the zinc(II) metal reduced inhibitor activity (as shown in FIG. 4D), and the zinc(II) cyclen complex itself was able to impede the transthiolation reaction at 100 μM (as shown in FIG. 5).

The proposed function of the zinc(II)cyclen portion of 1.5.Zn in mediating inhibition involves coordination to D183 and/or E209 in order to block ATP binding. However, the position of D183 is conserved in all known E1 activating enzymes and plays a role in the adenylation step of Ubl activation. The selectivity of 1.5.Zn for UBA5 over other E1 enzymes, such as the Ub activating enzyme (UAE), and the activating enzyme for the Ubl, NEDD8 (NAE), both of which demonstrate greater activity in cells than UBA5 was investigated. As shown in FIG. 6A, 1.5.Zn inhibited UBA5 selectively over UAE (IC$_{50}$=76.7 μM, 95% C.I. 51.5-114 μM) and NAE (IC$_{50}$=10$^3$ μM, 95% C.I. 69.4-153 μM), with significant differences observed dose-dependently (as shown in FIG. 6B). As shown in FIG. 6(A), initial rates of E2-UFM1 product formation were determined by measuring the extent of E1-E2 transthiolation in 30 s intervals over 2.5 minutes. Concentrations of UBA5 (1 μM), UFM1 (10 μM), and UFC1 (10 μM) were held constant, while the concentration of ATP was varied from 0 to 1 mM. Substrate inhibition of the transthiolation reaction was observed at concentrations >250 μM ATP (n=5). As shown in FIG. 6(B), non-competitive inhibition of E1-E2 transthiolation was exhibited by 1.5.Zn (5 μM). Protein concentrations were held constant as in (A), and concentrations of ATP were varied from 0 to 1 mM (n=3). Nonlinear regression was performed to obtain the K$_M$ (for ATP), V$_{MAX}$, and k$_{CAT}$ in the absence and presence of inhibitor The activity of 1.5.Zn was also tested against 97 human kinases in a scanEDGE® kinome screen (DiscoveRx). Interestingly, despite the adenosine functionality of 1.5.Zn, little activity was shown against representative kinases from each family in the human genome (FIG. 6B) including hetero- and homodimers with two active ATP sites (FIG. 7). As shown in FIG. 7(A), 1.5.Zn inhibits UBA5 (black) selectively over two other E1 enzymes, NAE (grey; n=3-6) and UAE (white; n=3-6), despite the conserved nature of residues in and around the ATP pocket in all E1 s. Statistical analysis was performed through GraphPad Prism 6, with significance calculated using an ANOVA with Tukey's multiple comparison post hoc test (*p<0.05, p<0.01, *p<0.001, ****p<0.0001). As shown in FIG. 7(B) the results from a scanEDGE kinome screen (DiscoveRx), which tested inhibitor potency at 10 µM of 1.5.Zn, demonstrates no inhibition (denoted as inhibition >65% of control, red circles) across a panel of 97 representative mammalian kinases from all families in the kinome.

The effect of 1.5.Zn on the proliferation of cells with differing UBA5 expression levels was also evaluated. No inhibition of cell growth was observed in cells that exhibit low levels of UBA5 expression, such as normal lung cells (MRC9) and lung cancer cells (A549) (FIG. 8). However, a significant decrease in cellular proliferation in lung cancer cells with elevated UBA5 levels (Sk-Luci6) when treated with increasing concentrations of 1.5.Zn was observed. Furthermore, no cell death was observed in all treated cells. As shown in FIG. 8(A), compared to the normal untreated reaction, 1.5.Zn dose-dependently inhibited the E1-E2 transthiolation for UAE, as observed through a decrease in the E2-Ub band strength and a simultaneous increase in the band strength of free E2. Bands were detected using a mouse anti-His primary antibody (1:500), followed by subsequent detection with a goat anti-mouse HRP-conjugated secondary antibody (1:5000). Blots were visualized through enhanced chemiluminescence. As shown in FIG. 8(B), nonlinear regression of UAE inhibition by 1.5.Zn revealed >20-fold selectivity for UBA5 over UAE ($IC_{50}$=76.7 µM, 95% C.I. 51.5-114 µM; n=3-6).

FIG. 9 shows the dose-dependent inhibition of the NEDD8 activating enzyme (NAE) by 1.5.Zn. As shown in FIG. 9(A), compared to the untreated reaction, 1.5.Zn dose-dependently inhibited the E1-E2 transthiolation for NAE, as observed through a decrease in the E2-NEDD8 band strength. Bands were detected using a rabbit anti-NEDD8 primary antibody (1:500), followed by subsequent detection with a goat anti-rabbit HRP-conjugated secondary antibody (1:5000). Blots were visualized through enhanced chemiluminescence. As shown in FIG. 9(B) Nonlinear regression of NAE inhibition by 1.5.Zn revealed >20-fold selectivity for UBA5 over NAE ($IC_{50}$=103 µM, 95% C.I. 69.4-153 µM; n=3-6).

FIG. 10 shows a complete kinase inhibition profile. The results from a scanEDGE kinome screen (DiscoveRx), which tested inhibitor potency at 10 µM of 1.5.Zn, demonstrated little inhibition (denoted as >35% retention of activity of the control) across a panel of 97 representative mammalian kinases from all families in the human kinome.

FIG. 11 shows the presence of a zinc(II)cyclen moiety does not interfere with the kinome screen signal. The scanEDGE kinome screen (DiscoveRx) employs a detection system that quantifies the amount of DNA-tagged kinase (using qPCR) that is displaced from a solid surface containing immobilized ligand by the introduction of a potential competing substrate. Unlike other zinc(II)cyclen moieties that are able to bind to and intercalate between DNA bases (REF), the compound is unable to compete with kinase detection and does not affect signal strength, as compared to DMSO control and a known DNA intercalating agent, in both phage and mammalian expression systems.

FIG. 12 shows the decrease in the proliferation of a lung cancer cell exhibiting elevated UBA5 levels. Three cell lines expressing differing levels of UBA5, notably A549 (UBA5 null) (Graph B), MRC9 (UBA5 low) (Graph A) and SK-luci6 (UBA5 high) (Graph C), were treated with increasing doses of 1.5.Zn. Selective antiproliferative activity was observed for highly expressing UBA5 cells (ANOVA, n=3, p<0.001). Total number of cells was counted at 24-hour time points over a 72-hour period.

FIG. 13 shows the inhibition of UBA5 using various compounds of the disclosure.

By inversing the negative functionality typically associated off the 5' carbon of adenosine in ATP, UBA5 was selectively targeted over other E1 enzymes and other ATP-dependent proteins. In one embodiment, impeding the activity of a cellular support system such as the UFM1 labeling pathway can aid in the design of combination therapies that could sensitize cancer cells to a primary drug that induces apoptosis via ER-stress, effectively slowing cancer progression.

Effect of Chain Length on Inhibitor Activity

The alkyl linker separating the adenosine scaffold from the zinc(II)cyclen coordination complex of 1.5.Zn was modified from 1-4 methylene groups, to yield compounds 1.1.Zn-1.4.Zn. A structure-activity relationship (SAR) was observed in varying the linker length, with compound 1.5.Zn being the most potent zinc-coordinated complex against UBA5. The identity and in vitro activity of each derivative is shown in FIG. 14 and Table 1 (evaluated using a transthiolation assay, described in detail within the Materials and Methods).

Effect of Chelatable Metal Ion on Inhibitor Activity

Removing the $Zn^{2+}$ centre from inhibitors 1.1.Zn-1.5.Zn, yielding derivatives 1.1.L-1.5.L (L=denotes these compounds as un-metalated ligands), reduces inhibitor activity against UBA5, compared with parent compounds 1.1.Zn-1.5.Zn. The identity and in vitro activity of 1.1.L-1.5.L (evaluated using a transthiolation assay, described in detail within the Materials and Methods) is shown in FIG. 15 and Table 2.

Identity of Chelatable Metal Ion on Inhibitor Activity

Replacing the $Zn^{2+}$ centre from 1.5.Zn with other divalent transition metal cations $Cu^{2+}$, $Mn^{2+}$, $Ni^{2+}$ and $Fe^{2+}$ yielded derivatives 1.5.Cu, 1.5.Mn, 1.5.Ni and 1.5.Fe, respectively (here, the Cu, Mn, Ni, and Fe denote different divalent metal centre derivatives from 1.5.Zn). The identity and in vitro activity of 1.5.Cu, 1.5.Mn, 1.5.Ni and 1.5.Fe and 1.1.Cu-1.4.Cu (evaluated using a transthiolation assay, described in detail within the Materials and Methods) is shown in FIGS. 16 and 17 and Table 3.

Effect of Polyazamacrocycle on Inhibitor Activity

The 1,4,7,10-tetraazacyclododecane (cyclen) coordinated to the $Zn^{2+}$ centre in 1.5.Zn was varied to investigate the role of the coordinated polyazamacrole on inhibitor activity. Replacing cyclen in 1.1.Zn and 1.5.Zn with 1,4,8,11-tetraazacyclotetradecane (cyclam) yielded compounds 1.1.Cy.Zn and 1.5.Cy.Zn (Cy=denotes a cyclam in place of the cyclen). The identity and in vitro activity of compounds 1.1.Cy.Zn and 1.5.Cy.Zn (evaluated using a transthiolation assay, described in detail within the Materials and Methods) is shown in FIG. 18 and Table 4.

Effect of Linker on Inhibitor Activity

The alkyl chain of inhibitor 1.5.Zn, 1.1.Zn and 1.1.Cy.Zn were modified by replacing the carbonyl functionality in the amide linkage to the cyclen group with a methylene group, resulting in a tertiary amine in place of the amide, yielding derivative 1.5.A.Zn, 1.5.A.Cu, 1.1.A.Zn, 1.1.A.Cu and 1.1.A.Cy.Zn respectively (A=denotes alkyl methylene replacement of amide carbonyl group). The identity and in vitro activity of 1.5.A.Zn, 1.5.A.Cu, 1.1.A.Zn, 1.1.A.Cu and 1.1.A.Cy.Zn (evaluated using a transthiolation assay, described in detail within the Materials and Methods) is shown in FIG. 19 and Table 5.

Effect of Functionalization

The adenosine purine base within 1.5.Zn and 1.5.Cu was modified at the C-6 position, where the amino group was replaced with varying groups of size and polarity. The 1.5.Zn and 1.5.Cu derivatives were functionalized at C-6 with a 1-aminoindan group yielding derivatives 1.5.An6.Zn and 1.5.An6.Cu, respectively (An6=denotes 1-aminoindan at the C-6 position). The identity and in vitro activity of compounds 1.5.An6.Zn and 1.5.An6.Cu (evaluated using a transthiolation assay, described in detail within the Materials and Methods) is shown in FIG. 20 and Table 6.

Non-Competitive Binding with ATP

The mode of inhibition of 1.5.Zn with respect to ATP was evaluated. The inhibition of transthiolation was quantified kinetically in the presence of increasing concentrations of ATP. In the absence of 1.5.Zn, a substrate inhibition profile of ATP was observed on the transthiolation reaction between UBA5 and UFC1, where at high concentrations of ATP there was a decline in the observed transthiolation $V_{MAX}$ (1.90±0.096 pmol min$^{-1}$) with an associated $K_M$ of 16.5±2.53 μM for ATP and a $k_{CAT}$ of 0.218±0.010 min$^{-1}$. In the presence of 1.5.Zn (5 μM), a noncompetitive inhibition profile was observed as supported by a decrease in the $k_{CAT}$ (0.113±0.016 min$^{-1}$) and $V_{MAX}$ (0.988±0.137 pmol min$^{-1}$) with no significant change in the $K_M$ for ATP (24.9±9.63 μM). Unlike the canonical E1 enzymes, UBA5 is an asymmetric homodimer, with one monomer mediating UFM1 activation and the second acting as a regulatory subunit. Without being bound by theory, the kinetic data suggest that 1.5.Zn may elicit its activity by interacting with the ATP pocket and surrounding residues on the inactive regulatory UBA5 monomer, or alternatively by binding to an allosteric site on the UBA5 homodimer. The kinetic activity of UBA5 in the presence and absence of compound 1.5.Zn (evaluated using a transthiolation assay, described in detail within the Materials and Methods) is shown in FIG. 21.

Selective Inhibition for UBA5 Over Other ATP-Dependent Enzymes-E1 UAE

As measured using the transthiolation assay for the Ub activating enzyme (UAE), 1.5.Zn is ~20-fold selective for UBA5 ($IC_{50}$=4.0 μM, 95% Confidence Interval (C.I.)=1.74-9.34 μM) over UAE ($IC_{50}$=78.5 μM, 95% C.I.=51.2-120.5 μM). The graphical representation of UBA5 selectivity over UAE demonstrated by 1.5.Zn (evaluated using a transthiolation assay, described in detail within the Materials and Methods) is shown in FIG. 22.

Selective Inhibition for UBA5 Over Other ATP-Dependent Enzymes-E1 NAE

As measured using the transthiolation assay for the NEDD8 activating enzyme (UAE), 1.5.Zn is ~20-fold selective for UBA5 ($IC_{50}$=4.0 μM, 95% Confidence Interval (C.I.)=1.74-9.34 μM) over NAE ($IC_{50}$=66.8 μM, 95% C.I.=31.4-141.8 μM). The graphical representation of UBA5 selectivity over NAE demonstrated by 1.5.Zn (evaluated using a transthiolation assay, described in detail within the Materials and Methods) is shown in FIG. 23.

Selective Inhibition for UBA5 Over Human Kinases

The off-target activity against other ATP-dependent enzymes, such as kinases, was investigated. There was no significant inhibition of ATP binding to 97 human kinases by 1.5.Zn, when evaluated at 10 μM within a DiscoveRx scanEDGE$^{SM}$ kinome screen (assay described in detail at: http://www.discoverx.com/services/drug-discovery-development-services/kinase-profiling/kinomescan/scanedge).

The graphical representation of the kinome screen for 1.5.Zn data is shown in FIGS. 7 and 10. As denoted by the absence of large circles, 1.5.Zn demonstrates no significant inhibition of representative human kinases. Image generated using TREEspot™ Software Tool and reprinted with permission from KINOMEscan®, a division of DiscoveRx Corporation, © DISCOVERX CORPORATION 2010.

Differential UBA5 Protein Expression Observed in Cancer Cells

Previous work has indicated varying expression levels of UBA5 and other proteins in the UFM1 pathway among normal and diseased (cancerous) cell lines. The ability of 1.5.Zn to disrupt the growth of cancer cells that demonstrate high UBA5 protein expression levels was investigated. The results indicate that compounds of the disclosure may be used as an adjuvant to sensitize the growth of certain cancer types that demonstrate elevated UBA5 expression, and/or as an adjuvant that may sensitize cancer cells to apoptosis when administered with an agent that induces ER stress.

The levels of UBA5 protein expression in cancer cells was investigated, in order to identify which cells (with the highest UBA5 protein expression) would likely be more susceptible to an effect of UBA5 inhibition. As shown in FIG. 24, differential UBA5 protein expression among three lung cell lines was identified: Sk-Luci6 (large cell anaplastic lung cancer), A549 (adenocarcinomic human alveolar basal epithelial cancer), and MRC9 (normal lung fibroblasts). Therefore, UBA5 protein expression levels vary among normal and cancerous cell lines. The full methods for cell lysis and identification of protein expression is described in detail within the Materials and Methods submitted, the results of which are shown in FIG. 24.

Reduction in the Proliferation of Cancer Cells with High Levels of UBA5 Protein Expression Selective inhibition of Sk-Luci6 (high-UBA) cell growth incurred by treatment with 1.5.Zn was observed, with relatively no effect on cell proliferation of A549 or MRC9 cells (low-UBA5), up to treatment with 200 μM of 1.5.Zn. 1.5.Zn demonstrates cancer cell line-specific effects on those with higher UBA5 protein expression. Without being bound by theory, pre-treating UBA5-high cells with compounds of the disclosure may sensitize them to the effects of an ER-stress inducing agent and will induce apoptosis at lower concentrations of such agents. The graphical representation of the effects of 1.5.Zn on cell growth (evaluated using Trypan blue exclusion assay, as described in the Materials and Methods submitted in May 2014), is shown in FIG. 12 and phase contrast images in 25. Sk-Luci6 lung cancer cell (prominent UBA5 expression) growth was arrested with increasing concentrations of, compared with no effect seen in A549 lung carcinoma cells (low UBA5 expression). Images were taken at 72 h using a tissue culture microscope and a Motic Moticam 10, 10.0 MP, at 100× total magnification Effect on UFMylation Previous research on the role of UFM1 protein labeling within normal somatic cells has shown that UFMylation is important for erythroid differentiation in mice. Furthermore, genetic silencing of UFM1 and proteins within the UFMylation pathway led to the sensitization of pancreatic cells to apoptosis when treated with chemical agents that induce endoplasmic reticulum (ER) stress. UFM1 labeling has also been implicated in driving breast cancer cell proliferation through the transactivation of key transcription factors.

1.5.Zn selectively disrupts UBA5 activity in vitro as measured using transthiolation assays. The intracellular inhibition of UBA5 was evaluated in order to investigate its use as a molecular tool to study cellular UFMylation by UBA5 inactivation. As measured through Western Blot analysis, treatment of cells (A549=UBA5 low, while Sk-Luci6 and K562=UBA5 high) with 1.5.Zn resulted in the disruption of UFM1 conjugation to downstream proteins when evaluated at a 72 h time point, as a result of the intracellular inhibition of UBA5. Therefore, 1.5.Zn works intracellularly as a UBA5 inhibitor. The graphical representation of the intracellular inhibition of UFM1 protein conjugation (evaluated using Western Blot analysis, described in detail within the Materials and Methods submitted in May 2014) is shown in FIG. 26. Decreased UFMylation levels were detected with increasing concentrations of 1.5.Zn in Sk-Luci6 and K562 cells compared to A549 cells. Bands were visualized using anti-rabbit Alexa Fluor® 647 (1:5000, for UFM1 conjugates) and anti-mouse Alexa Fluor® 488 (1:20,000, for actin) secondary antibodies.

Effect on Other Ubl Conjugation 1.5.Zn selectively abrogates UBA5 activity in vitro against other E1 enzymes (NAE, UAE and SAE), as well as a panel of 97 human kinases. The intracellular selectivity of 1.5.Zn at disrupting UFMylation over other Ub/Ubl labeling processes, in order to validate the selective inhibition of UBA5 within a physiologically relevant environment was investigated. Mimicking the selectivity observed within transthiolation assays in vitro, 1.5.Zn retains its selectivity against E1 enzymes within high-UBA5 expressing cells (Sk-Luci6) and low-UBA5 expressing cells (A549), evidenced by no intracellular NAE inhibition due to the unchanged NEDD8 downstream protein labeling as detected by Western blot analysis. Therefore, the compounds work selectively on the UBA5 pathway, and can be used as a tool to investigate the roles of UFMylation in cells. The graphical representation of the intracellular inhibition of UFM1 protein conjugation (evaluated using Western Blot analysis, described in detail within the Materials and Methods, with the exception of the rabbit primary anti-NEDD8 antibody used to visualize NEDD8 conjugates, in a dilution of 1:1000) is shown FIG. 27. Bands were visualized using anti-rabbit Alexa Fluor® 647 (1:5000, for NEDD8 and NEDD8 conjugates) and anti-mouse Alexa Fluor® 488 (1:20,000, for actin) secondary antibodies.

TABLE 1

Summary of the activities displayed by UBA5 inhibitors 1.1.Zn-1.5.Zn, as identified in a transthiolation enzymatic assay.

| Compound | IC$_{50}$ (µM) | 95% Confidence Interval (µM) |
| --- | --- | --- |
| 1.1.Zn | 10.5 | 4.23-25.9 |
| 1.2.Zn | 8.9 | 4.55-17.5 |
| 1.3.Zn | 23.3 | 7.29-74.36 |
| 1.4.Zn | 5.2 | 0.88-31.0 |
| 1.5.Zn | 4.0 | 1.74-9.34 |

TABLE 2

Summary of the percent inhibition displayed by ligands 1.1 and 1.3 against UBA5 as identified in a transthiolation enzymatic assay (n = 1).

| [Ligand] (µM) | % Inhibition | |
| --- | --- | --- |
| | 1.1 | 1.3 |
| 100 | 26 | 0 |
| 50 | 4 | 11 |
| 10 | 31 | 28 |
| 5 | 41 | 17 |

TABLE 2-continued

Summary of the percent inhibition displayed by ligands 1.1 and 1.3 against UBA5 as identified in a transthiolation enzymatic assay (n = 1).

| [Ligand] (µM) | % Inhibition | |
| --- | --- | --- |
| | 1.1 | 1.3 |
| 1 | 25 | 10 |
| 0.1 | 0 | 24 |

TABLE 3

Summary of the activities displayed by UBA5 inhibitors 1.1.Cu-1.5.Cu, as identified in a transthiolation enzymatic assay (methylene groups = 1 to 5; n = 3). All of 1.1.Cu-1.5.Cu showed little activity compared to the 1.1.Zn-1.5.Zn derivatives.

| Compound | IC$_{50}$ (µM) | 95% Confidence Interval (µM) |
| --- | --- | --- |
| 1.1.Cu | >100 | N/A |
| 1.2.Cu | 39.6 | 9.51-165* |
| 1.3.Cu | >100 | N/A |
| 1.4.Cu | 38.8 | 5.75-261* |
| 1.5.Cu | >100 | N/A |

*95% C.I.s were calculated based on trend observed from testing compounds 1.1.Cu-1.5.Cu from 0.1-100 µM

TABLE 4

Summary of the activities displayed by UBA5 inhibitors 1.1.Cy.Zn and 1.1.Cy.Cu, as identified in a transthiolation enzymatic assay (n = 3).

| Compound | IC$_{50}$ (µM) | 95% Confidence Interval (µM) |
| --- | --- | --- |
| 1.1.Cy.Zn | 4.24 | 3.03-5.93 |
| 1.1.Cy.Cu | 45.4 | 23.0 to 89.4 |

TABLE 5

Summary of the activities displayed by UBA5 inhibitors 1.5.A.Zn, 1.5.A.Cu, compared to 1.5.Zn, and compounds 1.1.A.Zn, 1.1.A.Cu and 1.1.A.Cy.Zn were compared to 1.1.Zn as identified in a transthiolation enzymatic assay (n = 3).

| Compound | IC$_{50}$ (µM) | 95% Confidence Interval (µM) |
| --- | --- | --- |
| 1.5.A.Zn | 38.2 | 5.73-255* |
| 1.5.A.Cu | >100 | N/A |
| 1.5.Zn | 4.0 | 1.74-9.34 |
| 1.1.A.Cy.Zn | 20 | 3.90 to 102* |
| 1.1.A.Zn | 7.61 | 3.49-16.6 |
| 1.1.A.Cu | 21.1 | 3.23-137* |
| 1.1.Zn | 10.5 | 4.23-25.9 |

*95% C.I.s were calculated based on trend observed from testing compounds 1.1.Cu-1.5.Cu from 0.1-100 µM

TABLE 6

Summary of the activities displayed by UBA5 inhibitors 1.5.An6.Zn and 1.5.An6.Cu, as identified in a transthiolation enzymatic assay (n = 3).

| Compound | IC$_{50}$ (µM) |
| --- | --- |
| 1.5.An6.Zn | 13.6 |
| 1.5.An6.Cu | 12.5 |

REFERENCES CITED HEREIN AND INCORPORATED BY REFERENCE

1. J. Biol. Chem. 1983, 258, 8206-8214.
2. Nat Rev Mol Cell Biol., 2009, 10(5), 319-331.

3. J. Biol. Chem. 2010, 285, 20273-20280.
4. EMBO J. 2004, 5; 23 (9), 1977-86
5. Nat. Comm. 2011, DOI: 10.1038/ncomms1182
6. PloS ONE. 2011, 6, 4, e18517
7. Biochem Biophys Res Commun. 2007, 362(4), 1079-84.
8. World Health Organization 2014, Fact Sheet No. 375: Leishmaniasis, http://www.who.int/mediacentre/fact-sheets/fs375/en/>
9. World Health Organization 2010, Technical Report Series No. 949, Costs of medicines in current use for the treatment of leishmaniasis. http://www.who.int/leishmaniasis/research/978 92 4 12 949 6 Annex6.pdf?ua=1
10. Parasitology 2006, 133 Suppl 2: S87-112.
11. PLOS Neglected Tropical Diseases, 2014, 8 (2), e2707.
12. Molecular Microbiology 2012, 86(1), 187-198.
13. PLoS ONE 2011, 6 (1), e16156.

The invention claimed is:
1. A compound of the Formula (I)

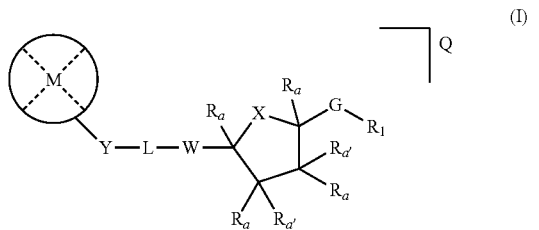

wherein

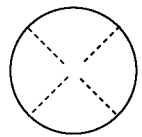

is a polyazamacrocycle chelating group;
M is a chelatable metal ion;
Y is
   (i) —C(=O)—, or
   (ii) —CH$_2$—;
L is
   (i) (C$_1$-C$_{20}$)-alkylene, wherein
      (i.a) at least one of the carbon atoms is optionally replaced with a heteroatom selected from O, NR' and S, wherein R' is H, (C$_1$-C$_6$)-alkyl or C(=O)—(C$_1$-C$_6$)-alkyl;
      (i.b) two or three adjacent carbon atoms are joined together to form a (C$_3$-C$_{10}$)-cycloalkyl group or —(C$_6$-C$_{10}$)-aryl group; and/or
      (i.c) the (C$_1$-C$_{20}$)-alkylene group is optionally substituted with at least one halo;
   (ii) (C$_2$-C$_{20}$)-alkenylene, wherein
      (ii.a) at least one of the carbon atoms is optionally replaced with a heteroatom selected from O, NR' and S, wherein R' is H, (C$_1$-C$_6$)-alkyl or C(=O)—(C$_1$-C$_6$)-alkyl;
      (ii.b) two or three adjacent carbon atoms are optionally joined together to form a (C$_3$-C$_{10}$)-cycloalkyl group or —(C$_6$-C$_{10}$)-aryl group; and/or
      (ii.c) the (C$_2$-C$_{20}$)-alkenylene group is optionally substituted with at least one halo;
   or
   (iii) a polyethylene glycol (PEG) moiety;
W is
   (i) —NH—C(=O)—;
   (ii) —NR'—, wherein R' is H, (C$_1$-C$_6$)-alkyl or —C(=O)—(C$_1$-C$_6$)-alkyl
X is
   (i) —O—;
   (ii) NR', wherein R' is H, (al-CO-alkyl or —C(=O)—(C$_1$-C$_6$)-alkyl;
   (iii) —S—; or —S(=O)$_2$—; or
   (iv) —C(R")$_2$, wherein each R" is independently or simultaneously H, halo or (C$_1$-C$_6$)-alkyl;
R$_a$ and R$_{a'}$ are each independently or simultaneously
   (i) H;
   (ii) OH;
   (iii) halo; or
   (iv) (C$_1$-C$_3$)-alkyl; and
G is
   (i) O;
   (ii) S;
   (iii) NR$_2$;
R$_1$ and R$_2$ are each independently or simultaneously
   (i) H;
   (ii) (C$_1$-C$_6$)-alkyl;
   (iii) (C$_3$-C$_{10}$)-cycloalkyl;
   (iv) (C$_3$-C$_{10}$)-heterocycloalkyl;
   (v) —(CH$_2$)$_n$—(C$_6$-C$_{10}$)-aryl;
   (vi) —(CH$_2$)$_n$—(C$_5$-C$_{10}$)-heteroaryl;
   or
R$_1$ and R$_2$ are joined together to form a
   (vii) guanine or a guanine derivative;
   (viii) cytosine or a cytosine derivative;
   (ix) thymine or a thymine derivaivte;
   (x) adenine or an adenine derivative;
and Q is any suitable counteranion;
or a solvate, prodrug and/or stereoisomer thereof.

2. The compound of the Formula (I) according to claim 1, wherein the polyazamacrocycle chelating group has the following structure

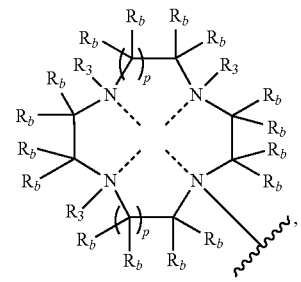

wherein
   each R$_3$ is independently or simultaneously
      (i) H; or
      (ii) (C$_1$-C$_3$)-alkyl;
   each R$_b$ is independently or simultaneously
      (i) H;
      (ii) (C$_1$-C$_3$)-alkyl; or
      (iii) CF$_3$; and
   p is 1 or 2.

3. The compound of the Formula (I) according to claim 2, wherein the polyazamacrocycle chelating group has the following structure

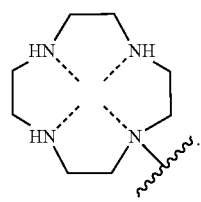

4. The compound of the Formula (I) according to claim 1, wherein L is $(C_1-C_{10})$-alkylene or $(C_2-C_{10})$-alkenylene, wherein (i) one to five carbon atoms are optionally replaced with a heteroatom selected from O, NR' and S, wherein R' is H, $(C_1-C_5)$-alkyl or —C(=O)—$(C_1-C_6)$-alkyl; (ii) two or three adjacent carbon atoms are joined together to form a $(C_5-C_7)$-cycloalkyl group or —$(C_6)$-aryl group; and/or (iii) the $(C_1-C_{10})$-alkylene or $(C_2-C_{10})$-alkenylene is optionally substituted with at least one fluoro.

5. The compound of the Formula (I) according to claim 4, wherein L is $(C_1-C_6)$-alkylene or $(C_2-C_6)$-alkenylene.

6. The compound of the Formula (I) according to claim 1, wherein W is —NH—C(=O)—.

7. The compound of the Formula (I) according to claim 1, wherein W is —NR'—, wherein R' is H, $(C_1-C_6)$-alkyl or —C(=O)—$(C_1-C_6)$-alkyl.

8. The compound of the Formula (I) according to claim 1, wherein the moiety

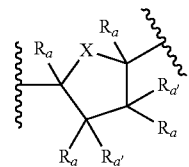

has the following structure

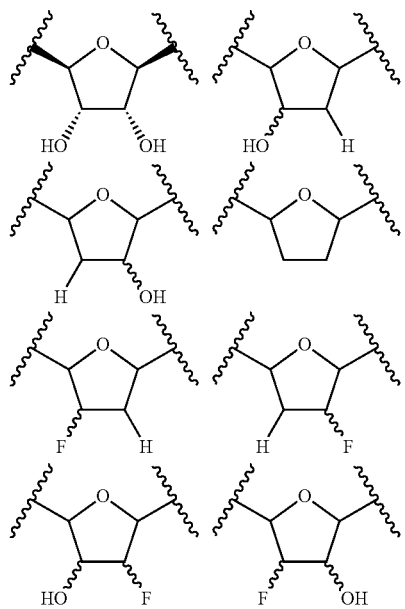

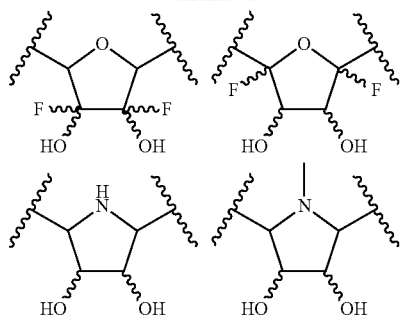

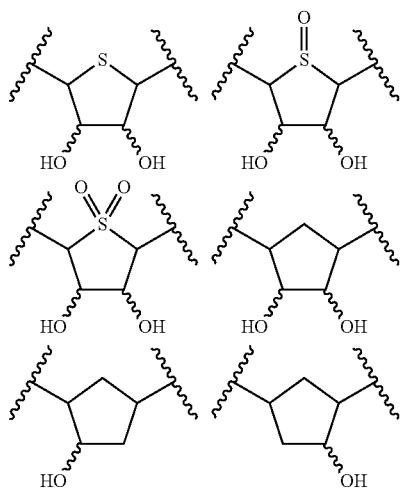

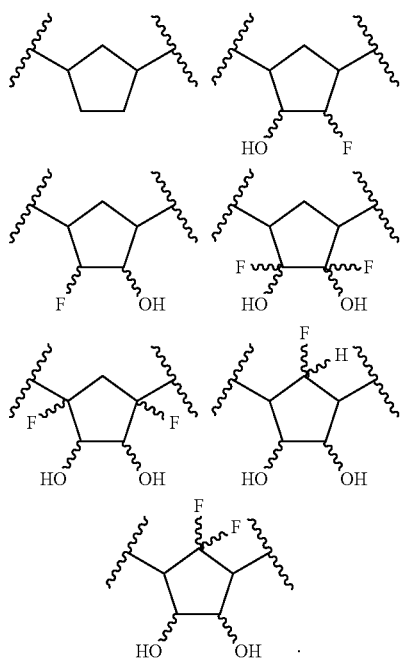

9. The compound of the Formula (I) according to claim 8, wherein the structure is

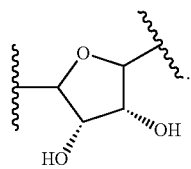 [SMILES: *C1OC(*)[C@H](O)[C@@H]1O]

10. The compound of the Formula (I) according claim 1, wherein $R_1$ and $R_2$ are each independently or simultaneously
   (i) H,
   (ii) cyclopentyl or cyclohexyl;
   (iii) morpholinyl or piperazinyl;
   (iv) phenyl or —(CH$_2$)-phenyl;
   (v) naphthyl or —(CH$_2$)-naphthyl;
   (vi) pyridinyl or —CH$_2$-pyridinyl;
   or
   $R_1$ and $R_2$ are joined together to form a
   (vii) guanine or a guanine derivative;
   (viii) cytosine or a cytosine derivative;
   (ix) thymine or a thymine derivative; or
   (x) adenine or an adenine derivative.

11. The compound of the Formula (I) according claim 10, wherein $R_1$ and $R_2$ are joined together to form adenine or an adenine derivative.

12. The compound of the Formula (I) according claim 11, wherein $R_1$ and $R_2$ are joined to form an adenine derivative having the structure

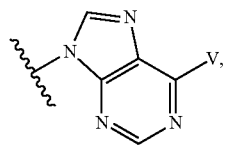

wherein
   V is H, halo, $(C_1\text{-}C_6)$-alkyl, $(C_6\text{-}C_{10})$-aryl, $(C_5\text{-}C_{10})$-heteroaryl, $(C_3\text{-}C_{10})$-cycloalkyl, $(C_3\text{-}C_{10})$-heterocycloalkyl, the latter five groups being optionally substituted with —N(R$^1$)$_2$, wherein R' is H or $(C_1\text{-}C_3)$-alkyl.

13. The compound of the Formula (I) according to claim 1, wherein M is $Zn^{2+}$, $Cu^{2+}$, $Fe^{2+}$, $Ni^{2+}$, $Mn^{2+}$, $Co^{2+}$, $Pd^{2+}$, $Gd^{2+}$, $Tb^{2+}$, $Eu^{2+}$ or $Mo^{2+}$.

14. The compound of the Formula (I) according to claim 13, wherein M is $Zn^{2+}$.

15. A compound of the Formula (II)

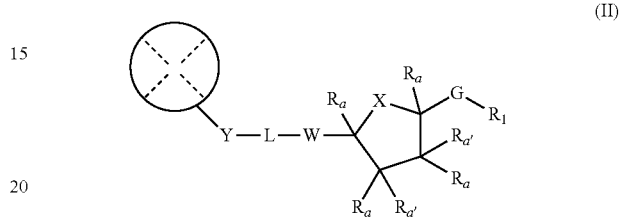

(II)

wherein
   Y, L, W, X, $R_a$, $R_{a'}$, $R_1$ and the polyazamacrocycle are as defined in claim 1.

16. A method for the treatment or prevention of a disease or condition mediated by UBA5, comprising administering a pharmaceutically effective amount of a compound of claim 1 to a subject in need thereof.

17. The method according to claim 16, wherein the disease or condition is cancer, wherein the cancer is leukemia, lung cancer or melanoma.

18. The method according to claim 17, wherein the leukemia is acute leukemia, chronic leukemia, lymphocytic leukemia or myelogenous leukemia.

19. The method according to claim 16, for the treatment of a parasitic disease.

* * * * *

UNITED STATES PATENT AND TRADEMARK OFFICE
CERTIFICATE OF CORRECTION

PATENT NO. : 10,077,284 B2
APPLICATION NO. : 15/315123
DATED : September 18, 2018
INVENTOR(S) : Patrick Thomas Gunning et al.

Page 1 of 1

It is certified that error appears in the above-identified patent and that said Letters Patent is hereby corrected as shown below:

In the Claims

Claim 1, Column 85, Line 30, should contain the Formula reference "(I)"

Claim 1, Column 85, Line 61, "... (C1-C6)-alkyl or C(=0)-" should read "... (C1-C6)-alkyl or -C(=0)-"

Claim 1, Column 86, Line 9, "... R' is H, (al-CO-alkyl or –C(=0)-" should read "... R' is H, (C1-C6)-alkyl or –C(=0)-"

Claim 1, Column 86, Line 35, "... a thymine derivaivte;" should read "... a thymine derivative;"

Signed and Sealed this
Eighth Day of January, 2019

Andrei Iancu
*Director of the United States Patent and Trademark Office*